US012655486B2

(12) United States Patent
Self et al.

(10) Patent No.: US 12,655,486 B2
(45) Date of Patent: Jun. 16, 2026

(54) **COMPOSITIONS AND METHODS FOR DETECTING *PLASMODIUM* SPECIES NUCLEIC ACID**

(71) Applicants: Gen-Probe Incorporated, San Diego, CA (US); Grifols Diagnostic Solutions Inc., San Diego, CA (US)

(72) Inventors: Deanna Self, Escondido, CA (US); Jeffrey M. Linnen, Poway, CA (US); Vanessa Bres, San Diego, CA (US)

(73) Assignees: Gen-Probe Incorporated, San Diego, CA (US); Grifols Diagnostic Solutions Inc., San Diego, CA (US)

( * ) Notice: Subject to any disclaimer, the term of this patent is extended or adjusted under 35 U.S.C. 154(b) by 1252 days.

(21) Appl. No.: 17/414,635

(22) PCT Filed: Dec. 20, 2019

(86) PCT No.: PCT/US2019/067777
§ 371 (c)(1),
(2) Date: Nov. 9, 2021

(87) PCT Pub. No.: WO2020/132408
PCT Pub. Date: Jun. 25, 2020

(65) Prior Publication Data
US 2022/0243285 A1     Aug. 4, 2022

Related U.S. Application Data

(60) Provisional application No. 62/782,945, filed on Dec. 20, 2018.

(51) Int. Cl.
*C12Q 1/68* (2018.01)
*C12Q 1/6893* (2018.01)
*C12Q 1/6844* (2018.01)

(52) U.S. Cl.
CPC ......... *C12Q 1/6893* (2013.01); *C12Q 1/6844* (2013.01)

(58) Field of Classification Search
None
See application file for complete search history.

(56) References Cited

U.S. PATENT DOCUMENTS

2010/0183679 A1    7/2010    Tsuboi et al.

FOREIGN PATENT DOCUMENTS

| | | | |
|---|---|---|---|
| CN | 102220419 B | 6/2013 | |
| CN | 104673901 B | 5/2018 | |
| JP | 2010-527583 A | 8/2010 | |
| WO | WO 2008/146938 | 12/2008 | |
| WO | WO 2009/074649 A1 | 6/2009 | |
| WO | WO-2010080616 A1 * | 7/2010 | .......... C12Q 1/6883 |
| WO | WO 2013/159293 A1 | 10/2013 | |
| WO | WO 2017/189746 A1 | 11/2017 | |
| WO | WO 2018/226798 A1 | 12/2018 | |
| WO | WO 2020/132408 A2 | 6/2020 | |

OTHER PUBLICATIONS

Lowe, T et al. A computer program for selection of oligonucleotide primers for polymerase cahin reaction. Nucleic Acids Research, vol. 18(7), p. 1757-1761, (1990).*
WIPO Application No. PCT/US2019/067777, PCT International Preliminary Report on Patentability mailed Jun. 16, 2021.
WIPO Application No. PCT/US2019/067777, PCT International Search Report and Written Opinion of the International Searching Authority mailed Jun. 25, 2020.
WIPO Application No. PCT/US2019/067777, PCT Invitation to Pay Additional Fees mailed Mar. 17, 2020.

* cited by examiner

*Primary Examiner* — Aaron A Priest
(74) *Attorney, Agent, or Firm* — Alston & Bird LLP

(57) ABSTRACT

Disclosed are nucleic acid oligomers, including amplification oligomers, detection probes, and capture probes, for detection of *Plasmodium* species nucleic acid in a sample. Also disclosed are methods of specific nucleic acid amplification and detection, including amplification and detection of target nucleic acid in real time, using the disclosed oligomers, as well as corresponding reaction mixtures and kits.

24 Claims, No Drawings

Specification includes a Sequence Listing.

COMPOSITIONS AND METHODS FOR DETECTING *PLASMODIUM* SPECIES NUCLEIC ACID

CROSS-REFERENCE TO RELATED APPLICATIONS

This application is a U.S. National Stage entry of International Application No. PCT/US2019/067777, filed Dec. 20, 2019, which claims priority to U.S. Provisional Application Ser. No. 62/782,945, filed Dec. 20, 2018, which are incorporated herein by reference.

REFERENCE TO SEQUENCE LISTING

The instant application contains a Sequence Listing which has been submitted in ASCII format via EFS-Web and is hereby incorporated by reference in its entirety. Said ASCII Copy, created on Oct. 28, 2019, is named "GDS_0110PC_20191028_Seq_Listing_ST25" and is 56,087 bytes in size.

BACKGROUND

Malaria is a serious disease caused by intra-erythrocyte parasites of the genus of *Plasmodium*. The parasites are contracted via an infected female Anopheles mosquito bite. There are five species of the parasite that cause malaria in humans: *P. falciparum, P. knowlesi, P. malariae, P. ovale* and *P. vivax*. According to the World Health Organization (WHO) there were 216 million cases of Malaria worldwide in 2016, and of those, 445,000 were fatal.

The United States Food and Drug Administration (U.S. FDA) has implemented strict blood screening guidelines for accepting or deferring donors who have travelled to malaria-endemic regions. Travelers are deferred for one year after traveling to an endemic region, or three years if the donor is a former resident of an endemic region. People who have been diagnosed with malaria are deferred for three years after the completion of treatment and symptom free. There are no approved tests available in the U.S. to screen blood donations for *Plasmodium*. This requires careful screening of prospective donors via a medical questionnaire.

In endemic countries, WHO recommends testing by thick blood films or using a highly sensitive enzyme immunoassay. In non-endemic countries, WHO recommends donors are deferred for six months from the last potential exposure combined with malaria antibody testing using a highly sensitive enzyme immunoassay. Donors may be re-instated if there is no evidence of malarial antibody. There is a risk that these methods are not effective to detect low levels of parasitemia where transmission may occur.

Transfused Transmitted Malaria (TTM) has been documented in the U.S. There have been 46 cases of TTM reported between 1911 and 2015 and the latest case was reported in 2018. There is a need for a specific and sensitive nucleic acid test (NAT) for detecting *Plasmodium* species in a sample to reduce TTM and the number of deferred donors.

SUMMARY

In one aspect, the present invention provides a method for specifically detecting *Plasmodium* species nucleic acid in a sample. The method generally includes (1) contacting a sample, the sample suspected of containing *Plasmodium* species nucleic acid, with at least two oligomers for amplifying a target region of a *Plasmodium* species target nucleic acid, (2) performing an in vitro nucleic acid amplification reaction, where any *Plasmodium* target nucleic acid present in said sample is used as a template for generating an amplification product, and (3) detecting the presence or absence of the amplification product, thereby indicating the presence or absence of *Plasmodium* species target nucleic acid in said sample. In some embodiments, the at least two amplification oligomers comprise (a) an amplification oligomer comprising a target-hybridizing sequence (i) that is from about 14 to about 20 contiguous nucleotides in length, is contained in the sequence of SEQ ID NO: 162, and includes the sequence of SEQ ID NO: 163, or (ii) that is from about 14 to about 25 contiguous nucleotides in length, is contained in the sequence of SEQ ID NO: 166, and includes SEQ ID NO: 167 or SEQ ID NO: 168; and (b) an amplification oligomer comprising a target-hybridizing sequence that is from about 15 to about 33 contiguous nucleotides in length, is contained in SEQ ID NO: 169 and includes the sequence of SEQ ID NO: 171, SEQ ID NO: 172, or SEQ ID NO: 173. In other embodiments, the at least two amplification oligomers comprise (a') an amplification oligomer comprising a target-hybridizing sequence that is contained in the sequence of SEQ ID NO: 185 and includes the sequence of SEQ ID NO: 37, SEQ ID NO: 46, or SEQ ID NO: 187; and (b') an amplification oligomer comprising a target-hybridizing sequence that is contained in the sequence of SEQ ID NO: 188 and includes the sequence of SEQ ID NO: 83, SEQ ID NO: 84, or SEQ ID NO: 182.

In some embodiments of a method as above where the at least two amplification oligomers comprise the amplification oligomers of (a)(i) and (b), the target-hybridizing sequence of (a)(i) is selected from SEQ ID NOs: 21, 23-25, 32, 33, 35, 54, and 55. In other embodiments, the target-hybridizing sequence of (a)(i) is contained in the sequence of SEQ ID NO: 164 and includes the sequence of SEQ ID NO: 165; in some such variations, the target-hybridizing sequence of (a)(i) is selected from SEQ ID NOs: 21, 23-25, 32, 33, and 35.

In some embodiments of a method as above where the at least two amplification oligomers comprise the amplification oligomers of (a)(ii) and (b), the target-hybridizing sequence of (a)(ii) includes the sequence of SEQ ID NO: 167; in some such variations, the target-hybridizing sequence of (a)(ii) is selected from the SEQ ID NOs: 28-31, 34, 40, 41, and 49-51. In other embodiments, the target-hybridizing sequence of (a)(ii) includes the sequence of SEQ ID NO: 168; in some such variations, the target-hybridizing sequence of (a)(ii) is selected from SEQ ID NOs: 38, 39, 43, 44, and 53.

In some embodiments of a method as above where the at least two amplification oligomers comprise the amplification oligomers of (a) and (b), the target-hybridizing sequence of (b) is selected from SEQ ID NOs: 80-82 and 85-100. In other embodiments, the target-hybridizing sequence of (b) is contained in the sequence of SEQ ID NO: 170 and includes the sequence of SEQ ID NO: 171 or SEQ ID NO: 172. In some variations where the target-hybridizing sequence of (b) is contained in the sequence of SEQ ID NO: 170 and includes the sequence of SEQ ID NO: 171, the target-hybridizing sequence of (b) is selected from SEQ ID NOs: 81, 82, 85, 87-90, 94, and 96-98. In some variations where the target-hybridizing sequence of (b) is contained in the sequence of SEQ ID NO: 170 and includes the sequence of SEQ ID NO: 172, the target-hybridizing sequence of (b) is selected from SEQ ID NOs: 80, 82, 85, and 87-100.

In some embodiments of a method as above where the at least two amplification oligomers comprise the amplification oligomers of (a') and (b'), the target-hybridizing sequence of (a') is selected from SEQ ID NOs: 37, 46, 183, and 184. In other embodiments, the target-hybridizing sequence of (a') is contained in the sequence of SEQ ID NO: 186; in some such variations, the target-hybridizing sequence of (a') is SEQ ID NO: 183 or SEQ ID NO: 184. In certain embodiments where the at least two amplification oligomers comprise the amplification oligomers of (a') and (b'), the target-hybridizing sequence of (b') is selected from SEQ ID NOs: 83, 84, and 182. In more particular variations, the target-hybridizing sequence of (a') is SEQ ID NO: 183 or SEQ ID NO: 184 and the target-hybridizing sequence of (b') is SEQ ID NO: 182.

In some embodiments of a method as above, the amplification oligomer of (b) or (b') is a promoter primer or promoter provider further comprising a promoter sequence located 5' to the target-hybridizing sequence of (b) or (b'), respectively. A particularly suitable promoter sequence is a T7 promoter sequence such as, e.g., SEQ ID NO: 179. In specific variations where an amplification oligomer of (b) includes a promoter sequence, the amplification oligomer of (b) comprises a sequence selected from SEQ ID NOs: 57-59 and 62-77. In specific variations where an amplification oligomer of (b') includes a promoter sequence, the amplification oligomer of (b') comprises a sequence selected from SEQ ID NOs: 60, 61, and 181.

Particularly suitable pairs of amplification oligomer target-hybridizing sequences of (a) and (b), respectively, are (A) SEQ ID NO: 30 and SEQ ID NO: 82, (B) SEQ ID NO: 33 and SEQ ID NO: 82, (C) SEQ ID NO: 49 and SEQ ID NO: 82, (D) SEQ ID NO: 21 and SEQ ID NO: 89, (E) SEQ ID NO: 30 and SEQ ID NO: 89, (F) SEQ ID NO: 33 and SEQ ID NO: 89, (G) SEQ ID NO: 49 and SEQ ID NO: 89, (H) SEQ ID NO: 21 and SEQ ID NO: 92, (I) SEQ ID NO: 30 and SEQ ID NO: 92, (J) SEQ ID NO: 21 and SEQ ID NO: 94, (K) SEQ ID NO: 34 and SEQ ID NO: 94, (L) SEQ ID NO: 53 and SEQ ID NO: 94, (M) SEQ ID NO: 21 and SEQ ID NO: 95, (N) SEQ ID NO: 34 and SEQ ID NO: 95, and (0) SEQ ID NO: 53 and SEQ ID NO: 95. In some such embodiments, the amplification oligomer of (b) is a promoter primer or promoter provider further comprising a promoter sequence (for example, a T7 promoter sequence such as, e.g., SEQ ID NO: 179) located 5' to the target-hybridizing sequence of (b).

In some embodiments of a method as above where the at least two amplification oligomers comprise the amplification oligomers of (a) and (b), the at least two amplification oligomers comprise first and second amplification oligomers as in (a). In some such variations, the at least two amplification oligomers comprise first and second amplification oligomers as in (a)(ii). Particularly suitable first and second amplification oligomers of (a)(ii) include a first amplification oligomer comprising a target-hybridizing sequence that includes the sequence of SEQ ID NO: 167 (e.g., the target-hybridizing sequence of SEQ ID NO: 34) and a second amplification oligomer comprising a target-hybridizing sequence that includes the sequence of SEQ ID NO: 168 (e.g., the target-hybridizing sequence of SEQ ID NO: 53).

In other embodiments of a method as above where the at least two amplification oligomers comprise the amplification oligomers of (a) and (b), the at least two amplification oligomers comprise an amplification oligomer as in (a)(i) and an amplification oligomer as in (a)(ii). In some such embodiments, the amplification oligomer as in (a)(i) comprises a target-hybridizing sequence that is contained in the sequence of SEQ ID NO: 164 and includes the sequence of SEQ ID NO: 165 (e.g., the target-hybridizing sequence of SEQ ID NO: 21), and the amplification oligomer as in (a)(ii) comprises a target-hybridizing sequence that includes the sequence of SEQ ID NO: 167 (e.g., the target-hybridizing sequence of SEQ ID NO: 34).

In some embodiments of a method as above where the at least two amplification oligomers comprise the amplification oligomers of (a) and (b), the at least two amplification oligomers comprise first and second amplification oligomers of (b). In some such embodiments, each of the first and second amplification oligomers of (b) comprises a target-hybridizing sequence that is contained in SEQ ID NO: 170 and includes the sequence of SEQ ID NO: 171 or SEQ ID NO: 172 (e.g., a first amplification oligomer comprising the target-hybridizing sequence of SEQ ID NO: 94 and a second amplification oligomer comprising the target-hybridizing sequence of SEQ ID NO: 95). In some variations, each of the first and second amplification oligomers of (b) is a promoter primer or promoter provider further comprising a promoter sequence located 5' to the target-hybridizing sequence of (b). A particularly suitable promoter sequence is a T7 promoter sequence such as, e.g., SEQ ID NO: 179. In specific variations where each of the first and second amplification oligomers of (b) includes a promoter sequence, the first amplification oligomer of (b) comprises the sequence of SEQ ID NO: 71 and the second amplification oligomer of (b) comprises the sequence of SEQ ID NO: 72.

In certain embodiments of a method for detecting *Plasmodium* species nucleic acid in a sample as above, the method further includes purifying the target nucleic acid from other components in the sample before step (1). In some such variations, the purifying step comprises contacting the sample with at least one capture probe oligomer comprising a target-hybridizing sequence covalently attached to a sequence or moiety that binds to an immobilized probe, where the target-hybridizing sequence configured to specifically hybridize to the *Plasmodium* species target nucleic acid. Particularly suitable capture probe oligomer target-hybridizing sequences include sequences that are up to about 30 contiguous nucleotides in length and include a sequence selected from SEQ ID NOs: 11-15, 17, 19, and 20, including DNA equivalents and DNA/RNA chimerics thereof. In more specific variations, the capture probe oligomer target-hybridizing sequence is selected from SEQ ID NOs: 11-15, 17, 19, and 20, including DNA equivalents and DNA/RNA chimerics thereof. In some embodiments, the purifying step comprises contacting the sample with at least two capture probe oligomers (e.g., at least two capture probe oligomers as above); in some such variations, the at least two capture probe oligomers include a first capture probe oligomer comprising the target-hybridizing sequence of SEQ ID NO: 19 and a second capture probe oligomer comprising the target-hybridizing sequence of SEQ ID NO: 20.

In some embodiments of a method for detecting *Plasmodium* species nucleic acid in a sample as above, the detecting step (3) comprises contacting the in vitro nucleic acid amplification reaction with at least one detection probe oligomer comprising a target-hybridizing sequence configured to specifically hybridize to the amplification product under conditions whereby the presence or absence of the amplification product is determined, thereby indicating the presence or absence of *Plasmodium* species in the sample. In some such embodiments where the at least two amplification oligomers comprise the amplification oligomers of (a) and (b), the detection probe oligomer target-hybridizing sequence is from about 13 to about 40 nucleotides in length and is (i) contained in the sequence of SEQ ID NO: 196 or its complement, or a DNA equivalent or DNA/RNA chimeric thereof, and (ii) includes a sequence selected from SEQ ID NO: 175, SEQ ID NO: 176, SEQ ID NO: 177, and SEQ ID NO: 178, including complements, DNA equivalents, and DNA/RNA equivalents thereof. Suitable detection probe oligomer target-hybridizing sequences include SEQ ID NOs: 131, 132, 135, 140, 145, 147-157, and 159-161, including complements, DNA equivalents, and DNA/RNA chimerics thereof. In certain embodiments, the detection probe oligomer target-hybridizing sequence is (i) contained in the sequence of SEQ ID NO: 197 or its complement, or a DNA equivalent or DNA/RNA chimeric thereof, and (ii) includes the sequence of SEQ ID NO: 174 or SEQ ID NO: 175, including complements, DNA equivalents, and DNA/RNA chimerics thereof; in some such variations comprising the sequence of SEQ ID NO: 174 or its complement, or a DNA equivalent or DNA/RNA chimeric thereof, the detection probe oligomer target-hybridizing sequence is selected from SEQ ID NOs: 148-155 and 159, including complements, DNA equivalents, and DNA/RNA chimerics thereof, in other such variations comprising SEQ ID NO: 175 or its complement, or a DNA equivalent or DNA/RNA chimeric thereof, the detection probe oligomer target-hybridizing sequence is selected from SEQ ID NOs: 147, 156, 157, 160, and 161, including complements, DNA equivalents, and DNA/RNA chimerics thereof. In certain embodiments, the detection probe oligomer target-hybridizing sequence is (i) contained in the sequence of SEQ ID NO: 196 or its complement, or a DNA equivalent or DNA/RNA chimeric thereof, and (ii) includes a sequence selected from SEQ ID NO: 177 and SEQ ID NO: 178, including complements, DNA equivalents, and DNA/RNA chimerics thereof; in some such variations, the detection probe oligomer target-hybridizing sequence is selected from SEQ ID NOs: 131, 132, 135, 140, 147, 156, 157, 160, and 161, including complements, DNA equivalents, and DNA/RNA chimerics thereof.

In other embodiments of a method as above where the detecting step (3) comprises contacting the in vitro nucleic acid amplification reaction with at least one detection probe oligomer and where the at least two amplification oligomers comprise the amplification oligomers of (a') and (b'), the detection probe oligomer target-hybridizing sequence is at least about 13 nucleotides in length and is (i) contained in the sequence of SEQ ID NO: 189 or its complement, or a DNA equivalent or DNA/RNA chimeric thereof, and (ii) includes a sequence selected from SEQ ID NO: 190 and SEQ ID NO: 191, including complements, DNA equivalents, and DNA/RNA equivalents thereof. In some such variations, the detection probe oligomer target-hybridizing sequence is selected from the SEQ ID NOs: 125-130 and 143, including complements, DNA equivalents, and DNA/RNA chimerics thereof.

In particular variations of a method for detecting *Plasmodium* species nucleic acid in a sample as above, where the detecting step (3) comprises contacting the in vitro nucleic acid amplification reaction with at least one detection probe oligomer and where the at least two amplification oligomers comprise the amplification oligomers of (a) and (b), the amplification oligomer target-hybridizing sequence of (a), the amplification oligomer target-hybridizing sequence of (b), and the detection probe oligomer target-hybridizing sequence, respectively, are (A) SEQ ID NO: 30, SEQ ID NO: 82, and SEQ ID NO: 151 or its complement, or a DNA equivalent or DNA/RNA chimeric of SEQ ID NO: 151 or its complement; (B) SEQ ID NO: 30, SEQ ID NO: 82, and SEQ ID NO: 157 or its complement, or a DNA equivalent or DNA/RNA chimeric of SEQ ID NO: 157 or its complement; (C) SEQ ID NO: 33, SEQ ID NO: 82, and SEQ ID NO: 155 or its complement, or a DNA equivalent or DNA/RNA chimeric of SEQ ID NO: 155 or its complement; (D) SEQ ID NO: 49, SEQ ID NO: 82, and SEQ ID NO: 150 or its complement, or a DNA equivalent or DNA/RNA chimeric of SEQ ID NO: 150 or its complement; (E) SEQ ID NO: 49, SEQ ID NO: 82, and SEQ ID NO: 155 or its complement, or a DNA equivalent or DNA/RNA chimeric of SEQ ID NO: 155 or its complement; (F) SEQ ID NO: 21, SEQ ID NO: 89, and SEQ ID NO: 148 or its complement, or a DNA equivalent or DNA/RNA chimeric of SEQ ID NO: 148 or its complement; (G) SEQ ID NO: 21, SEQ ID NO: 89, and SEQ ID NO: 152 or its complement, or a DNA equivalent or DNA/RNA chimeric of SEQ ID NO: 152 or its complement; (H) SEQ ID NO: 30, SEQ ID NO: 89; and SEQ ID NO: 148 or its complement, or a DNA equivalent or DNA/RNA chimeric of SEQ ID NO: 148 or its complement; (I) SEQ ID NO: 30, SEQ ID NO: 89; and SEQ ID NO: 152 or its complement, or a DNA equivalent or DNA/RNA chimeric of SEQ ID NO: 152 or its complement; (I) SEQ ID NO: 33, SEQ ID NO: 89; and SEQ ID NO: 158 or its complement, or a DNA equivalent or DNA/RNA chimeric of SEQ ID NO: 158 or its complement; (K) SEQ ID NO: 49, SEQ ID NO: 89, and SEQ ID NO: 150 or its complement, or a DNA equivalent or DNA/RNA chimeric of SEQ ID NO: 150 or its complement; (L) SEQ ID NO: 21, SEQ ID NO: 92, and SEQ ID NO: 148 or its complement, or a DNA equivalent or DNA/RNA chimeric of SEQ ID NO: 148 or its complement; (M) SEQ ID NO: 21, SEQ ID NO: 92, and SEQ ID NO: 152 or its complement, or a DNA equivalent or DNA/RNA chimeric of SEQ ID NO: 152 or its complement; (N) SEQ ID NO: 30, SEQ ID NO: 92; and SEQ ID NO: 148 or its complement, or a DNA equivalent or DNA/RNA chimeric of SEQ ID NO: 148 or its complement; (0) SEQ ID NO: 30, SEQ ID NO: 92; and SEQ ID NO: 152 or its complement, or a DNA equivalent or DNA/RNA chimeric of SEQ ID NO: 152 or its complement; (P) SEQ ID NO: 21, SEQ ID NO: 94, and SEQ ID NO: 148 or its complement, or a DNA equivalent or DNA/RNA chimeric of SEQ ID NO: 148 or its complement; (Q) SEQ ID NO: 21, SEQ ID NO: 94, and SEQ ID NO: 152 or its complement, or a DNA equivalent or DNA/RNA chimeric of SEQ ID NO: 152 or its complement; (R) SEQ ID NO: 34, SEQ ID NO: 94, and SEQ ID NO: 148 or its complement, or a DNA equivalent or DNA/RNA chimeric of SEQ ID NO: 148 or its complement; (S) SEQ ID NO: 34, SEQ ID NO: 94, and SEQ ID NO: 152 or its complement, or a DNA equivalent or DNA/RNA chimeric of SEQ ID NO: 152 or its complement; (T) SEQ ID NO: 34, SEQ ID NO: 94, and SEQ ID NO: 157 or its complement, or a DNA equivalent or DNA/RNA chimeric of SEQ ID NO: 157 or its complement; (U) SEQ ID NO: 53, SEQ ID NO: 94, and SEQ ID NO: 148 or its complement, or a DNA equivalent or DNA/RNA chimeric of SEQ ID NO: 148 or its complement; (V) SEQ ID NO: 53, SEQ ID NO: 94, and SEQ ID NO: 152 or its complement, or a DNA equivalent or DNA/RNA chimeric of SEQ ID NO: 152 or its complement; (W) SEQ ID NO: 53, SEQ ID NO: 94, and SEQ ID NO: 157 or its complement, or a DNA equivalent or DNA/RNA chimeric of SEQ ID NO: 157 or its complement; (X) SEQ ID NO: 21, SEQ ID NO: 95, and SEQ ID NO: 148 or its complement, or a DNA equivalent or DNA/RNA chimeric of SEQ ID NO: 148 or its complement; (Y) SEQ ID NO: 21, SEQ ID NO: 95, and SEQ ID NO: 152 or its complement, or a DNA equivalent or DNA/RNA chimeric of SEQ ID NO: 152 or its complement; (Z) SEQ ID NO: 34, SEQ ID NO: 95, and SEQ ID NO: 148 or its complement, or a DNA equivalent or DNA/RNA chimeric of SEQ ID NO: 148 or its complement; (AA) SEQ ID NO: 34, SEQ ID NO: 95, and SEQ ID NO: 152 or its complement, or a DNA equivalent or DNA/RNA chimeric of SEQ ID NO: 152 or its complement; (AB) SEQ ID NO: 34, SEQ ID NO: 95, and SEQ ID NO: 157 or its complement, or a DNA equivalent or DNA/RNA chimeric of SEQ ID NO: 157 or its complement; (AC) SEQ ID NO: 53, SEQ ID NO: 95, and SEQ ID NO: 148 or its complement, or a DNA equivalent or DNA/RNA chimeric of SEQ ID NO: 148 or its complement; (AD) SEQ ID NO: 53, SEQ ID NO: 95, and SEQ ID NO: 152 or its complement, or a DNA equivalent or DNA/RNA chimeric of SEQ ID NO: 152 or its complement; or (AE) SEQ ID NO: 53, SEQ ID NO: 95, and SEQ ID NO: 157 or its complement, or a DNA equivalent or DNA/RNA chimeric of SEQ ID NO: 157 or its complement.

In particular variations of a method for detecting *Plasmodium* species nucleic acid in a sample as above, where the detecting step (3) comprises contacting the in vitro nucleic acid amplification reaction with at least one detection probe oligomer and where the at least two amplification oligomers comprise the amplification oligomers of (a') and (b'), the amplification oligomer target-hybridizing sequence of (a'), the amplification oligomer target-hybridizing sequence of (b'), and the detection probe oligomer target-hybridizing sequence, respectively, are (A) SEQ ID NO: 183, SEQ ID NO: 182, and SEQ ID NO: 126 or its complement, or a DNA equivalent or DNA/RNA chimeric of SEQ ID NO: 126 or its complement; (B) SEQ ID NO: 183, SEQ ID NO: 182, and SEQ ID NO: 127 or its complement, or a DNA equivalent or DNA/RNA chimeric of SEQ ID NO: 127 or its complement; (C) SEQ ID NO: 183, SEQ ID NO: 182, and SEQ ID NO: 128 or its complement, or a DNA equivalent or DNA/RNA chimeric of SEQ ID NO: 128 or its complement; (D) SEQ ID NO: 183, SEQ ID NO: 182, and SEQ ID NO: 143 or its complement, or a DNA equivalent or DNA/RNA chimeric of SEQ ID NO: 143 or its complement; (E) SEQ ID NO: 183, SEQ ID NO: 182, and SEQ ID NO: 129 or its complement, or a DNA equivalent or DNA/RNA chimeric of SEQ ID NO: 129 or its complement; or (F) SEQ ID NO: 184, SEQ ID NO: 182, and SEQ ID NO: 126 or its complement, or a DNA equivalent or DNA/RNA chimeric of SEQ ID NO: 126 or its complement.

In some embodiments of a method as above utilizing at least one detection probe oligomer, the detection probe oligomer comprises a 2' methoxy modification on at least one of a nucleotide residue member of the detection probe oligomer nucleotide sequence.

In some embodiments of a method as above utilizing at least one detection probe oligomer, the detection probe oligomer further includes a detectable label such as, for example, a fluorescent or chemiluminescent label. A particularly suitable chemiluminescent label is a chemiluminescent acridinium ester (AE) compound linked between two nucleobases of the detection probe oligomer. In some embodiments comprising a detectably labeled probe oligomer, the detectable label is a fluorescent label and the detection probe oligomer further includes a non-fluorescent quencher.

In some embodiments of a method as above, the detecting step (3) occurs during the amplifying step (2). In some such embodiments, the method utilizes a detection probe oligomer comprising a fluorescent label and a quencher (e.g., a molecular torch, a molecular beacon, or a TaqMan detection probe).

In some embodiments of a method as above utilizing at least one detection probe oligomer, the detection probe further includes a non-target-hybridizing sequence. In particular variations, a detection probe oligomer comprising a non-target-hybridizing sequence is a hairpin detection probe such as, e.g., a molecular beacon or a molecular torch.

In certain embodiments, a method for detecting *Plasmodium* species nucleic acid in a sample as above utilizes at least two detection probe oligomers. In some such embodiments, the at least two detection probe oligomers comprise first and second detection probe oligomers, where (A) the first detection probe oligomer comprises a target-hybridizing sequence that is (i) contained in the sequence of SEQ ID NO: 197 or its complement, or a DNA equivalent or DNA/RNA chimeric thereof, and (ii) includes the sequence of SEQ ID NO: 175 or its complement, or a DNA equivalent or DNA/RNA chimeric thereof, and (B) the second detection probe oligomer comprises a target-hybridizing sequence that is (i) contained in the sequence of SEQ ID NO: 197 or its complement, or a DNA equivalent or DNA/RNA chimeric thereof, and (ii) includes the sequence of SEQ ID NO: 176 or its complement, or a DNA equivalent or DNA/RNA chimeric thereof. In a more specific variations, the first detection probe oligomer comprises the target-hybridizing sequence of SEQ ID NO: 157 or its complement, or a DNA equivalent or DNA/RNA chimeric thereof, and the second detection probe oligomer comprises a target-hybridizing sequence selected from SEQ ID NO: 148 and SEQ ID NO: 152, including complements, DNA equivalents, and DNA/RNA chimerics thereof.

In certain variations of a method for detecting *Plasmodium* species nucleic acid in a sample as above, the in vitro nucleic acid amplification reaction at step (2) is an isothermal amplification reaction (e.g., a transcription-mediated amplification (TMA) reaction).

In certain variations of a method for detecting *Plasmodium* species nucleic acid in a sample as above, the amplification reaction is a real-time amplification reaction.

In some embodiments of a method for detecting *Plasmodium* species nucleic acid in a sample as above, the sample is a clinical sample. In some embodiments, the sample is a blood sample such as, for example, a red blood cell sample (e.g., a lysed blood cell sample or lysed red blood cell sample).

In another aspect, the present invention provides a combination of at least two oligomers for determining the presence or absence of *Plasmodium* species in a sample. The oligomer combination generally includes at least two oligomers for amplifying a target region of *Plasmodium* species target nucleic acid. In some embodiments, the at least two amplification oligomers comprise (a) an amplification oligomer comprising a target-hybridizing sequence (i) that is from about 14 to about 20 contiguous nucleotides in length, is contained in the sequence of SEQ ID NO: 162, and includes the sequence of SEQ ID NO: 163, or (ii) that is from about 14 to about 25 contiguous nucleotides in length, is contained in the sequence of SEQ ID NO: 166, and includes SEQ ID NO: 167 or SEQ ID NO: 168; and (b) an amplification oligomer comprising a target-hybridizing sequence that is from about 15 to about 33 contiguous nucleotides in length, is contained in SEQ ID NO: 169 and includes the sequence of SEQ ID NO: 171, SEQ ID NO: 172, or SEQ ID NO: 173. In other embodiments, the at least two amplification oligomers comprise (a') an amplification oligomer comprising a target-hybridizing sequence that is contained in the sequence of SEQ ID NO: 185 and includes the sequence of SEQ ID NO: 37, SEQ ID NO: 46, or SEQ ID NO: 187; and (b') an amplification oligomer comprising a target-hybridizing sequence that is contained in the sequence of SEQ ID NO: 188 and includes the sequence of SEQ ID NO: 83, SEQ ID NO: 84, or SEQ ID NO: 182.

In some embodiments of an oligomer combination as above where the at least two amplification oligomers comprise the amplification oligomers of (a)(i) and (b), the target-hybridizing sequence of (a)(i) is selected from SEQ ID NOs: 21, 23-25, 32, 33, 35, 54, and 55. In other embodiments, the target-hybridizing sequence of (a)(i) is contained in the sequence of SEQ ID NO: 164 and includes the sequence of SEQ ID NO: 165; in some such variations, the target-hybridizing sequence of (a)(i) is selected from SEQ ID NOs: 21, 23-25, 32, 33, and 35.

In some embodiments of an oligomer combination as above where the at least two amplification oligomers comprise the amplification oligomers of (a)(ii) and (b), the target-hybridizing sequence of (a)(ii) includes the sequence of SEQ ID NO: 167; in some such variations, the target-hybridizing sequence of (a)(ii) is selected from the SEQ ID NOs: 28-31, 34, 40, 41, and 49-51. In other embodiments, the target-hybridizing sequence of (a)(ii) includes the sequence of SEQ ID NO: 168; in some such variations, the target-hybridizing sequence of (a)(ii) is selected from SEQ ID NOs: 38, 39, 43, 44, and 53.

In some embodiments of an oligomer combination as above where the at least two amplification oligomers comprise the amplification oligomers of (a) and (b), the target-hybridizing sequence of (b) is selected from SEQ ID NOs: 80-82 and 85-100. In other embodiments, the target-hybridizing sequence of (b) is contained in the sequence of SEQ ID NO: 170 and includes the sequence of SEQ ID NO: 171 or SEQ ID NO: 172. In some variations where the target-hybridizing sequence of (b) is contained in the sequence of SEQ ID NO: 170 and includes the sequence of SEQ ID NO: 171, the target-hybridizing sequence of (b) is selected from SEQ ID NOs: 81, 82, 85, 87-90, 94, and 96-98. In some variations where the target-hybridizing sequence of (b) is contained in the sequence of SEQ ID NO: 170 and includes the sequence of SEQ ID NO: 172, the target-hybridizing sequence of (b) is selected from SEQ ID NOs: 80, 82, 85, and 87-100.

In some embodiments of an oligomer combination as above where the at least two amplification oligomers comprise the amplification oligomers of (a') and (b'), the target-hybridizing sequence of (a') is selected from SEQ ID NOs: 37, 46, 183, and 184. In other embodiments, the target-hybridizing sequence of (a') is contained in the sequence of SEQ ID NO: 186; in some such variations, the target-hybridizing sequence of (a') is SEQ ID NO: 183 or SEQ ID NO: 184. In certain embodiments where the at least two amplification oligomers comprise the amplification oligomers of (a') and (b'), the target-hybridizing sequence of (b') is selected from SEQ ID NOs: 83, 84, and 182. In more particular variations, the target-hybridizing sequence of (a') is SEQ ID NO: 183 or SEQ ID NO: 184 and the target-hybridizing sequence of (b') is SEQ ID NO: 182.

In some embodiments of an oligomer combination as above, the amplification oligomer of (b) or (b') is a promoter primer or promoter provider further comprising a promoter sequence located 5' to the target-hybridizing sequence of (b) or (b'), respectively. A particularly suitable promoter sequence is a T7 promoter sequence such as, e.g., SEQ ID NO: 179. In specific variations where an amplification oligomer of (b) includes a promoter sequence, the amplification oligomer of (b) comprises a sequence selected from SEQ ID NOs: 57-59 and 62-77. In specific variations where an amplification oligomer of (b') includes a promoter sequence, the amplification oligomer of (b') comprises a sequence selected from SEQ ID NOs: 60, 61, and 181.

Particularly suitable pairs of amplification oligomer target-hybridizing sequences of (a) and (b), respectively, are (A) SEQ ID NO: 30 and SEQ ID NO: 82, (B) SEQ ID NO: 33 and SEQ ID NO: 82, (C) SEQ ID NO: 49 and SEQ ID NO: 82, (D) SEQ ID NO: 21 and SEQ ID NO: 89, (E) SEQ ID NO: 30 and SEQ ID NO: 89, (F) SEQ ID NO: 33 and SEQ ID NO: 89, (G) SEQ ID NO: 49 and SEQ ID NO: 89, (H) SEQ ID NO: 21 and SEQ ID NO: 92, (I) SEQ ID NO: 30 and SEQ ID NO: 92, (J) SEQ ID NO: 21 and SEQ ID NO: 94, (K) SEQ ID NO: 34 and SEQ ID NO: 94, (L) SEQ ID NO: 53 and SEQ ID NO: 94, (M) SEQ ID NO: 21 and SEQ ID NO: 95, (N) SEQ ID NO: 34 and SEQ ID NO: 95, and (0) SEQ ID NO: 53 and SEQ ID NO: 95. In some such embodiments, the amplification oligomer of (b) is a promoter primer or promoter provider further comprising a promoter sequence (for example, a T7 promoter sequence such as, e.g., SEQ ID NO: 179) located 5' to the target-hybridizing sequence of (b).

In some embodiments of an oligomer combination as above where the at least two amplification oligomers comprise the amplification oligomers of (a) and (b), the at least two amplification oligomers comprise first and second amplification oligomers as in (a). In some such variations, the at least two amplification oligomers comprise first and second amplification oligomers as in (a)(ii). Particularly suitable first and second amplification oligomers of (a)(ii) include a first amplification oligomer comprising a target-hybridizing sequence that includes the sequence of SEQ ID NO: 167 (e.g., the target-hybridizing sequence of SEQ ID NO: 34) and a second amplification oligomer comprising a target-hybridizing sequence that includes the sequence of SEQ ID NO: 168 (e.g., the target-hybridizing sequence of SEQ ID NO: 53).

In other embodiments of an oligomer combination as above where the at least two amplification oligomers comprise the amplification oligomers of (a) and (b), the at least two amplification oligomers comprise an amplification oligomer as in (a)(i) and an amplification oligomer as in (a)(ii). In some such embodiments, the amplification oligomer as in (a)(i) comprises a target-hybridizing sequence that is contained in the sequence of SEQ ID NO: 164 and includes the sequence of SEQ ID NO: 165 (e.g., the target-hybridizing sequence of SEQ ID NO: 21), and the amplification oligomer as in (a)(ii) comprises a target-hybridizing sequence that includes the sequence of SEQ ID NO: 167 (e.g., the target-hybridizing sequence of SEQ ID NO: 34).

In some embodiments of an oligomer combination as above where the at least two amplification oligomers comprise the amplification oligomers of (a) and (b), the at least two amplification oligomers comprise first and second amplification oligomers of (b). In some such embodiments, each of the first and second amplification oligomers of (b) comprises a target-hybridizing sequence that is contained in SEQ ID NO: 170 and includes the sequence of SEQ ID NO: 171 or SEQ ID NO: 172 (e.g., a first amplification oligomer comprising the target-hybridizing sequence of SEQ ID NO: 94 and a second amplification oligomer comprising the target-hybridizing sequence of SEQ ID NO: 95). In some variations, each of the first and second amplification oligomers of (b) is a promoter primer or promoter provider further comprising a promoter sequence located 5' to the target-hybridizing sequence of (b). A particularly suitable promoter sequence is a T7 promoter sequence such as, e.g., SEQ ID NO: 179. In specific variations where each of the first and second amplification oligomers of (b) includes a promoter sequence, the first amplification oligomer of (b)

comprises the sequence of SEQ ID NO: 71 and the second amplification oligomer of (b) comprises the sequence of SEQ ID NO: 72.

In certain embodiments of an oligomer combination for detecting *Plasmodium* species nucleic acid in a sample as above, the oligomer combination further includes at least one capture probe oligomer comprising a target-hybridizing sequence covalently attached to a sequence or moiety that binds to an immobilized probe, where the target-hybridizing sequence configured to specifically hybridize to the *Plasmodium* species target nucleic acid. Particularly suitable capture probe oligomer target-hybridizing sequences include sequences that are up to about 30 contiguous nucleotides in length and include a sequence selected from SEQ ID NOs: 11-15, 17, 19, and 20, including DNA equivalents and DNA/RNA chimerics thereof. In more specific variations, the capture probe oligomer target-hybridizing sequence is selected from SEQ ID NOs: 11-15, 17, 19, and 20, including DNA equivalents and DNA/RNA chimerics thereof. In some embodiments, the oligomer combination includes at least two capture probe oligomers (e.g., at least two capture probe oligomers as above); in some such variations, the at least two capture probe oligomers include a first capture probe oligomer comprising the target-hybridizing sequence of SEQ ID NO: 19 and a second capture probe oligomer comprising the target-hybridizing sequence of SEQ ID NO: 20.

In some embodiments of an oligomer combination for detecting *Plasmodium* species nucleic acid in a sample as above, the oligomer combination further includes at least one detection probe oligomer comprising a target-hybridizing sequence configured to specifically hybridize to a *Plasmodium* species amplicon amplifiable by the at least two amplification oligomers. In some such embodiments where the at least two amplification oligomers comprise the amplification oligomers of (a) and (b), the detection probe oligomer target-hybridizing sequence is from about 13 to about 40 nucleotides in length and is (i) contained in the sequence of SEQ ID NO: 196 or its complement, or a DNA equivalent or DNA/RNA chimeric thereof, and (ii) includes a sequence selected from SEQ ID NO: 175, SEQ ID NO: 176, SEQ ID NO: 177, and SEQ ID NO: 178, including complements, DNA equivalents, and DNA/RNA equivalents thereof. Suitable detection probe oligomer target-hybridizing sequences include SEQ ID NOs: 131, 132, 135, 140, 145, 147-157, and 159-161, including complements, DNA equivalents, and DNA/RNA chimerics thereof. In certain embodiments, the detection probe oligomer target-hybridizing sequence is (i) contained in the sequence of SEQ ID NO: 197 or its complement, or a DNA equivalent or DNA/RNA chimeric thereof, and (ii) includes the sequence of SEQ ID NO: 174 or SEQ ID NO: 175, including complements, DNA equivalents, and DNA/RNA chimerics thereof; in some such variations comprising the sequence of SEQ ID NO: 174 or its complement, or a DNA equivalent or DNA/RNA chimeric thereof, the detection probe oligomer target-hybridizing sequence is selected from SEQ ID NOs: 148-155 and 159, including complements, DNA equivalents, and DNA/RNA chimerics thereof; in other such variations comprising SEQ ID NO: 175 or its complement, or a DNA equivalent or DNA/RNA chimeric thereof, the detection probe oligomer target-hybridizing sequence is selected from SEQ ID NOs: 147, 156, 157, 160, and 161, including complements, DNA equivalents, and DNA/RNA chimerics thereof. In certain embodiments, the detection probe oligomer target-hybridizing sequence is (i) contained in the sequence of SEQ ID NO: 196 or its complement, or a DNA equivalent or DNA/RNA chimeric thereof, and (ii) includes a sequence selected from SEQ ID NO: 177 and SEQ ID NO: 178, including complements, DNA equivalents, and DNA/RNA chimerics thereof; in some such variations, the detection probe oligomer target-hybridizing sequence is selected from SEQ ID NOs: 131, 132, 135, 140, 147, 156, 157, 160, and 161, including complements, DNA equivalents, and DNA/RNA chimerics thereof.

In other embodiments of an oligomer combination as above further including at least one detection probe oligomer and where the at least two amplification oligomers comprise the amplification oligomers of (a') and (b'), the detection probe oligomer target-hybridizing sequence is at least about 13 nucleotides in length and is (i) contained in the sequence of SEQ ID NO: 189 or its complement, or a DNA equivalent or DNA/RNA chimeric thereof, and (ii) includes a sequence selected from SEQ ID NO: 190 and SEQ ID NO: 191, including complements, DNA equivalents, and DNA/RNA equivalents thereof. In some such variations, the detection probe oligomer target-hybridizing sequence is selected from the SEQ ID NOs: 125-130 and 143, including complements, DNA equivalents, and DNA/RNA chimerics thereof.

In particular variations of an oligomer combination as above further including at least one detection probe oligomer and where the at least two amplification oligomers comprise the amplification oligomers of (a) and (b), the amplification oligomer target-hybridizing sequence of (a), the amplification oligomer target-hybridizing sequence of (b), and the detection probe oligomer target-hybridizing sequence, respectively, are (A) SEQ ID NO: 30, SEQ ID NO: 82, and SEQ ID NO: 151 or its complement, or a DNA equivalent or DNA/RNA chimeric of SEQ ID NO: 151 or its complement; (B) SEQ ID NO: 30, SEQ ID NO: 82, and SEQ ID NO: 157 or its complement, or a DNA equivalent or DNA/RNA chimeric of SEQ ID NO: 157 or its complement; (C) SEQ ID NO: 33, SEQ ID NO: 82, and SEQ ID NO: 155 or its complement, or a DNA equivalent or DNA/RNA chimeric of SEQ ID NO: 155 or its complement; (D) SEQ ID NO: 49, SEQ ID NO: 82, and SEQ ID NO: 150 or its complement, or a DNA equivalent or DNA/RNA chimeric of SEQ ID NO: 150 or its complement; (E) SEQ ID NO: 49, SEQ ID NO: 82, and SEQ ID NO: 155 or its complement, or a DNA equivalent or DNA/RNA chimeric of SEQ ID NO: 155 or its complement; (F) SEQ ID NO: 21, SEQ ID NO: 89, and SEQ ID NO: 148 or its complement, or a DNA equivalent or DNA/RNA chimeric of SEQ ID NO: 148 or its complement; (G) SEQ ID NO: 21, SEQ ID NO: 89, and SEQ ID NO: 152 or its complement, or a DNA equivalent or DNA/RNA chimeric of SEQ ID NO: 152 or its complement; (H) SEQ ID NO: 30, SEQ ID NO: 89; and SEQ ID NO: 148 or its complement, or a DNA equivalent or DNA/RNA chimeric of SEQ ID NO: 148 or its complement; (I) SEQ ID NO: 30, SEQ ID NO: 89; and SEQ ID NO: 152 or its complement, or a DNA equivalent or DNA/RNA chimeric of SEQ ID NO: 152 or its complement; (I) SEQ ID NO: 33, SEQ ID NO: 89; and SEQ ID NO: 158 or its complement, or a DNA equivalent or DNA/RNA chimeric of SEQ ID NO: 158 or its complement; (K) SEQ ID NO: 49, SEQ ID NO: 89, and SEQ ID NO: 150 or its complement, or a DNA equivalent or DNA/RNA chimeric of SEQ ID NO: 150 or its complement; (L) SEQ ID NO: 21, SEQ ID NO: 92, and SEQ ID NO: 148 or its complement, or a DNA equivalent or DNA/RNA chimeric of SEQ ID NO: 148 or its complement; (M) SEQ ID NO: 21, SEQ ID NO: 92, and SEQ ID NO: 152 or its complement, or a DNA equivalent or DNA/RNA chimeric of SEQ ID NO: 152 or its complement; (N) SEQ ID NO: 30, SEQ ID NO: 92; and SEQ ID NO: 148 or its complement, or a DNA equivalent or DNA/RNA chimeric of SEQ ID NO: 148 or its complement; (O) SEQ ID NO: 30, SEQ ID NO: 92; and SEQ ID NO: 152 or its complement, or a DNA equivalent or DNA/RNA chimeric of SEQ ID NO: 152 or its complement; (P) SEQ ID NO: 21, SEQ ID NO: 94, and SEQ ID NO: 148 or its complement, or a DNA equivalent or DNA/RNA chimeric of SEQ ID NO: 148 or its complement; (Q) SEQ ID NO: 21, SEQ ID NO: 94, and SEQ ID NO: 152 or its complement, or a DNA equivalent or DNA/RNA chimeric of SEQ ID NO: 152 or its complement; (R) SEQ ID NO: 34, SEQ ID NO: 94, and SEQ ID NO: 148 or its complement, or a DNA equivalent or DNA/RNA chimeric of SEQ ID NO: 148 or its complement; (S) SEQ ID NO: 34, SEQ ID NO: 94, and SEQ ID NO: 152 or its complement, or a DNA equivalent or DNA/RNA chimeric of SEQ ID NO: 152 or its complement; (T) SEQ ID NO: 34, SEQ ID NO: 94, and SEQ ID NO: 157 or its complement, or a DNA equivalent or DNA/RNA chimeric of SEQ ID NO: 157 or its complement; (U) SEQ ID NO: 53, SEQ ID NO: 94, and SEQ ID NO: 148 or its complement, or a DNA equivalent or DNA/RNA chimeric of SEQ ID NO: 148 or its complement; (V) SEQ ID NO: 53, SEQ ID NO: 94, and SEQ ID NO: 152 or its complement, or a DNA equivalent or DNA/RNA chimeric of SEQ ID NO: 152 or its complement; (W) SEQ ID NO: 53, SEQ ID NO: 94, and SEQ ID NO: 157 or its complement, or a DNA equivalent or DNA/RNA chimeric of SEQ ID NO: 157 or its complement; (X) SEQ ID NO: 21, SEQ ID NO: 95, and SEQ ID NO: 148 or its complement, or a DNA equivalent or DNA/RNA chimeric of SEQ ID NO: 148 or its complement; (Y) SEQ ID NO: 21, SEQ ID NO: 95, and SEQ ID NO: 152 or its complement, or a DNA equivalent or DNA/RNA chimeric of SEQ ID NO: 152 or its complement; (Z) SEQ ID NO: 34, SEQ ID NO: 95, and SEQ ID NO: 148 or its complement, or a DNA equivalent or DNA/RNA chimeric of SEQ ID NO: 148 or its complement; (AA) SEQ ID NO: 34, SEQ ID NO: 95, and SEQ ID NO: 152 or its complement, or a DNA equivalent or DNA/RNA chimeric of SEQ ID NO: 152 or its complement; (AB) SEQ ID NO: 34, SEQ ID NO: 95, and SEQ ID NO: 157 or its complement, or a DNA equivalent or DNA/RNA chimeric of SEQ ID NO: 157 or its complement; (AC) SEQ ID NO: 53, SEQ ID NO: 95, and SEQ ID NO: 148 or its complement, or a DNA equivalent or DNA/RNA chimeric of SEQ ID NO: 148 or its complement; (AD) SEQ ID NO: 53, SEQ ID NO: 95, and SEQ ID NO: 152 or its complement, or a DNA equivalent or DNA/RNA chimeric of SEQ ID NO: 152 or its complement; or (AE) SEQ ID NO: 53, SEQ ID NO: 95, and SEQ ID NO: 157 or its complement, or a DNA equivalent or DNA/RNA chimeric of SEQ ID NO: 157 or its complement.

In particular variations of an oligomer combination as above further including at least one detection probe oligomer and where the at least two amplification oligomers comprise the amplification oligomers of (a') and (b'), the amplification oligomer target-hybridizing sequence of (a'), the amplification oligomer target-hybridizing sequence of (b'), and the detection probe oligomer target-hybridizing sequence, respectively, are (A) SEQ ID NO: 183, SEQ ID NO: 182, and SEQ ID NO: 126 or its complement, or a DNA equivalent or DNA/RNA chimeric of SEQ ID NO: 126 or its complement; (B) SEQ ID NO: 183, SEQ ID NO: 182, and SEQ ID NO: 127 or its complement, or a DNA equivalent or DNA/RNA chimeric of SEQ ID NO: 127 or its complement; (C) SEQ ID NO: 183, SEQ ID NO: 182, and SEQ ID NO: 128 or its complement, or a DNA equivalent or DNA/RNA chimeric of SEQ ID NO: 128 or its complement; (D)

SEQ ID NO: 183, SEQ ID NO: 182, and SEQ ID NO: 143 or its complement, or a DNA equivalent or DNA/RNA chimeric of SEQ ID NO: 143 or its complement; (E) SEQ ID NO: 183, SEQ ID NO: 182, and SEQ ID NO: 129 or its complement, or a DNA equivalent or DNA/RNA chimeric of SEQ ID NO: 129 or its complement; or (F) SEQ ID NO: 184, SEQ ID NO: 182, and SEQ ID NO: 126 or its complement, or a DNA equivalent or DNA/RNA chimeric of SEQ ID NO: 126 or its complement.

In some embodiments of an oligomer combination as above further including at least one detection probe oligomer, the detection probe oligomer comprises a 2' methoxy modification on at least one of a nucleotide residue member of the detection probe oligomer nucleotide sequence.

In some embodiments of an oligomer combination as above further including at least one detection probe oligomer, the detection probe oligomer further includes a detectable label such as, for example, a fluorescent or chemiluminescent label. A particularly suitable chemiluminescent label is a chemiluminescent acridinium ester (AE) compound linked between two nucleobases of the detection probe oligomer. In some embodiments comprising a detectably labeled probe oligomer, the detectable label is a fluorescent label and the detection probe oligomer further includes a non-fluorescent quencher; particularly suitable detection probe oligomers comprising a fluorescent label and a quencher including molecular torches, molecular beacons, and TaqMan detection probes.

In some embodiments of an oligomer combination as above further including at least one detection probe oligomer, the detection probe further includes a non-target-hybridizing sequence. In particular variations, a detection probe oligomer comprising a non-target-hybridizing sequence is a hairpin detection probe such as, e.g., a molecular beacon or a molecular torch.

In certain embodiments, an oligomer combination for detecting Plasmodium species nucleic acid in a sample as above includes at least two detection probe oligomers. In some such embodiments, the at least two detection probe oligomers comprise first and second detection probe oligomers, where (A) the first detection probe oligomer comprises a target-hybridizing sequence that is (i) contained in the sequence of SEQ ID NO: 197 or its complement, or a DNA equivalent or DNA/RNA chimeric thereof, and (ii) includes the sequence of SEQ ID NO: 175 or its complement, or a DNA equivalent or DNA/RNA chimeric thereof, and (B) the second detection probe oligomer comprises a target-hybridizing sequence that is (i) contained in the sequence of SEQ ID NO: 197 or its complement, or a DNA equivalent or DNA/RNA chimeric thereof, and (ii) includes the sequence of SEQ ID NO: 176 or its complement, or a DNA equivalent or DNA/RNA chimeric thereof. In a more specific variation, the first detection probe oligomer comprises the target-hybridizing sequence of SEQ ID NO: 157 or its complement, or a DNA equivalent or DNA/RNA chimeric thereof, and the second detection probe oligomer comprises a target-hybridizing sequence selected from SEQ ID NO: 148 and SEQ ID NO: 152, including complements, DNA equivalents, and DNA/RNA chimerics thereof.

In another aspect, the present invention provides use of a combination of at least two oligomers as above for specifically amplifying Plasmodium species nucleic acid in a sample.

In another aspect, the present invention provides a detection probe oligomer for specifically detecting a Plasmodium species target nucleic acid in a sample. In some embodiments, the detection probe oligomer comprises a target-hybridizing sequence that is from about 13 to about 40 nucleotides in length and configured to specifically hybridize to a target sequence contained within a *Plasmodium* species target region amplifiable by an oligomer combination comprising first and second *Plasmodium*-specific amplification oligomers, where (a) the first amplification oligomer comprises a target-hybridizing sequence (i) that is from about 14 to about 20 contiguous nucleotides in length, is contained in the sequence of SEQ ID NO: 162, and includes the sequence of SEQ ID NO: 163, or (ii) that is from about 14 to about 25 contiguous nucleotides in length, is contained in the sequence of SEQ ID NO: 166, and includes the sequence of SEQ ID NO: 167 or SEQ ID NO: 168; and (b) the second amplification oligomer comprises a target-hybridizing sequence that is from about 15 to about 33 contiguous nucleotides in length, is contained in SEQ ID NO: 169 and includes the sequence of SEQ ID NO: 171, SEQ ID NO: 172, or SEQ ID NO: 173. In some such embodiments, the detection probe oligomer target-hybridizing sequence is (i) contained in the sequence of SEQ ID NO: 196 or its complement, or a DNA equivalent or DNA/RNA chimeric thereof, and (ii) includes a sequence selected from SEQ ID NO: 175, SEQ ID NO: 176, SEQ ID NO: 177, and SEQ ID NO: 178, including complements, DNA equivalents, and DNA/RNA equivalents thereof. Suitable detection probe oligomer target-hybridizing sequences include SEQ ID NOs: 131, 132, 135, 140, 145, 147-157, and 159-161, including complements, DNA equivalents, and DNA/RNA chimerics thereof. In certain embodiments, the detection probe oligomer target-hybridizing sequence is (i) contained in the sequence of SEQ ID NO: 197 or its complement, or a DNA equivalent or DNA/RNA chimeric thereof, and (ii) includes the sequence of SEQ ID NO: 174 or SEQ ID NO: 175, including complements, DNA equivalents, and DNA/RNA chimerics thereof; in some such variations comprising the sequence of SEQ ID NO: 174 or its complement, or a DNA equivalent or DNA/RNA chimeric thereof, the detection probe oligomer target-hybridizing sequence is selected from SEQ ID NOs: 148-155 and 159, including complements, DNA equivalents, and DNA/RNA chimerics thereof, in other such variations comprising SEQ ID NO: 175 or its complement, or a DNA equivalent or DNA/RNA chimeric thereof, the detection probe oligomer target-hybridizing sequence is selected from SEQ ID NOs: 147, 156, 157, 160, and 161, including complements, DNA equivalents, and DNA/RNA chimerics thereof. In certain embodiments, the detection probe oligomer target-hybridizing sequence is (i) contained in the sequence of SEQ ID NO: 196 or its complement, or a DNA equivalent or DNA/RNA chimeric thereof, and (ii) includes a sequence selected from SEQ ID NO: 177 and SEQ ID NO: 178, including complements, DNA equivalents, and DNA/RNA chimerics thereof; in some such variations, the detection probe oligomer target-hybridizing sequence is selected from SEQ ID NOs: 131, 132, 135, 140, 147, 156, 157, 160, and 161, including complements, DNA equivalents, and DNA/RNA chimerics thereof.

In other embodiments of a detection probe oligomer for specifically detecting a *Plasmodium* species target nucleic acid in a sample, the detection probe oligomer comprises a target-hybridizing sequence that is at least about 13 nucleotides in length and configured to specifically hybridize to a target sequence contained within a *Plasmodium* species target region amplifiable by an oligomer combination comprising first and second *Plasmodium*-specific amplification oligomers, where (a) the first amplification oligomer comprises a target-hybridizing sequence that is contained in the sequence of SEQ ID NO: 185 and includes the sequence of SEQ ID NO: 37, SEQ ID NO: 46, or SEQ ID NO: 187; and (b) the second amplification oligomer comprises a target-hybridizing sequence that is contained in SEQ ID NO: 188 and includes the sequence of SEQ ID NO: 83, SEQ ID NO: 84, or SEQ ID NO: 182. In some such embodiments, the detection probe oligomer target-hybridizing sequence is (i) contained in the sequence of SEQ ID NO: 189 or its complement, or a DNA equivalent or DNA/RNA chimeric thereof, and (ii) includes a sequence selected from SEQ ID NO: 190 and SEQ ID NO: 191, including complements, DNA equivalents, and DNA/RNA equivalents thereof. In more specific variations, the detection probe oligomer target-hybridizing sequence is selected from the SEQ ID NOs: 125-130 and 143, including complements, DNA equivalents, and DNA/RNA chimerics thereof.

In some embodiments of a detection probe oligomer as above, the detection probe oligomer comprises a 2' methoxy modification on at least one of a nucleotide residue member of the detection probe oligomer nucleotide sequence.

In some embodiments of a detection probe oligomer as above, the detection probe oligomer further includes a detectable label such as, for example, a fluorescent or chemiluminescent label. A particularly suitable chemiluminescent label is a chemiluminescent acridinium ester (AE) compound linked between two nucleobases of the detection probe oligomer. In some embodiments comprising a detectable label, the detectable label is a fluorescent label and the detection probe oligomer further includes a non-fluorescent quencher; particularly suitable detection probe oligomers comprising a fluorescent label and a quencher including molecular torches, molecular beacons, and TaqMan detection probes.

In some embodiments of a detection probe oligomer as above, the detection probe further includes a non-target-hybridizing sequence. In particular variations, a detection probe oligomer comprising a non-target-hybridizing sequence is a hairpin detection probe such as, e.g., a molecular beacon or a molecular torch.

In another aspect, the present invention provides a combination of at least two oligomers for detecting a *Plasmodium* species target nucleic acid in a sample, the oligomer combination comprising at least two detection probe oligomers as above. In some embodiments, the at least two detection probe oligomers comprise a (A) a first detection probe oligomer comprising a target-hybridizing sequence that (i) is contained in the sequence of SEQ ID NO: 197 or its complement, or a DNA equivalent or DNA/RNA chimeric thereof, and (ii) includes the sequence of SEQ ID NO: 175 or its complement, or a DNA equivalent or DNA/RNA chimeric thereof, and (B) a second detection probe oligomer comprising a target-hybridizing sequence that (i) is contained in the sequence of SEQ ID NO: 197 or its complement, or a DNA equivalent or DNA/RNA chimeric thereof, and (ii) includes the sequence of SEQ ID NO: 176 or its complement, or a DNA equivalent or DNA/RNA chimeric thereof. In more specific variations, the first detection probe oligomer comprises the target-hybridizing sequence of SEQ ID NO: 157 or its complement, or a DNA equivalent or DNA/RNA chimeric thereof, and the second detection probe oligomer comprises a target-hybridizing sequence selected from SEQ ID NO: 148 and SEQ ID NO: 152, including complements, DNA equivalents, and DNA/RNA chimerics thereof.

In another aspect, the present invention provides use of a detection probe oligomer or oligomer combination according as above for specifically detecting *Plasmodium* species nucleic acid in a sample.

In another aspect, the present invention provides a capture probe oligomer for specifically isolating *Plasmodium* species nucleic acid from a sample. In some embodiments, the capture probe oligomer comprises a target-hybridizing sequence covalently attached to a sequence or moiety that binds to an immobilized probe, where the target-hybridizing sequence is up to about 30 contiguous nucleotides in length and includes a sequence selected from SEQ ID NOs: 11-15, 17, 19, and 20, including DNA equivalents and DNA/RNA chimerics thereof. In more specification variations, the capture probe oligomer target-hybridizing sequence is selected from SEQ ID NOs: 11-15, 17, 19, and 20, including DNA equivalents and DNA/RNA chimerics thereof.

In another aspect, the present invention provides a combination of at least two oligomers for specifically isolating *Plasmodium* species nucleic acid from a sample, the oligomer combination comprising at least two capture probe oligomers as above. In some embodiments, the at least two capture probe oligomers comprise a first capture probe oligomer comprising the target-hybridizing sequence of SEQ ID NO: 19, or a DNA equivalent or DNA/RNA chimeric thereof, and a second capture probe oligomer comprising the target-hybridizing sequence of SEQ ID NO: 20, or a DNA equivalent or DNA/RNA chimeric thereof.

In another aspect, the present invention provides use of a capture probe oligomer or oligomer combination as above for specifically capturing *Plasmodium* species nucleic acid from a sample.

In another aspect, the present invention provides a kit comprising a combination of at least two oligomers as above.

In another aspect, the present invention a reaction mixture comprising a combination of at least two oligomers as above.

These and other aspects of the invention will become evident upon reference to the following detailed description of the invention and the attached drawings.

Definitions

Unless defined otherwise, all technical and scientific terms used herein have the same meaning as commonly understood by one of ordinary skill in the art pertinent to the methods and compositions described. As used herein, the following terms and phrases have the meanings ascribed to them unless specified otherwise.

The terms "a," "an," and "the" include plural referents, unless the context clearly indicates otherwise.

"Sample" includes any specimen that may contain, or is suspected of containing, *Plasmodium* species or components thereof, such as nucleic acids or fragments of *Plasmodium* nucleic acids. The sample may be an isolated sample. Samples include "biological samples" which include any tissue or material derived from a living or dead human that may contain the *Plasmodium* parasite or components thereof (e.g., a target nucleic acid derived therefrom), including, e.g., blood, peripheral blood and red blood cells. The use of other sample types that may contain the *Plasmodium* parasite or components thereof (e.g., a target nucleic acid derived therefrom)—such as plasma, serum, lymph node, gastrointestinal tissue, faeces, urine, semen or other body fluids or materials—is also contemplated. The biological sample may be treated to physically or mechanically disrupt tissue or cell structure, thus releasing intracellular components into a solution which may further contain enzymes, buffers, salts, detergents and the like, which are used to prepare, using standard methods, a biological sample for analysis. For example, a sample may be treated with cell lysis reagent such as, e.g., a lysis reagent as described in U.S. Pat. No. 10,093,989 or PCT Pub. No. WO 2017/189746, each incorporated by reference herein. Also, samples may include processed samples, such as those obtained from passing samples over or through a filtering device, or following centrifugation, or by adherence to a medium, matrix, or support.

"Nucleic acid" refers to a multimeric compound comprising two or more covalently bonded nucleosides or nucleoside analogs having nitrogenous heterocyclic bases, or base analogs, where the nucleosides are linked together by phosphodiester bonds or other linkages to form a polynucleotide. Nucleic acids include RNA, DNA, or chimeric DNA-RNA polymers or oligonucleotides, and analogs thereof. A nucleic acid "backbone" may be made up of a variety of linkages, including one or more of sugar-phosphodiester linkages, peptide-nucleic acid bonds (in "peptide nucleic acids" or PNAs, see PCT Pub. No. WO 95/32305), phosphorothioate linkages, methylphosphonate linkages, or combinations thereof. Sugar moieties of the nucleic acid may be either ribose or deoxyribose, or similar compounds having known substitutions, e.g., 2' methoxy substitutions and 2' halide substitutions (e.g., 2'-F). Nitrogenous bases may be conventional bases (A, G, C, T, U), analogs thereof (e.g., inosine, 5-methylisocytosine, isoguanine; The Biochemistry of the Nucleic Acids 5-36, Adams et al., ed., 11th ed., 1992, *BioTechniques* (2007) 43:617-24), which include derivatives of purine or pyrimidine bases (e.g., N4-methyl deoxyguanosine, deaza- or aza-purines, deaza- or aza-pyrimidines, pyrimidine bases having substituent groups at the 5 or 6 position, purine bases having an altered or replacement substituent at the 2, 6 and/or 8 position, such as 2-amino-6-methylaminopurine, 06-methylguanine, 4-thio-pyrimidines, 4-amino-pyrimidines, 4-dimethylhydrazine-pyrimidines, and 04-alkyl-pyrimidines, and pyrazolo-compounds, such as unsubstituted or 3-substituted pyrazolo[3,4-d]pyrimidine; U.S. Pat. Nos. 5,378,825, 6,949,367 and PCT Pub. No. WO 93/13121). Nucleic acids may include "abasic" residues in which the backbone does not include a nitrogenous base for one or more residues (U.S. Pat. No. 5,585,481). A nucleic acid may comprise only conventional sugars, bases, and linkages as found in RNA and DNA, or may include conventional components and substitutions (e.g., conventional bases linked by a 2' methoxy backbone, or a nucleic acid including a mixture of conventional bases and one or more base analogs). Nucleic acids may include "locked nucleic acids" (LNA), in which one or more nucleotide monomers have a bicyclic furanose unit locked in an RNA mimicking sugar conformation, which enhances hybridization affinity toward complementary sequences in single-stranded RNA (ssRNA), single-stranded DNA (ssDNA), or double-stranded DNA (dsDNA) (*Biochemistry* (2004) 43:13233-41). Nucleic acids may include modified bases to alter the function or behavior of the nucleic acid, e.g., addition of a 3'-terminal dideoxynucleotide to block additional nucleotides from being added to the nucleic acid. Synthetic methods for making nucleic acids in vitro are well-known in the art.

The term "polynucleotide," as used herein, denotes a nucleic acid chain. Throughout this application, nucleic acids are designated by the 5'-terminus to the 3'-terminus. Standard nucleic acids, e.g., DNA and RNA, are typically synthesized "5'-to-3'," i.e., by the addition of nucleotides to the 3'-terminus of a growing nucleic acid.

A "nucleotide," as used herein, is a subunit of a nucleic acid consisting of a phosphate group, a 5-carbon sugar and a nitrogenous base. The 5-carbon sugar found in RNA is ribose. In DNA, the 5-carbon sugar is 2'-deoxyribose. The term also includes analogs of such subunits, such as a methoxy group at the 2' position of the ribose (2'-O-Me).

A "nucleic-acid-based detection assay," as used herein, is an assay for the detection of a target sequence within a target nucleic acid and utilizing one more oligonucleotides that specifically hybridize to the target sequence.

In certain embodiments, a nucleic-acid-based detection assay is an "amplification-based assay," i.e., an assay that utilizes one or more steps for amplifying a nucleic acid target sequence. Various amplification methods for use in detection assays are known in the art, several of which are summarized further herein. For the sake of clarity, an amplification-based assay may include one or more steps that do not amplify a target sequence, such as, for example, steps used in non-amplification-based assay methods (e.g., a hybridization assay or a cleavage-based assay).

In other embodiments, a nucleic-acid-based detection assay is a "non-amplification-based assay," i.e., an assay that does not rely on any step for amplifying a nucleic acid target sequence. For the sake of clarity, a nucleic-acid-based detection assay that includes a reaction for extension of a primer in the absence of any corresponding downstream amplification oligomer (e.g., extension of a primer by a reverse transcriptase to generate an RNA:DNA duplex followed by an RNase digestion of the RNA, resulting in a single-stranded cDNA complementary to an RNA target but without generating copies of the cDNA) is understood to be a non-amplification-based assay.

An exemplary non-amplification-based assay is a "cleavage-based assay," which is an assay that relies on the specific cleavage, by a flap endonuclease, of a linear duplex cleavage structure formed by the specific hybridization of overlapping oligonucleotides to a target nucleic acid. In these assays, a probe oligonucleotide containing a non-target-hybridizing flap region is cleaved in an overlap-dependent manner by the flap endonuclease to release a cleavage product that is then detected. The principles of cleavage-based assays are well-known in the art, and exemplary assays are described in, for example, *Nat. Biotechnol.* (1999) 17:292-296, *Mol. Diagn.* (1999) 4: 135-144, *J. Clin. Microbiol.* (2006) 44:3443-3447, and U.S. Pat. Nos. 5,846,717, 6,706,471 and 5,614,402. Cleavage-based assays include, e.g., the commercially available Invader® assays (Hologic, Inc., Madison, WI).

A "target nucleic acid," as used herein, is a nucleic acid comprising a target sequence to be detected. Target nucleic acids may be DNA or RNA as described herein, and may be either single-stranded or double-stranded. The target nucleic acid may include other sequences besides the target sequence.

By "isolated" it is meant that a sample containing a target nucleic acid is taken from its natural milieu, but the term does not connote any degree of purification.

The term "target sequence," as used herein, refers to the particular nucleotide sequence of a target nucleic acid that is to be detected. The "target sequence" includes the complexing sequences to which oligonucleotides (e.g., probe oligonucleotide, priming oligonucleotides and/or promoter oligonucleotides) complex during a detection process (e.g., an amplification-based detection assay such as, for example, TMA or PCR, or a non-amplification-based detection assay such as, for example, a cleavage-based assay). Where the target nucleic acid is originally single-stranded, the term "target sequence" will also refer to the sequence complementary to the "target sequence" as present in the target nucleic acid. Where the target nucleic acid is originally double-stranded, the term "target sequence" refers to both the sense (+) and antisense (−) strands. In choosing a target sequence, the skilled artisan will understand that a "unique" sequence should be chosen so as to distinguish between unrelated or closely related target nucleic acids.

"Target-hybridizing sequence" is used herein to refer to the portion of an oligomer that is configured to hybridize with a target nucleic acid sequence. Preferably, the target-hybridizing sequences are configured to specifically hybridize with a target nucleic acid sequence. Target-hybridizing sequences may be 100% complementary to the portion of the target sequence to which they are configured to hybridize, but not necessarily. Target-hybridizing sequences may also include inserted, deleted and/or substituted nucleotide residues relative to a target sequence. Less than 100% complementarity of a target-hybridizing sequence to a target sequence may arise, for example, when the target nucleic acid is a plurality strains within a species, such as would be the case for an oligomer configured to hybridize to the various strains of *Plasmodium*. It is understood that other reasons exist for configuring a target-hybridizing sequence to have less than 100% complementarity to a target nucleic acid.

The term "targets a sequence," as used herein in reference to a region of *Plasmodium* sp. nucleic acid, refers to a process whereby an oligonucleotide hybridizes to the target sequence in a manner that allows for detection as described herein. In one embodiment, the oligonucleotide is complementary with the targeted *Plasmodium* sp. nucleic acid sequence and contains no mismatches. In another embodiment, the oligonucleotide is complementary but contains 1, 2, 3, 4, or 5 mismatches with the targeted *Plasmodium* sp. nucleic acid sequence. Preferably, the oligonucleotide that hybridizes to the target nucleic acid sequence includes at least 10 to as many as 50 nucleotides complementary to the target sequence. It is understood that at least 10 and as many as 50 is an inclusive range such that 10, 50 and each whole number there between are included. Preferably, the oligomer specifically hybridizes to the target sequence.

The term "configured to" denotes an actual arrangement of the polynucleotide sequence configuration of a referenced oligonucleotide target-hybridizing sequence. For example, oligonucleotides that are configured to specifically hybridize to a target sequence have a polynucleotide sequence that specifically hybridizes to the referenced sequence under stringent hybridization conditions.

The term "configured to specifically hybridize to" as used herein means that the target-hybridizing region of an oligonucleotide is designed to have a polynucleotide sequence that could target a sequence of the referenced *Plasmodium* sp. target region. Such an oligonucleotide is not limited to targeting that sequence only, but is rather useful as a composition, in a kit or in a method for targeting a *Plasmodium* sp. target nucleic acid. The oligonucleotide is designed to function as a component of an assay for detection of *Plasmodium* sp. from a sample, and therefore is designed to target *Plasmodium* sp. in the presence of other nucleic acids commonly found in testing samples. "Specifically hybridize to" does not mean exclusively hybridize to, as some small level of hybridization to non-target nucleic acids may occur, as is understood in the art. Rather, "specifically hybridize to" means that the oligonucleotide is configured to function in an assay to primarily hybridize the target so that an accurate detection of target nucleic acid in a sample can be determined. The term "configured to" denotes an actual arrangement of the polynucleotide sequence configuration of the oligonucleotide target-hybridizing sequence.

The term "fragment," as used herein in reference to a *Plasmodium* sp. targeted nucleic acid, refers to a piece of contiguous nucleic acid.

The term "region," as used herein, refers to a portion of a nucleic acid wherein the portion is smaller than the entire nucleic acid. For example, when the nucleic acid in reference is an oligonucleotide promoter primer, the term "region" may be used refer to the smaller promoter portion of the entire oligonucleotide. As a non-limiting example, when the nucleic acid in reference is an amplicon, the term region may be used to refer to the smaller nucleotide sequence identified for hybridization by the target-hybridizing sequence of a probe.

The interchangeable terms "oligomer," "oligo," and "oligonucleotide" refer to a nucleic acid having generally less than 1,000 nucleotide (nt) residues, including polymers in a range having a lower limit of about 5 nt residues and an upper limit of about 500 to 900 nt residues. In some embodiments, oligonucleotides are in a size range having a lower limit of about 12 to 15 nt and an upper limit of about 50 to 600 nt, and other embodiments are in a range having a lower limit of about 15 to 20 nt and an upper limit of about 22 to 100 nt. Oligonucleotides may be purified from naturally occurring sources or may be synthesized using any of a variety of well-known enzymatic or chemical methods. The term oligonucleotide does not denote any particular function to the reagent; rather, it is used generically to cover all such reagents described herein. An oligonucleotide may serve various different functions. For example, it may function as a primer if it is specific for and capable of hybridizing to a complementary strand and can further be extended in the presence of a nucleic acid polymerase; it may function as a primer and provide a promoter if it contains a sequence recognized by an RNA polymerase and allows for transcription (e.g., a T7 Primer); and it may function to detect a target nucleic acid if it is capable of hybridizing to the target nucleic acid, or an amplicon thereof, and further provides a detectible moiety (e.g., an acridinium-ester compound).

As used herein, an oligonucleotide can "substantially correspond to" a specified reference nucleic acid sequence, which means that the oligonucleotide is sufficiently similar to the reference nucleic acid sequence such that the oligonucleotide has similar hybridization properties to the reference nucleic acid sequence in that it would hybridize with the same target nucleic acid sequence under stringent hybridization conditions. One skilled in the art will understand that "substantially corresponding oligonucleotides" can vary from a reference sequence and still hybridize to the same target nucleic acid sequence. It is also understood that a first nucleic acid corresponding to a second nucleic acid includes the RNA and DNA thereof and includes the complements thereof, unless the context clearly dictates otherwise. This variation from the nucleic acid may be stated in terms of a percentage of identical bases within the sequence or the percentage of perfectly complementary bases between the probe or primer and its target sequence. Thus, in certain embodiments, an oligonucleotide "substantially corresponds" to a reference nucleic acid sequence if these percentages of base identity or complementarity are from 100% to about 80%. In preferred embodiments, the percentage is from 100% to about 85%. In more preferred embodiments, this percentage is from 100% to about 90%;

in other preferred embodiments, this percentage is from 100% to about 95%. Similarly, a region of a nucleic acid or amplified nucleic acid can be referred to herein as corresponding to a reference nucleic acid sequence. One skilled in the art will understand the various modifications to the hybridization conditions that might be required at various percentages of complementarity to allow hybridization to a specific target sequence without causing an unacceptable level of non-specific hybridization.

Exemplary sequences for *Plasmodium* sp. target nucleic acid are shown in Table 19, infra. Specifically, SEQ ID NOs: 180 and 192-195 are reference sequences corresponding to ribosomal RNA sequences for *Plasmodium falciparum, Plasmodium vivax, Plasmodium knowlesi, Plasmodium ovale,* and *Plasmodium malariae,* respectively. Where a target region of *Plasmodium* sp. is described herein as "corresponding to" a defined region of SEQ ID NO: 180, it is understood that such reference includes homologous regions of any one or more of SEQ ID NOs: 192-195. It is also understood that such reference to a region "corresponding to" a defined region of SEQ ID NO: 180 includes homologous regions of naturally occurring variants of any one or more of SEQ ID NOs: 180 and 192-195 that may be present in a sample.

An "amplification oligomer" is an oligomer at least the 3'-end of which is complementary to a target nucleic acid and which hybridizes to a target nucleic acid, or its complement, and participates in a nucleic acid amplification reaction. An example of an amplification oligomer is a "primer" that hybridizes to a target nucleic acid and contains a 3' OH end that is extended by a polymerase in an amplification process. Another example of an amplification oligomer is an oligomer that is not extended by a polymerase (e.g., because it has a 3' blocked end) but participates in or facilitates amplification. For example, the 5' region of an amplification oligonucleotide may include a promoter sequence that is non-complementary to the target nucleic acid (which may be referred to as a "promoter primer" or "promoter provider"). Those skilled in the art will understand that an amplification oligomer that functions as a primer may be modified to include a 5' promoter sequence, and thus function as a promoter primer. Incorporating a 3' blocked end further modifies the promoter primer, which is now capable of hybridizing to a target nucleic acid and providing an upstream promoter sequence that serves to initiate transcription, but does not provide a primer for oligo extension. Such a modified oligo is referred to herein as a "promoter provider" oligomer. Size ranges for amplification oligonucleotides include those that are about 10 to about 70 nt long (not including any promoter sequence or poly-A tails) and contain at least about 10 contiguous bases, or even at least 12 contiguous bases that are complementary to a region of the target nucleic acid sequence (or a complementary strand thereof). The contiguous bases are at least 80%, or at least 90%, or completely complementary to the target sequence to which the amplification oligomer binds. An amplification oligomer may optionally include modified nucleotides or analogs, or additional nucleotides that participate in an amplification reaction but are not complementary to or contained in the target nucleic acid, or template sequence. It is understood that when referring to ranges for the length of an oligonucleotide, amplicon, or other nucleic acid, that the range is inclusive of all whole numbers (e.g., 19-25 contiguous nucleotides in length includes 19, 20, 21, 22, 23, 24 & 25).

As used herein, a "promoter" is a specific nucleic acid sequence that is recognized by a DNA-dependent RNA polymerase ("transcriptase") as a signal to bind to the nucleic acid and begin the transcription of RNA at a specific site.

As used herein, a "promoter provider" or "provider" refers to an oligonucleotide comprising first and second regions and which is modified to prevent the initiation of DNA synthesis from its 3'-terminus. The "first region" of a promoter provider oligonucleotide comprises a base sequence which hybridizes to a DNA template, where the hybridizing sequence is situated 3', but not necessarily adjacent to, a promoter region. The hybridizing portion of a promoter oligonucleotide is typically at least 10 nucleotides in length and may extend up to 50 or more nucleotides in length. The "second region" comprises a promoter sequence for an RNA polymerase. A promoter oligonucleotide is engineered so that it is incapable of being extended by an RNA- or DNA-dependent DNA polymerase, e.g., reverse transcriptase, preferably comprising a blocking moiety at its 3'-terminus as described above. As referred to herein, a "T7 Provider" is a blocked promoter provider oligonucleotide that provides an oligonucleotide sequence that is recognized by T7 RNA polymerase.

"Amplification" refers to any known procedure for obtaining multiple copies of a target nucleic acid sequence or its complement or fragments thereof. The multiple copies may be referred to as amplicons or amplification products. Known amplification methods include both thermal cycling and isothermal amplification methods. In some embodiments, isothermal amplification methods are preferred. Replicase-mediated amplification, polymerase chain reaction (PCR), ligase chain reaction (LCR), strand-displacement amplification (SDA), and transcription-mediated or transcription-associated amplification are non-limiting examples of nucleic acid amplification methods. Replicase-mediated amplification uses self-replicating RNA molecules, and a replicase such as QB-replicase (e.g., U.S. Pat. No. 4,786,600). PCR amplification uses a DNA polymerase, pairs of primers, and thermal cycling to synthesize multiple copies of two complementary strands of dsDNA or from a cDNA (e.g., U.S. Pat. Nos. 4,683,195, 4,683,202, and 4,800, 159). LCR amplification uses four or more different oligonucleotides to amplify a target and its complementary strand by using multiple cycles of hybridization, ligation, and denaturation (e.g., U.S. Pat. Nos. 5,427,930 and 5,516,663). SDA uses a primer that contains a recognition site for a restriction endonuclease and an endonuclease that nicks one strand of a hemimodified DNA duplex that includes the target sequence, whereby amplification occurs in a series of primer extension and strand displacement steps (e.g., U.S. Pat. Nos. 5,422,252, 5,547,861 and U.S. Pat. No. 5,648, 211). Preferred embodiments use an amplification method suitable for the amplification of RNA target nucleic acids, such as transcription-mediated amplification (TMA) or NASBA, but it will be apparent to persons of ordinary skill in the art that oligomers disclosed herein may be readily used as primers in other amplification methods.

"Transcription-associated amplification," also referred to herein as "transcription-mediated amplification" (TMA), refers to nucleic acid amplification that uses an RNA polymerase to produce multiple RNA transcripts from a nucleic acid template. These methods generally employ an RNA polymerase, a DNA polymerase, deoxyribonucleoside triphosphates, ribonucleoside triphosphates, and a template complementary oligonucleotide that includes a promoter sequence, and optionally may include one or more other oligonucleotides. TMA methods are embodiments of amplification methods used for amplifying and detecting *Plasmo-*

*dium* target sequences as described herein. Variations of transcription-associated amplification are well-known in the art as previously disclosed in detail (e.g., U.S. Pat. Nos. 4,868,105, 5,124,246, 5,130,238, 5,437,990, 5,554,516 and 7,374,885 and PCT Pub. Nos. WO 88/01302, WO 88/10315, and WO 95/03430). The person of ordinary skill in the art will appreciate that the disclosed compositions may be used in amplification methods based on extension of oligomer sequences by a polymerase.

As used herein, the term "real-time TMA" refers to transcription-mediated amplification ("TMA") of target nucleic acid that is monitored by real-time detection means.

The term "amplicon," which is used interchangeably with "amplification product," refers to the nucleic acid molecule generated during an amplification procedure that is complementary or homologous to a sequence contained within the target sequence. These terms can be used to refer to a single strand amplification product, a double strand amplification product, or one of the strands of a double strand amplification product.

"Probe," "detection probe," "detection oligonucleotide," and "detection probe oligomer" are used interchangeably herein to refer to a nucleic acid oligomer that hybridizes specifically to a target sequence in a nucleic acid, or in an amplified nucleic acid, under conditions that promote hybridization to allow detection of the target sequence or amplified nucleic acid. Detection may either be direct (e.g., a probe hybridized directly to its target sequence) or indirect (e.g., a probe linked to its target via an intermediate molecular structure). Probes may be DNA, RNA, analogs thereof, or combinations thereof and they may be labeled or unlabeled. A probe's "target sequence" generally refers to a smaller nucleic acid sequence within a larger nucleic acid sequence that hybridizes specifically to at least a portion of a probe oligomer by standard base pairing. A probe may comprise target-specific sequences and other sequences that contribute to the three-dimensional conformation of the probe (e.g., U.S. Pat. Nos. 5,118,801, 5,312,728, 6,849,412, 6,835,542, 6,534,274 and 6,361,945; and US Pub. No. 20060068417). In a preferred embodiment, the detection probe comprises a 2' methoxy backbone, which can result in a higher signal being obtained.

The term "TaqMan® probe" refers to detection oligonucleotides that contain a fluorescent dye, typically on the 5' base, and a non-fluorescent quenching dye (quencher), typically on the 3' base. When irradiated, the excited fluorescent dye transfers energy to the nearby quenching dye molecule rather than fluorescing, resulting in a non-fluorescent substrate. During amplification, the exonuclease activity of the polymerase cleaves the TaqMan probe to separate the fluorophore from the quencher, thereby allowing an unquenched signal to be emitted from the fluorophore as an indicator of amplification.

As used herein, a "label" refers to a moiety or compound joined directly or indirectly to a probe that is detected or leads to a detectable signal. Direct labeling can occur through bonds or interactions that link the label to the probe, including covalent bonds or non-covalent interactions, e.g., hydrogen bonds, hydrophobic and ionic interactions, or formation of chelates or coordination complexes. Indirect labeling can occur through use of a bridging moiety or "linker" such as a binding pair member, an antibody or additional oligomer, which is either directly or indirectly labeled, and which may amplify the detectable signal. Labels include any detectable moiety, such as a radionuclide, ligand (e.g., biotin, avidin), enzyme or enzyme substrate, reactive group, or chromophore (e.g., dye, particle, or bead that imparts detectable color), luminescent compound (e.g., bioluminescent, phosphorescent, or chemiluminescent labels), or fluorophore. Labels may be detectable in a homogeneous assay in which bound labeled probe in a mixture exhibits a detectable change different from that of an unbound labeled probe, e.g., instability or differential degradation properties. A "homogeneous detectable label" can be detected without physically removing bound from unbound forms of the label or labeled probe (e.g., U.S. Pat. Nos. 5,283,174, 5,656,207, and 5,658,737). Labels include chemiluminescent compounds, e.g., acridinium ester ("AE") compounds that include standard AE and derivatives (e.g., U.S. Pat. Nos. 5,656,207, 5,658,737, and 5,639,604). Synthesis and methods of attaching labels to nucleic acids and detecting labels are well known (e.g., Sambrook et al., Molecular Cloning, A Laboratory Manual, 2nd ed. (Cold Spring Harbor Laboratory Press, Cold Spring Harbor, NY, 1989), Chapter 10; U.S. Pat. Nos. 5,658,737, 5,656,207, 5,547,842, 5,283,174, and 4,581,333). More than one label, and more than one type of label, may be present on a particular probe, or detection may use a mixture of probes in which each probe is labeled with a compound that produces a detectable signal (e.g., U.S. Pat. Nos. 6,180,340 and 6,350,579).

As used herein, structures referred to as "molecular torches" are designed to include distinct regions of self-complementarity ("the closing domain") which are connected by a joining region ("the target-binding domain") and which hybridize to one another under predetermined hybridization assay conditions. All or part of the nucleotide sequences comprising closing domains may also function as target-binding domains. Thus, closing domains can include target-binding sequences, non-target binding sequences, and combinations thereof.

As used herein, structures referred to as "molecular beacons" are designed to include a target-binding sequence flanked on both its 5' and 3' ends by sequences that are complementary to each other and which hybridize to each other under predetermined hybridization assay conditions. The flanking, complementary regions may be referred to as "switch sequences."

"Capture probe," "capture oligonucleotide," "target capture oligonucleotide," and "capture probe oligomer" are used interchangeably herein to refer to a nucleic acid oligomer that specifically hybridizes to a target sequence in a target nucleic acid by standard base pairing and joins to a binding partner on an immobilized probe to capture the target nucleic acid to a support. One example of a capture oligomer includes an oligonucleotide comprising two binding regions: a target hybridizing sequence and an immobilized probe-binding region. A variation of this example, the two regions may be present on two different oligomers joined together by one or more linkers. In another embodiment of a capture oligomer, the target-hybridizing sequence is a sequence that includes random or non-random poly-GU, poly-GT, or poly U sequences to bind non-specifically to a target nucleic acid and link it to an immobilized probe on a support (see, e.g., PCT Pub. No. WO 2008/016988). The immobilized probe-binding region can be a nucleic acid sequence, referred to as a tail. Tails include a substantially homopolymeric tail of about 10 to 40 nucleotides (e.g., A10 to A40), or of about 17 to 33 nt (e.g., T3A14 to T3A30), that bind to a complementary immobilized sequence attached to the support particle or support matrix. Thus, a non-limiting example of preferred nucleic acid tails can in some embodiments include $T_{0-4}A_{10-40}$ sequences. Another example of a capture oligomer comprises two regions, a target-hybridizing sequence and a binding pair member that is not a nucleic acid sequence.

As used herein, an "immobilized oligonucleotide," "immobilized probe," or "immobilized nucleic acid" refers to a nucleic acid binding partner that joins a capture oligomer to a support, directly or indirectly. An immobilized probe joined to a support facilitates separation of a capture probe bound target from unbound material in a sample. One embodiment of an immobilized probe is an oligomer joined to a support that facilitates separation of bound target sequence from unbound material in a sample. Supports may include known materials, such as matrices and particles free in solution, which may be made of nitrocellulose, nylon, glass, polyacrylate, mixed polymers, polystyrene, silane, polypropylene, metal, or other compositions, of which one embodiment is magnetically attractable particles. Supports may be monodisperse magnetic spheres (e.g., uniform size+ 5%), to which an immobilized probe is joined directly (via covalent linkage, chelation, or ionic interaction), or indirectly (via one or more linkers), where the linkage or interaction between the probe and support is stable during hybridization conditions.

DESCRIPTION

The present invention is generally directed to methods and compositions for determining the presence or absence of the protozoan parasite *Plasmodium* sp. in a sample, such as, e.g., a blood sample. Suitably, the methods and compositions described herein are able to detect the presence or absence of *Plasmodium falciparum, Plasmodium knowlesi, Plasmodium malariae, Plasmodium ovale* and/or *Plasmodium vivax*. In some embodiments, the present invention provides methods for the detection of *Plasmodium* sp. in a sample, where the method includes performing amplification-based detection of a target nucleic from *Plasmodium* sp. The present invention further provides compositions (including reaction mixtures) and kits comprising a combination of oligomers for detecting *Plasmodium* sp.—including *Plasmodium falciparum* and/or *Plasmodium knowlesi* and/or *Plasmodium malariae* and/or *Plasmodium ovale* and/or *Plasmodium vivax*—in a sample. The oligomer combination generally includes at least two amplification oligomers for detecting *Plasmodium* sp.—including *Plasmodium falciparum* and/or *Plasmodium knowlesi* and/or *Plasmodium malariae* and/or *Plasmodium ovale* and/or *Plasmodium vivax*—in a sample, and may further include one or more additional oligomers as described herein for performing amplification-based detection of *Plasmodium* sp.—including *Plasmodium falciparum* and/or *Plasmodium knowlesi* and/or *Plasmodium malariae* and/or *Plasmodium ovale* and/or *Plasmodium vivax*—such as, for example, a capture probe and/or a detection probe.

Methods for detecting the presence or absence of *Plasmodium* sp. in a sample from a subject generally include performing a nucleic-acid-based detection assay for the specific detection in the sample of *Plasmodium* sp. nucleic acid. Nucleic-acid-based detection assays generally utilize oligonucleotides that specifically hybridize to a target nucleic acid of *Plasmodium* sp. with minimal cross-reactivity to other nucleic acids suspected of being in a sample. In some variations, an oligonucleotide or combination of oligonucleotides for nucleic-acid-based detection of *Plasmodium* sp. has minimal cross-reactivity to *Babesia* sp. (e.g., *B. microti*) nucleic acids.

In certain aspects of the invention, a combination of at least two oligomers is provided for determining the presence or absence of *Plasmodium* species in a sample. Typically, the oligomer combination includes at least first and second amplification oligomers for amplifying a *Plasmodium* sp. target region corresponding to a region of SEQ ID NO: 180. In such embodiments, at least one amplification oligomer comprises a target-hybridizing sequence in the sense orientation ("sense THS") and at least one amplification oligomer comprises a target-hybridizing sequence in the antisense orientation ("antisense THS"), where the sense THS and antisense THS of the amplification oligomers are each configured to specifically hybridize to a *Plasmodium* sp. target sequence corresponding to a sequence contained within SEQ ID NO: 180, and where the target-hybridizing sequences are selected such that the *Plasmodium* sequence targeted by the antisense THS is situated downstream of the *Plasmodium* sequence targeted by the sense THS (i.e., the at least two amplification oligomers are situated such that they flank the target region to be amplified).

In some embodiments, the *Plasmodium* sp. target region corresponds to a region of SEQ ID NO: 180 from about nucleotide position 844 or about nucleotide position 910 to about nucleotide position 1038, about nucleotide position 1051, about nucleotide position 1060, or about nucleotide position 1077. In other embodiments, the *Plasmodium* sp. target region corresponds to a region of SEQ ID NO: 180 from about nucleotide position 1153, about nucleotide position 1169, or about nucleotide position 1182 to about nucleotide position 1327, about nucleotide position 1354, or about nucleotide position 1382.

In some embodiments, a composition includes an amplification oligomer comprising a *Plasmodium*-specific target-hybridizing sequence substantially corresponding to, or identical to, the sequence shown in any one of SEQ ID NOs: 21-56, 80-102, and 182-184. In such variations, the oligomer combination includes at least one amplification oligomer comprising a *Plasmodium*-specific target-hybridizing sequence of the opposite polarity (sense vs. antisense or vice versa) as the target-hybridizing sequence of the oligomer as above, such that at least two amplification oligomers flank a target region to be amplified.

In some embodiments, a composition includes (1) at least one amplification oligomer comprising a *Plasmodium*-specific target-hybridizing region substantially corresponding to at least one sense oligomer sequence depicted in Table 1 below, and (2) at least one amplification oligomer comprising a *Plasmodium*-specific target hybridizing region substantially corresponding to at least one antisense oligomer sequence depicted in Table 1. In particular variations, the sense and/or antisense target-hybridizing sequence(s) of an amplification oligomer combination comprises or consists of the sense and/or antisense sequence(s) selected from Table 1.

TABLE 1

| Exemplary Sense and Antisense Amplification Oligomer Target-hybridizing Sequences for Amplification of *Plasmodium* species Target Regions | | |
| --- | --- | --- |
| SEQ ID NO | Sequence (5' → 3') | Sense/Antisense[1] |
| 21 | AATACTACAGCATGG | Sense |
| 22 | GGAAGGCAGCAGGCGCGTA | Sense |

TABLE 1-continued

| Exemplary Sense and Antisense Amplification Oligomer Target-hybridizing Sequences for Amplification of *Plasmodium* species Target Regions | | |
| --- | --- | --- |
| SEQ ID NO | Sequence (5' → 3') | Sense/Antisense[1] |
| 23 | AATACTACAGCATGGA | Sense |
| 24 | AATACTACAGCATGGAA | Sense |
| 25 | ATACTACAGCATGGAATA | Sense |
| 26 | ATTCAGATGTCAGAGGTGA | Sense |
| 27 | GTATTCAGATGTCAGAGGTGA | Sense |
| 28 | GTTACGATTAATAGGAGT | Sense |
| 29 | GTTACGATTAATAGGAGTA | Sense |
| 30 | GTTACGATTAATAGGAGTAG | Sense |
| 31 | GTTACGATTAATAGGAGTAGC | Sense |
| 32 | AATACTACAGCATGGAAT | Sense |
| 33 | AATACTACAGCATGGAATA | Sense |
| 34 | TACGATTAATAGGAGT | Sense |
| 35 | TACTACAGCATGGAATA | Sense |
| 36 | TATTCAGATGTCAGAGGTGA | Sense |
| 37 | TCAGTNCCTTATGAGAAATC | Sense |
| 38 | TGGCTTAGTTACGATT | Sense |
| 39 | TGGCTTAGTTACGATTAATAG | Sense |
| 40 | TTAATAGGAGTAGCTTGGGG | Sense |
| 41 | TTACGATTAATAGGAGT | Sense |
| 42 | TTCAGATGTCAGAGGTGA | Sense |
| 43 | TTGGCTTAGTTACGAT | Sense |
| 44 | TTGGCTTAGTTACGATTA | Sense |
| 45 | TTGGGGACATTCGTATTCAGA | Sense |
| 46 | TTTAGATTGCTTCCTTCAGT | Sense |
| 47 | TTTGAATACTANAGCA | Sense |
| 48 | ACATTCGTATTCAGATGTCAG | Sense |
| 49 | CTTAGTTACGATTAATAGGA | Sense |
| 50 | CGATTAATAGGAGTAGCTTGG | Sense |
| 51 | CTTAGTTACGATTAATAGGAGTAG | Sense |
| 52 | CTTGAATACTNCAGCA | Sense |
| 53 | GGCTTAGTTACGATTA | Sense |
| 54 | AATACTANAGCATGG | Sense |
| 55 | AATACTANAGCATGGAATA | Sense |
| 56 | AATTCTAAAGAAGAG | Sense |
| 80 | TTCACTCCCTTAACTTTCGTTCTTG | Antisense |
| 81 | CTTGATTAATGGAAGTATTTTAGA | Antisense |
| 82 | CTTAACTTTCGTTCTTGATTAATGGAAGT | Antisense |

TABLE 1-continued

Exemplary Sense and Antisense Amplification
Oligomer Target-hybridizing Sequences for
Amplification of *Plasmodium* species Target Regions

| SEQ ID NO | Sequence (5' → 3') | Sense/Antisense[1] |
|---|---|---|
| 83 | CCTACTCTTGTCTTAAACTA | Antisense |
| 84 | AAACGGCCATGCATCACCATCCAAGA | Antisense |
| 85 | CTCCCTTAACTTTCGTTCTTGATTAATGGAAGT | Antisense |
| 86 | CGACGGTATCTGATCGTCTTCACTCCC | Antisense |
| 87 | CTTAACTTTCGTTCTTGATTAATGGAAG | Antisense |
| 88 | CTTAACTTTCGTTCTTGATTAATGGAAGTA | Antisense |
| 89 | CACTCCCTTAACTTTCGTTCTTGATTAATG | Antisense |
| 90 | CACTCCCTTAACTTTCGTTCTTGATTAATGG | Antisense |
| 91 | CTTCACTCCCTTAACTTTCGTTCTTGATT | Antisense |
| 92 | CTTCACTCCCTTAACTTTCGTTCTTGAT | Antisense |
| 93 | ATCGTCTTCACTCCCTTAACTTTCGTTC | Antisense |
| 94 | CTCCCTTAACTTTCGTTCTTGATTAATG | Antisense |
| 95 | TCACTCCCTTAACTTTCGTTCTTGAT | Antisense |
| 96 | CCCTTAACTTTCGTTCTTGATTAATG | Antisense |
| 97 | CTTAACTTTCGTTCTTGATTAATG | Antisense |
| 98 | TAACTTTCGTTCTTGATTAATG | Antisense |
| 99 | ACTCCCTTAACTTTCGTTCTTGAT | Antisense |
| 100 | TCCCTTAACTTTCGTTCTTGAT | Antisense |
| 101 | AGGCAAATGCTTTCGCAGTTGTTNGTCT | Antisense |
| 102 | AGGCAAATGCTTTCGCAGTTGTTTGTCT | Antisense |
| 182 | TCAAGAAAGAGCTATNAATCTGTCAATCC | Antisense |
| 183 | GAAATCAAAGTCTTTGGGTTCTG | Sense |
| 184 | CAAAGTCTTTGGGTTCTGG | Sense |

[1]The Sense/Antisense designation of these sequences is for exemplary purposes only. Such designation does not necessarily limit a sequence to the accompanying designation.

In some embodiments, an oligomer combination comprises (a) an amplification oligomer comprising a target-hybridizing sequence (i) that is from about 14 to about 20 contiguous nucleotides in length, is contained in the sequence of SEQ ID NO: 162, and includes the sequence of SEQ ID NO: 163, or (ii) that is from about 14 to about 25 contiguous nucleotides in length, is contained in the sequence of SEQ ID NO: 166, and includes SEQ ID NO: 167 or SEQ ID NO: 168; and (b) an amplification oligomer comprising a target-hybridizing sequence that is from about 15 to about 33 contiguous nucleotides in length, is contained in SEQ ID NO: 169 and includes the sequence of SEQ ID NO: 171, SEQ ID NO: 172, or SEQ ID NO: 173. In some such embodiments, the oligomer combination comprises an amplification oligomer of (a)(i) where the target-hybridizing sequence of is selected from SEQ ID NOs: 21, 23-25, 32, 33, 35, 54, and 55, or where the target-hybridizing sequence is contained in the sequence of SEQ ID NO: 164 and includes the sequence of SEQ ID NO: 165 (e.g., a target-hybridizing sequence selected from SEQ ID NOs: 21, 23-25, 32, 33, and 35). In yet other embodiments, the oligomer combination comprises an amplification oligomer of (a)(ii) where the target-hybridizing sequence of includes the sequence of SEQ ID NO: 167 (e.g., a target-hybridizing sequence selected from the SEQ ID NOs: 28-31, 34, 40, 41, and 49-51), or where the target-hybridizing sequence includes the sequence of SEQ ID NO: 168 (e.g., a target-hybridizing sequence selected from SEQ ID NOs: 38, 39, 43, 44, and 53). In certain embodiments of an oligomer combination as above, the target-hybridizing sequence of (b) is selected from SEQ ID NOs: 80-82 and 85-100. In other embodiments, the target-hybridizing sequence of (b) is contained in the sequence of SEQ ID NO: 170 and includes the sequence of SEQ ID NO: 171 (e.g., a target-hybridizing sequence selected from SEQ ID NOs: 81, 82, 85, 87-90, 94, and 96-98), or is contained in the sequence of SEQ ID NO: 170 and includes the sequence of SEQ ID NO: 172 (e.g., a target-hybridizing sequence selected from SEQ ID NOs: 80, 82, 85, and 87-100).

In some embodiments, an oligomer combination comprises (a') an amplification oligomer comprising a target-hybridizing sequence that is contained in the sequence of SEQ ID NO: 185 and includes the sequence of SEQ ID NO: 37, SEQ ID NO: 46, or SEQ ID NO: 187; and (b') an amplification oligomer comprising a target-hybridizing sequence that is contained in the sequence of SEQ ID NO: 188 and includes the sequence of SEQ ID NO: 83, SEQ ID NO: 84, or SEQ ID NO: 182. In some embodiments, the amplification oligomer of (a') comprises a target-hybridizing sequence selected from SEQ ID NOs: 37, 46, 183, and 184, or a target-hybridizing sequence contained in the sequence of SEQ ID NO: 186 (e.g., a target-hybridizing sequence of SEQ ID NO: 183 or SEQ ID NO: 184). In certain embodiments, the amplification oligomers of (b') comprises a target-hybridizing sequence selected from SEQ ID NOs: 83, 84, and 182.

In certain embodiments, an amplification oligomer as described herein is a promoter primer or promoter provider further comprising a promoter sequence located 5' to the target-hybridizing sequence and which is non-complementary to the *Plasmodium* sp. target nucleic acid. For example, in some embodiments of an oligomer combination as described herein, an amplification oligomer of (b) or (b') as described above is a promoter primer further comprising a 5' promoter sequence. In particular embodiments, the promoter sequence is a T7 RNA polymerase promoter sequence such as, for example, a T7 promoter sequence having the sequence shown in SEQ ID NO: 179. In specific variations, an amplification oligomer is a promoter primer having the sequence shown selected from SEQ ID NOs: 57-77 and 181.

Table 2 shows particularly suitable combinations of amplification oligomer target-hybridizing sequences ("Amp 1" and "Amp 2") for detection of *Plasmodium* species target nucleic acid.

TABLE 2

Exemplary Combinations of Amplification
Oligomer Target-hybridizing Sequences.

| Amp 1 (SEQ ID NO) | Amp 2 (SEQ ID NO) |
|---|---|
| 30 | 5 |
| 33 | 8 |
| 49 | 11 |
| 21 | 14 |
| 30 | 17 |

31

TABLE 2-continued

Exemplary Combinations of Amplification
Oligomer Target-hybridizing Sequences.

| Amp 1 (SEQ ID NO) | Amp 2 (SEQ ID NO) |
|---|---|
| 33 | 20 |
| 49 | 23 |
| 21 | 26 |
| 30 | 29 |
| 21 | 32 |
| 34 | 35 |
| 53 | 38 |
| 21 | 41 |
| 34 | 44 |
| 53 | 46 |
| 183 | 182 |
| 184 | 182 |

In some embodiments, an oligomer combination as above includes at least two sense amplification oligomers and/or at least two antisense amplification oligomers flanking a *Plasmodium* sp. target region. For example, an oligomer combination may include (a) at least two amplification oligomer (e.g., two or three amplification oligomers) each comprising a target-hybridizing sequence that is from about 14 to about 25 contiguous nucleotides in length, is contained in the sequence of SEQ ID NO: 166, and includes SEQ ID NO: 167 or SEQ ID NO 16 and/or (b) at least two amplification oligomers (e.g., two or three amplification oligomers) each comprising a target-hybridizing sequence that is from about 15 to about 33 contiguous nucleotides in length, is contained in SEQ ID NO: 169 and includes the sequence of SEQ ID NO: 171, SEQ ID NO: 172, or SEQ ID NO: 173; in some such variations, the oligomer combination includes (a) a first amplification oligomer comprising a target-hybridizing sequence that includes the sequence of SEQ ID NO: 167 (e.g., the target-hybridizing sequence of SEQ ID NO: 34) and a second amplification oligomer comprising a target-hybridizing sequence that includes the sequence of SEQ ID NO: 168 (e.g., the target-hybridizing sequence of SEQ ID NO: 53). In other embodiments comprising at least two sense amplification oligomers and/or at least two antisense amplification oligomers, an oligomer combination comprises (a)(i) an amplification oligomer comprising a target-hybridizing sequence that is from about 14 to about 20 contiguous nucleotides in length, is contained in the sequence of SEQ ID NO: 162, and includes the sequence of SEQ ID NO: 163, and (ii) an amplification oligomer comprising a target-hybridizing sequence that is from about 14 to about 25 contiguous nucleotides in length, is contained in the sequence of SEQ ID NO: 166, and includes SEQ ID NO: 167 or SEQ ID NO: 168; and/or (b) at least two amplification oligomers (e.g., two or three amplification oligomers) each comprising a target-hybridizing sequence that is from about 15 to about 33 contiguous nucleotides in length, is contained in SEQ ID NO: 169 and includes the sequence of SEQ ID NO: 171, SEQ ID NO: 172, or SEQ ID NO: 173; in some such variations, the oligomer combination includes (a)(i) an amplification oligomer comprising a target-hybridizing sequence that is contained in the sequence of SEQ ID NO: 164 and includes the sequence of SEQ ID NO: 165 (e.g., the target-hybridizing sequence of SEQ ID NO: 21), and (a)(ii) an amplification comprising a target-hybridizing sequence that includes the sequence of SEQ ID NO: 167 (e.g., the target-hybridizing sequence of SEQ ID NO: 34). In some embodiments of an oligomer combination as above comprising at least two amplification oligomers of (b), oligomer combination comprise first and second amplification oligomers of (b), each comprising a target-hybridizing sequence that is contained in SEQ ID NO: 170 and includes the sequence of SEQ ID NO: 171 or SEQ ID NO: 172 (e.g., a first amplification oligomer comprising the target-hybridizing sequence of SEQ ID NO: 94 and a second amplification oligomer comprising the target-hybridizing sequence of SEQ ID NO: 95).

In some embodiments, an oligomer combination as described herein further comprises at least one capture probe oligomer comprising a target-hybridizing sequence configured to specifically hybridize to *Plasmodium* species target nucleic acid. In some such embodiments, the capture probe oligomer comprises a target-hybridizing sequence a sequence substantially corresponding to to a sequence contained in the complement of SEQ ID NO: 180. In some embodiments, a capture probe oligomer target-hybridizing sequence is covalently attached to a sequence or moiety that binds to an immobilized probe. Suitable capture probe oligomer target-hybridizing sequences include sequences that are up to about 30 contiguous nucleotides in length and include a sequence substantially corresponding to a sequence selected from SEQ ID NOs: 11-15, 17, 19, and 20 (e.g., a target-hybridizing sequence comprising or consisting of a sequence selected from SEQ ID NOs: 11-15, 17, 19, and 20, including DNA equivalents and DNA/RNA chimerics thereof). In some embodiments, a capture probe oligomer comprises or consists of a sequence selected from SEQ ID NOs: 1-5, 7, 9, and 10. In some embodiments, the oligomer combination includes at least two capture probe oligomers (e.g., at least two capture probe oligomers as above). A first capture probe oligomer comprising the target-hybridizing sequence of SEQ ID NO: 19 (e.g., a capture probe oligomer comprising the sequence of SEQ ID NO: 9) and a second capture probe oligomer comprising the target-hybridizing sequence of SEQ ID NO: 20 (e.g., a capture probe oligomer comprising the sequence of SEQ ID NO: 10) are particularly suitable for use together in oligomer combinations as described herein.

In certain variations, an oligomer combination as described herein further comprises at least one detection probe oligomer configured to specifically hybridize to a *Plasmodium* sp. target sequence that is amplifiable using the at least two amplification oligomers targeting a *Plasmodium* sp. target region. In some embodiments where a *Plasmodium* sp. target region corresponds to a region of SEQ ID NO: 180 from about nucleotide position 844 or about nucleotide position 910 to about nucleotide position 1038, about nucleotide position 1051, about nucleotide position 1060, or about nucleotide position 1077, the oligomer combination includes a detection probe oligomer that specifically hybridizes to a target region corresponding to a region of SEQ ID NO: 180 from about nucleotide position 951 to about nucleotide position 998 or the full complement thereof. For example, a detection probe oligomer may include a target-hybridizing sequence that is from about 13 to about 40 nucleotides in length and is (i) contained in the sequence of SEQ ID NO: 196 or its complement and (ii) includes a sequence selected from SEQ ID NO: 175, SEQ ID NO: 176, SEQ ID NO: 177, and SEQ ID NO: 178, including complements thereof. In more specific variations, a detection probe oligomer target-hybridizing sequence is (i) contained in the sequence of SEQ ID NO: 197 or its complement and (ii) includes the sequence of SEQ ID NO: 174 or SEQ ID NO: 175, including complements thereof. In other variations, a detection probe oligomer target-hybridizing sequence is (i) contained in the sequence of SEQ ID NO: 196 or its complement and (ii) includes a sequence selected from SEQ ID NO: 177 and SEQ ID NO: 178, including complements thereof. Particularly suitable detection probe oligomer target-hybridizing sequences include SEQ ID NOs: 131, 132, 135, 140, 145, 147-157, and 159-161, including complements thereof. Suitable detection probes further include DNA equivalents and DNA/RNA chimerics of any of the above.

In some embodiments where a *Plasmodium* sp. target region corresponds to a region of SEQ ID NO: 180 from about nucleotide position 1153, about nucleotide position 1169, or about nucleotide position 1182 to about nucleotide position 1327, about nucleotide position 1354, or about nucleotide position 1382, the oligomer combination includes a detection probe oligomer that specifically hybridizes to a target region corresponding to a region of SEQ ID NO: 180 from about nucleotide position 1210 to about nucleotide position 1233 or the full complement thereof. For example, a detection probe oligomer may include a target-hybridizing sequence that is at least about 13 nucleotides in length and is (i) contained in the sequence of SEQ ID NO: 189 or its complement and (ii) includes a sequence selected from SEQ ID NO: 190 and SEQ ID NO: 191, including complements thereof. Particularly suitable detection probe oligomer target-hybridizing sequences include SEQ ID NOs: 125-130 and 143, including complements thereof. Suitable detection probes further include DNA equivalents and DNA/RNA chimerics of any of the above.

Table 3 shows exemplary combinations of detection probe target hybridizing sequences together with first and second amplification oligomer target-hybridizing sequences ("Amp 1" and "Amp 2") for detection of *Plasmodium* species target nucleic acid.

TABLE 3

Exemplary Combinations of Amplification Oligomer
and Detection Probe Target-hybridizing Sequences.

| Amplification Oligomer THSs | | Detection Probe |
|---|---|---|
| Amp 1 (SEQ ID NO) | Amp 2 (SEQ ID NO) | THS (SEQ ID NO) |
| 30 | 82 | 151 |
| 30 | 82 | 157 |
| 33 | 82 | 155 |
| 49 | 82 | 150 |
| 49 | 82 | 155 |
| 21 | 89 | 148 |
| 21 | 89 | 152 |
| 30 | 89 | 148 |
| 30 | 89 | 152 |
| 33 | 89 | 158 |
| 49 | 89 | 150 |
| 21 | 92 | 148 |
| 21 | 92 | 152 |
| 30 | 92 | 148 |
| 30 | 92 | 152 |
| 21 | 94 | 148 |
| 21 | 94 | 152 |
| 34 | 94 | 148 |
| 34 | 94 | 152 |
| 34 | 94 | 157 |
| 53 | 94 | 148 |
| 53 | 94 | 152 |
| 53 | 94 | 157 |
| 21 | 95 | 148 |
| 21 | 95 | 152 |
| 34 | 95 | 148 |
| 34 | 95 | 152 |
| 34 | 95 | 157 |
| 53 | 95 | 148 |
| 53 | 95 | 152 |
| 53 | 95 | 157 |

TABLE 3-continued

Exemplary Combinations of Amplification Oligomer
and Detection Probe Target-hybridizing Sequences.

| Amplification Oligomer THSs | | Detection Probe |
|---|---|---|
| Amp 1 (SEQ ID NO) | Amp 2 (SEQ ID NO) | THS (SEQ ID NO) |
| 183 | 182 | 126 |
| 183 | 182 | 127 |
| 183 | 182 | 128 |
| 183 | 182 | 143 |
| 183 | 182 | 129 |
| 184 | 182 | 126 |

In some variations, an oligomer combination includes at least two detection probe oligomers (e.g., at least two specific detection probes as described herein). For example, where a *Plasmodium* sp. target region corresponds to a region of SEQ ID NO: 180 from about nucleotide position 844 or about nucleotide position 910 to about nucleotide position 1038, about nucleotide position 1051, about nucleotide position 1060, or about nucleotide position 1077, an oligomer combination may include (A) a first detection probe oligomer comprising a target-hybridizing sequence that is (i) contained in the sequence of SEQ ID NO: 197 or its complement and (ii) includes the sequence of SEQ ID NO: 175 or its complement, and (B) a second detection probe oligomer comprising a target-hybridizing sequence that is (i) contained in the sequence of SEQ ID NO: 197 or its complement and (ii) includes the sequence of SEQ ID NO: 176 or its complement (including DNA equivalents or DNA/RNA chimerics of the foregoing). Particularly suitable combinations of first and second detection probe oligomers include a first detection probe oligomer comprising the target-hybridizing sequence of SEQ ID NO: 157 or its complement, or a DNA equivalent or DNA/RNA chimeric thereof, and a second detection probe oligomer comprising a target-hybridizing sequence selected from SEQ ID NO: 148 and SEQ ID NO: 152, including complements, DNA equivalents, and DNA/RNA chimerics thereof.

A detection probe oligomer may contain a 2'-methoxy backbone at one or more linkages in the nucleic acid backbone. In some embodiments, the at least one detection probe oligomer is provided in an amplicon detection reaction mixture.

Typically, a detection probe oligomer in accordance with the present invention further includes a label. Particularly suitable labels include compounds that emit a detectable light signal, e.g., fluorophores or luminescent (e.g., chemiluminescent) compounds that can be detected in a homogeneous mixture. More than one label, and more than one type of label, may be present on a particular probe, or detection may rely on using a mixture of probes in which each probe is labeled with a compound that produces a detectable signal (see, e.g., U.S. Pat. Nos. 6,180,340 and 6,350,579, each incorporated by reference herein). Labels may be attached to a probe by various means including covalent linkages, chelation, and ionic interactions, but preferably the label is covalently attached. For example, in some embodiments, a detection probe has an attached chemiluminescent label such as, e.g., an acridinium ester (AE) compound (see, e.g., U.S. Pat. Nos. 5,185,439; 5,639,604; 5,585,481; and 5,656,744; each incorporated by reference herein), which in typical variations is attached to the probe by a non-nucleotide linker (see, e.g., U.S. Pat. Nos. 5,585,481; 5,656,744; and 5,639,604, particularly at column 10, line 6 to column 11, line 3, and Example 8; each incorporated by reference herein). In other embodiments, a detection probe comprises both a fluorescent label and a quencher, a combination that is particularly useful in fluorescence resonance energy transfer (FRET) assays. Specific variations of such detection probes include, e.g., a TaqMan detection probe (Roche Molecular Diagnostics) and a "molecular beacon" (see, e.g., Tyagi et al., Nature Biotechnol. 16:49-53, 1998; U.S. Pat. Nos. 5,118,801 and 5,312,728; each incorporated by reference herein).

A detection probe oligomer in accordance with the present invention may further include a non-target-hybridizing sequence. Specific embodiments of such detection probes include, for example, probes that form conformations held by intramolecular hybridization, such as conformations generally referred to as hairpins. Particularly suitable hairpin probes include a "molecular torch" (see, e.g., U.S. Pat. Nos. 6,849,412; 6,835,542; 6,534,274; and 6,361,945, each incorporated by reference herein) and a "molecular beacon" (see, e.g., Tyagi et al., supra; U.S. Pat. Nos. 5,118,801 and 5,312,728, supra). Methods for using such hairpin probes are well-known in the art.

In yet other embodiments, a detection probe is a linear oligomer that does not substantially form conformations held by intramolecular bonds. In specific variations, a linear detection probe oligomer includes a chemiluminescent compound as the label, preferably an acridinium ester (AE) compound.

Also provided by the present invention are detection probe oligomers, capture probe oligomers, and combinations thereof as described herein.

In other aspects, the present invention provides methods for detecting the presence or absence of *Plasmodium* sp. in a sample from a subject. Such methods generally include performing a nucleic-acid-based detection assay for the specific detection in the sample of *Plasmodium* sp. nucleic acid. A nucleic-acid-based detection assay for specific detection of *Plasmodium* sp. may use any one or more *Plasmodium* sp.-specific oligomers as described herein (e.g., an oligomer combination as described herein comprising at least two amplification oligomers; or a detection probe or combination of detection probes as described herein). A positive signal from a nucleic-acid-based detection assay in accordance with the present invention is indicative of the presence of one or more of *Plasmodium falciparum, Plasmodium knowlesi, Plasmodium malariae, Plasmodium ovale* and/or *Plasmodium vivax* in a sample.

In some embodiments of a method comprising the use of a nucleic-acid-based detection assay, an amplification-based assay is used to detect *Plasmodium* sp. Such amplification-based assay methods generally include performing a nucleic acid amplification of an *Plasmodium* sp. target region and detecting the amplified product (e.g., by specifically hybridizing the amplified product with a nucleic acid detection probe that provides a signal to indicate the presence of *Plasmodium* sp. in the sample). The amplification step includes contacting the sample with one or more amplification oligomers specific for a target sequence in a *Plasmodium* sp. target nucleic acid to produce an amplified product if *Plasmodium* sp. nucleic acid is present in the sample. In particular embodiments, a combination of at least two amplification oligomers as described herein are used at the amplification step. Amplification synthesizes additional copies of the target sequence or its complement by using at least one nucleic acid polymerase and an amplification oligomer to produce the copies from a template strand (e.g., by extending the sequence from a primer using the template strand). Suitable amplification methods include, for example, replicase-mediated amplification, polymerase chain reaction (PCR), ligase chain reaction (LCR), strand-displacement amplification (SDA), and transcription-mediated or transcription-associated amplification (TMA). Such amplification methods are well-known in the art (see, e.g., discussion of amplification methods in Definitions section, supra) and are readily used in accordance with the methods of the present disclosure.

Detection of the amplified products may be accomplished by a variety of methods to detect a signal specifically associated with the amplified target sequence. The nucleic acids may be associated with a surface that results in a physical change, such as a detectable electrical change. Amplified nucleic acids may be detected by concentrating them in or on a matrix and detecting the nucleic acids or dyes associated with them (e.g., an intercalating agent such as ethidium bromide or cyber green), or detecting an increase in dye associated with nucleic acid in solution phase. Other methods of detection may use uses a hybridizing step that includes contacting the amplified product with at least one detection probe configured to specifically hybridize to a sequence in the amplified product and detecting the presence of the probe:product complex, or by using a complex of probes that may amplify the detectable signal associated with the amplified products (e.g., U.S. Pat. Nos. 5,424,413; 5,451,503; and 5,849,481). Directly or indirectly labeled probes that specifically associate with the amplified product provide a detectable signal that indicates the presence of the target nucleic acid in the sample. In some embodiments, a method utilizing an amplification-based assay for detection of *Plasmodium* species utilizes one or more detection probe oligomers as described herein for detection of an amplified product.

Detection probes that hybridize to the complementary amplified sequences may be DNA or RNA oligomers, or oligomers that contain a combination of DNA and RNA nucleotides, or oligomers synthesized with a modified backbone, e.g., an oligomer that includes one or more 2'-methoxy substituted ribonucleotides. Probes used for detection of the amplified sequences may be unlabeled and detected indirectly (e.g., by binding of another binding partner to a moiety on the probe) or may be labeled with a variety of detectable labels. In some embodiments of a method for detecting *Plasmodium* species, such as in certain embodiments using transcription-mediated amplification (TMA), the detection probe is a linear chemiluminescently labeled probe such as, e.g., a linear acridinium ester (AE) labeled probe. The detection step may also provide additional information on the amplified sequence, such as, e.g., all or a portion of its nucleic acid base sequence. Detection may be performed after the amplification reaction is completed, or may be performed simultaneously with amplifying the target region, e.g., in real time. In one embodiment, the detection step allows homogeneous detection, e.g., detection of the hybridized probe without removal of unhybridized probe from the mixture (see, e.g., U.S. Pat. Nos. 5,639,604 and 5,283,174).

In embodiments that detect the amplified product near or at the end of the amplification step, a linear detection probe may be used to provide a signal to indicate hybridization of the probe to the amplified product. One example of such detection uses a luminescently labeled probe that hybridizes to target nucleic acid. Luminescent label is then hydrolyzed from non-hybridized probe. Detection is performed by chemiluminescence using a luminometer (see, e.g., International Patent Application Pub. No. WO 89/002476). In other embodiments that use real-time detection, the detection probe may be a hairpin probe such as, for example, a molecular beacon, molecular torch, or hybridization switch probe that is labeled with a reporter moiety that is detected when the probe binds to amplified product. Such probes may comprise target-hybridizing sequences and non-target-hybridizing sequences. Various forms of such probes have been described previously (see, e.g., U.S. Pat. Nos. 5,118,801; 5,312,728; 5,925,517; 6,150,097; 6,849,412; 6,835,542; 6,534,274; and 6,361,945; and US Patent Application Pub. Nos. 20060068417A1 and 20060194240A1).

Some amplification methods that use TMA amplification include the following steps. Briefly, the target nucleic acid that contains the sequence to be amplified is provided as single stranded nucleic acid (e.g., ssRNA or ssDNA). Those skilled in the art will appreciate that conventional melting of double stranded nucleic acid (e.g., dsDNA) may be used to provide single-stranded target nucleic acids. A promoter primer binds specifically to the target nucleic acid at its target sequence and a reverse transcriptase (RT) extends the 3' end of the promoter primer using the target strand as a template to create a cDNA copy of the target sequence strand, resulting in an RNA:DNA duplex. An RNase digests the RNA strand of the RNA:DNA duplex and a second primer binds specifically to its target sequence, which is located on the cDNA strand downstream from the promoter primer end. RT synthesizes a new DNA strand by extending the 3' end of the second primer using the first cDNA template to create a dsDNA that contains a functional promoter sequence. An RNA polymerase specific for the promoter sequence then initiates transcription to produce RNA transcripts that are about 100 to 1000 amplified copies ("amplicons") of the initial target strand in the reaction. Amplification continues when the second primer binds specifically to its target sequence in each of the amplicons and RT creates a DNA copy from the amplicon RNA template to produce an RNA:DNA duplex. RNase in the reaction mixture digests the amplicon RNA from the RNA:DNA duplex and the promoter primer binds specifically to its complementary sequence in the newly synthesized DNA. RT extends the 3' end of the promoter primer to create a dsDNA that contains a functional promoter to which the RNA polymerase binds to transcribe additional amplicons that are complementary to the target strand. The autocatalytic cycles of making more amplicon copies repeat during the course of the reaction resulting in about a billion-fold amplification of the target nucleic acid present in the sample. The amplified products may be detected in real-time during amplification, or at the end of the amplification reaction by using a probe that binds specifically to a target sequence contained in the amplified products. Detection of a signal resulting from the bound probes indicates the presence of the target nucleic acid in the sample.

In some embodiments, the method utilizes a "reverse" TMA reaction. In such variations, the initial or "forward" amplification oligomer is a priming oligonucleotide that hybridizes to the target nucleic acid in the vicinity of the 3'-end of the target region. A reverse transcriptase (RT) synthesizes a cDNA strand by extending the 3'-end of the primer using the target nucleic acid as a template. The second or "reverse" amplification oligomer is a promoter primer or promoter provider having a target-hybridizing sequence configured to hybridize to a target-sequence contained within the synthesized cDNA strand. Where the second amplification oligomer is a promoter primer, RT extends the 3' end of the promoter primer using the cDNA strand as a template to create a second, cDNA copy of the target sequence strand, thereby creating a dsDNA that contains a functional promoter sequence. Amplification then continues essentially as described above for initiation of transcription from the promoter sequence utilizing an RNA polymerase. Alternatively, where the second amplification oligomer is a promoter provider, a terminating oligonucleotide, which hybridizes to a target sequence that is in the vicinity to the 5'-end of the target region, is typically utilized to terminate extension of the priming oligomer at the 3'-end of the terminating oligonucleotide, thereby providing a defined 3'-end for the initial cDNA strand synthesized by extension from the priming oligomer. The target-hybridizing sequence of the promoter provider then hybridizes to the defined 3'-end of the initial cDNA strand, and the 3'-end of the cDNA strand is extended to add sequence complementary to the promoter sequence of the promoter provider, resulting in the formation of a double-stranded promoter sequence. The initial cDNA strand is then used a template to transcribe multiple RNA transcripts complementary to the initial cDNA strand, not including the promoter portion, using an RNA polymerase that recognizes the double-stranded promoter and initiates transcription therefrom. Each of these RNA transcripts is then available to serve as a template for further amplification from the first priming amplification oligomer.

In some embodiments of a method comprising the use of a nucleic-acid-based detection assay, a non-amplification-based assay is used to detect *Plasmodium* sp. In some such embodiments, the non-amplification-based assay is a hybridization assay comprising the hybridization of a specific detection probe to a target nucleic acid. Methods for conducting polynucleotide hybridization assays have been well developed in the art. Hybridization assay procedures and conditions will vary depending on the application and are selected in accordance with the general binding methods known, including those referred to in, e.g., Maniatis et al, Molecular Cloning: A Laboratory Manual (3rd ed. Cold Spring Harbor, N.Y., 2002), and Berger and Kimmel, Methods in Enzymology, Vol. 152, Guide to Molecular Cloning Techniques (Academic Press, Inc., San Diego, Calif., 1987). Generally, the probe and sample are mixed under conditions that will permit specific nucleic acid hybridization, and specific hybridization of the probe to its respective target is then detected. Nucleic acid hybridization is adaptable to a variety of assay formats. One suitable format is the sandwich assay format, which is particularly adaptable to hybridization under non-denaturing conditions. A primary component of a sandwich-type assay is a solid support, which has adsorbed to it or covalently coupled to it immobilized nucleic acid probe that is unlabeled and complementary to one portion of the DNA sequence. Target nucleic acid is hybridized to the immobilized probe, and a second, labeled detection probe—which is complementary to a second and different region of the same DNA strand to which the immobilized, unlabeled nucleic acid probe is hybridized—is hybridized to the [target nucleic acid]:[immobilized probe] duplex to detect the target nucleic acid. Another exemplary format utilizes electrochemical detection of target nucleic acids hybridized to unlabeled detection probes immobilized on a suitable electrode surface as a signal transducer. See, e.g., Drummond et al., *Nat. Biotechnol.* 21: 1192, 2003; Gooding, *Electroanalysis* 14: 1149, 2002; Wang, *Anal. Chim. Acta* 469:63, 2002; Cagnin et al., *Sensors* 9:3122, 2009; Katz and Willner, *Electroanalysis* 15:913, 2003; Daniels and Pourmand, *Electroanalysis* 19: 1239, 2007.

In certain embodiments of a method for detecting *Plasmodium* species comprising a hybridization assay, the hybridization assay utilizes one or more detection probe oligomers as described herein.

In some embodiments, a non-amplification-based assay for detection of *Plasmodium* sp. is a cleavage-based assay, in which a probe oligonucleotide containing a non-target-hybridizing flap region is cleaved in an overlap-dependent manner by a flap endonuclease to release a cleavage product that is then detected. Exemplary cleavage-based assay reagents are described in, e.g., Lyamichev et al. (*Nat. Biotechnol.* 17:292-296, 1999), Ryan et al. (*Mol. Diagn.* 4: 135-144, 1999), and Allawi et al. (*J. Clin. Microbiol.* 44:3443-3447, 2006).

Appropriate conditions for flap endonuclease reactions are either known or can be readily determined using methods known in the art (see, e.g., Kaiser et al., *J. Biol. Chem.* 274:2138-721394, 1999). Exemplary flap endonucleases that may be used in the method include *Thermus aquaticus* DNA polymerase I, *Thermus thermophilus* DNA polymerase I, mammalian FEN-1, *Archaeoglobus fulgidus* FEN-1, *Methanococcus jannaschii* FEN-1, *Pyrococcus fiiriosus* FEN-1, *Methanobacterium thermoautotrophicum* FEN-1, *Thermus thermophilus* FEN-1, CLEAVASE® (Hologic, Inc., Madison, WI), *S. cerevisiae* RTH1, *S. cerevisiae* RAD27, *Schizosaccharomyces pombe* rad2, bacteriophage T5 5'-3' exonuclease, *Pyrococcus horikoshii* FEN-1, human endonuclease 1, calf thymus 5'-3' exonuclease, including homologs thereof in eubacteria, eukaryotes, and archaea, such as members of the class II family of structure-specific enzymes, as well as enzymatically active mutants or variants thereof. Descriptions of flap endonucleases can be found in, for example, Lyamichev et al., *Science* 260:778-783, 1993; Eis et al., *Nat. Biotechnol.* 19:673-676, 2001; Shen et al., *Trends in Bio. Sci.* 23: 171-173, 1998; Kaiser et al., *J. Biol. Chem.* 274:21387-21394, 1999; Ma et al., *J. Biol. Chem.* 275:24693-24700, 2000; Allawi et al., *J. Mol. Biol.* 328: 537-554, 2003; Sharma et al., *J. Biol. Chem.* 278:23487-23496, 2003; and Feng et al., *Nat. Struct. Mol. Biol.* 11: 450-456, 2004.

In certain variations, a cleavage-based assay detects an RNA target nucleic acid of *Plasmodium* sp., and the cleavage-based assay utilizes a flap endonuclease that is capable of cleaving and RNA:DNA linear duplex structure. In some alternative embodiments, a cleavage-based assay detects a DNA target nucleic acid of *Plasmodium* sp., and the cleavage-based assay utilizes a flap endonuclease that is capable of cleaving and DNA:DNA linear duplex structure. Exemplary flap endonucleases capable of cleaving RNA:DNA duplexes include polymerase-deficient 5' nucleases of the genus *Thermus* as well as certain CLEAVASE® enzymes (Hologic, Inc., Madison, WI) such as, for example, CLEAVASE® BN (BstX-Notl deletion of Taq polymerase, see U.S. Pat. No. 5,614,402), CLEAVASE® II ("AG" mutant of full length Taq polymerase, see U.S. Pat. No. 5,614,402), CLEAVASE® VII (synthesis-deficient mutation of full length *Thermus thermophilus* polymerase), CLEAVASE® IX (polymerase deficient mutant of the Tth DNA polymerase), and CLEAVASE® XII (polymerase deficient chimeric polymerase constructed from fragments of taq DNA polymerase and Tth DNA polymerase). Exemplary flap endonucleases capable of cleaving DNA:DNA duplexes include the flap endonucleases indicated above, as well as CLEAVASE® 2.0 (*Archaeoglobus fulgidus* FEN-1), CLEAVASE® 2.1 (*Archaeoglobus fulgidus* FEN-1 with 6 histidines on the C-terminus), CLEAVASE® 3.0 (*Archaeoglobus veneficus* FEN-1), and CLEAVASE® 3.1 (*Archaeoglobus veneficus* FEN-1 with 6 histidines on the C-terminus).

In some embodiments, a cleavage-based assay detects an RNA target nucleic acid of *Plasmodium* sp., and the assay includes a step for synthesizing a DNA complement of an RNA target region, which cDNA strand is then hybridized to overlapping first and second probe oligonucleotides to form a linear duplex cleavage structure for cleavage by the flap endonuclease. Reaction conditions for synthesizing cDNA from an RNA template, using an RNA-dependent DNA polymerase (reverse transcriptase), are well-known in the art.

In certain embodiments utilizing a nucleic-acid-based detection assay, the method further includes purifying the *Plasmodium* sp. target nucleic acid from other components in the sample. Such purification may include methods of separating and/or concentrating organisms contained in a sample from other sample components. In particular embodiments, purifying the target nucleic acid includes capturing the target nucleic acid to specifically or non-specifically separate the target nucleic acid from other sample components. Non-specific target capture methods may involve selective precipitation of nucleic acids from a substantially aqueous mixture, adherence of nucleic acids to a support that is washed to remove other sample components, or other means of physically separating nucleic acids from a mixture that contains *Plasmodium* sp. nucleic acid and other sample components. In some embodiments, purification includes lysing a sample of cells such as, for example, blood cells (e.g., red blood cells) and purifying any *Plasmodium* sp. target nucleic acid from the lysed cell sample. Exemplary lysis reagents and methods for used in accordance with the present invention are described in U.S. Pat. No. 10,093,989 and PCT Pub. No. WO 2017/189746, each incorporated by reference herein.

In some embodiments, a target nucleic acid of *Plasmodium* sp. is separated from other sample components by hybridizing the target nucleic acid to a capture probe oligomer. The capture probe oligomer comprises a target-hybridizing sequence configured to specifically or non-specifically hybridize to a target nucleic acid so as to form a [target nucleic acid]: [capture probe] complex that is separated from other sample components. Capture probes comprising target-hybridizing sequences suitable for non-specific capture of target nucleic acids are described in, e.g., PCT Pub. No. WO 2008/016988. In some specific variations comprising target-hybridizing sequence(s) configured to specifically hybridize to a *Plasmodium* sp. target nucleic acid, a *Plasmodium* sp.-specific capture probe comprises a target-hybridizing sequence that is up to about 30 contiguous nucleotides in length and includes a sequence substantially corresponding to a sequence selected from SEQ ID NOs: 11-15, 17, 19, and 20 (e.g., a target-hybridizing sequence comprising or consisting of a sequence selected from SEQ ID NOs: 11-15, 17, 19, and 20, including DNA equivalents and DNA/RNA chimerics thereof). In a preferred variation, the capture probe binds the [target nucleic acid]:[capture probe] complex to an immobilized probe to form a [target nucleic acid]:[capture probe]: [immobilized probe] complex that is separated from the sample and, optionally, washed to remove non-target sample components (see, e.g., U.S. Pat. Nos. 6,110,678, 6,280,952 and 6,534, 273). In such variations, the capture probe oligomer further comprises a sequence or moiety that binds the capture probe, with its bound target sequence, to an immobilized probe attached to a solid support, thereby permitting the hybridized target nucleic acid to be separated from other sample components.

In more specific embodiments, the capture probe oligomer includes a tail portion (e.g., a 3' tail) that is not complementary to target nucleic acid but that specifically hybridizes to a sequence on the immobilized probe, thereby serving as the moiety allowing the target nucleic acid to be separated from other sample components, such as previously described in, e.g., U.S. Pat. No. 6,110,678. Any sequence may be used in a tail region, which is generally about 5 to 50 nt long, and preferred embodiments include a substantially homopolymeric tail of about 10 to 40 nt (e.g., A10 to A40), more preferably about 14 to 33 nt (e.g., A14 to A30 or T3A14 to T3A30), that bind to a complementary immobilized sequence (e.g., poly-T) attached to a solid support, e.g., a matrix or particle. In some such embodiments comprising target-hybridizing sequence(s) configured to specifically hybridize to *Plasmodium* sp. target nucleic acid, a *Plasmodium* sp.-specific capture probe comprises or consists of a nucleotide sequence selected from SEQ ID NOs: 1-5, 7, 9, and 10.

Target capture typically occurs in a solution phase mixture that contains one or more capture probe oligomers that hybridize to the target nucleic acid under hybridizing conditions, usually at a temperature higher than the Tm of the [tail sequence]:[immobilized probe sequence] duplex. For embodiments comprising a capture probe tail, the [target nucleic acid]:[capture probe] complex is captured by adjusting the hybridization conditions so that the capture probe tail hybridizes to the immobilized probe, and the entire complex on the solid support is then separated from other sample components. The support with the attached [immobilized probe]:[capture probe]:[target nucleic acid] may be washed one or more times to further remove other sample components. Preferred embodiments use a particulate solid support, such as paramagnetic beads, so that particles with the attached [target nucleic acid]:[capture probe]:[immobilized probe] complex may be suspended in a washing solution and retrieved from the washing solution, preferably by using magnetic attraction. In embodiments of the method comprising the use of an amplification-based detection assay, to limit the number of handling steps, a target nucleic acid may be amplified by simply mixing the target nucleic acid in the complex on the support with amplification oligomers and proceeding with amplification steps.

In accordance with the present disclosure, detecting the presence or absence of *Plasmodium* sp. may be performed separately (e.g., in a separate reaction vessel), or performed together with another assay as a multiplex reaction system. Accordingly, in some embodiments, a method as described herein utilizes a multiplex reaction, where the reaction mix contains reagents for assaying multiple (e.g., at least two, three, four, or more) different target sequences in parallel. In these cases, a reaction mix may contain multiple different target-specific oligonucleotides for performing the detection assay. For example, in a method utilizing an amplification-based detection assay, a multiplex reaction may contain multiple sets (e.g., multiple pairs) of amplification oligomers (for example, multiple pairs of PCR primers or multiple pairs of TMA amplification oligomers (e.g., for TMA, multiple pairs of promoter primer and non-promoter primer, or multiple pairs of promoter provider and non-promoter primer)). In other embodiments utilizing a cleavage-based detection assay, a multiplex reaction may contain multiple probe oligonucleotides having different flaps, multiple different overlapping probe oligonucleotides, and multiple different FRET cassettes for detecting the different flaps, once they are cleaved.

The oligomer combination described herein may be in the form of a reaction mixture or a kit comprising the oligomers. The reaction mixture or kit may further include a number of optional components such as, for example, capture probe nucleic acids or arrays of capture probe nucleic acids. For an amplification reaction mixture, the reaction mixture will typically include other reagents suitable for performing in vitro amplification such as, e.g., buffers, salt solutions, appropriate nucleotide triphosphates (e.g., dATP, dCTP, dGTP, dTTP, ATP, CTP, GTP and UTP), and/or enzymes (e.g., reverse transcriptase, and/or RNA polymerase), and will typically include test sample components, in which a *Plasmodium* sp. target nucleic acid may or may not be present. A kit comprising an oligomer combination for amplification of *Plasmodium* sp. may also include other reagents suitable for performing in vitro amplification such as, e.g., buffers, salt solutions, appropriate nucleotide triphosphates (e.g., dATP, dCTP, dGTP, dTTP, ATP, CTP, GTP and UTP), and/or enzymes (e.g., reverse transcriptase, and/or RNA polymerase). For an oligomer combination (e.g., reaction mixture or kit) that includes a detection probe together with an amplification oligomer combination targeting a common target nucleic acid, selection of amplification oligomers and detection probe oligomers are linked by a common target region (i.e., the combination will include a probe that binds to a sequence amplifiable by the amplification oligomer combination).

The compositions, methods, reaction mixtures, systems, kits and the like for detection of *Plasmodium* nucleic acids are further illustrated by the following non-limiting examples.

EXAMPLES

"Parasite Transport Solution" generally refers to a solution formulated to preserve a sample, and in some instances formulated to at least partially lyse one or more cell types in a sample. One exemplary parasite transport solution comprises 15 mM sodium phosphate monobasic, 15 mM sodium phosphate dibasic, 1 mM EDTA, 1 mM EGTA, and 110 mM lithium lauryl sulfate (LLS), at pH 6.7. Another exemplary parasite transport solution comprises an aqueous solution of 100 mM TRIS, 30 mM magnesium chloride, and 6% (v/v) LLS, at pH 7.5. A further exemplary parasite transport solution comprises an aqueous solution of 14 mM sodium bicarbonate, 250 mM ammonium chloride, 5% (v/v) LLS, and 0.1 mM EDTA, at a pH of 7.4. Other formulations of parasite transport solutions may function equally well.

"Target Capture Reagent" generally refers to a solution containing a number of components that facilitate capture of a nucleic acid from a solution. One exemplary Target Capture Reagent comprises 250 mM HEPES, 310 mM lithium hydroxide, 1.88 M lithium chloride, 100 mM EDTA, at pH 6.4, and 250 µg/ml of magnetic particles (1 micron SERA-MAG™ MG-CM particles, GE Healthcare Lifesciences) with $dT_{14}$ oligomers covalently bound thereto. Another exemplary Target Capture Reagent comprises 790 mM HEPES, 453 mM lithium hydroxide, 10% w/v LLS, 230 mM Succinic Acid, 0.03% w/v Foam Ban MS-575, and 0.0125% w/v of magnetic particles (1 micron SERA-MAG™ MG-CM particles, GE Healthcare Lifesciences) with $dT_{14}$ oligomers covalently bound. Other formulations of Target Capture Reagent may function equally as well.

"Wash Solution" generally refers to a solution containing 10 mM HEPES, 150 mM sodium chloride, 6.5 mM sodium hydroxide, 1 mM EDTA, 0.3% (v/v) ethanol, 0.02% (w/v)

methyl paraben, 0.01% (w/v) propyl paraben, and 0.1% (w/v) sodium lauryl sulfate, at pH 7.5.

"Probe Reagent" generally refers to a solution containing one or more labeled detection probes. One exemplary Probe Reagent is a solution made up of from about 75 to about 100 mM lithium succinate, 2% (w/v) LLS, 15 mM mercapto-ethanesulfonate, 1.2 M lithium chloride, 20 mM EDTA, and 3% (v/v) ethanol, at pH 4.7. Another exemplary Probe Reagent is a solution made up of from about 75 to about 100 mM succinic acid, 3.5% (w/v) LLS, 75 mM lithium hydroxide, 15 mM aldrithiol-2, 1.0 M lithium chloride, 1 mM EDTA, and 3.0% (v/v) ethanol, at pH 4.1-4.3. Other formulations may perform equally as well.

"Amplification Reagent" generally refers to a concentrated mixture of reaction components to facilitate amplification reactions. An Amplification Reagent will comprise a number of different reagents at various concentrations depending on factors such as for example amplification type (PCR, TMA, etc.), target nucleic acids (GC content), and the like. One exemplary Amplification Reagent comprises 47.6 mM Na-HEPES, 12.5 mM N-acetyl-L-cysteine, 2.5% TRITON™ X-100, 54.8 mM KCl, 23 mM $MgCl_2$, 3 mM NaOH, 0.35 mM of each dNTP (dATP, dCTP, dGTP, dTTP), 7.06 mM rATP, 1.35 mM rCTP, 1.35 mM UTP, 8.85 mM rGTP, 0.26 mM Na2EDTA, 5% v/v glycerol, 2.9% trehalose, 0.225% ethanol, 0.075% methylparaben, 0.015% propylparaben, and 0.002% Phenol Red, at pH 7.5-7.6. Another exemplary Amplification Reagent comprises 19.1 mM Trizma Base, 7.5 mM Trizma Hydrochloride, 23.3 mM KCl, 21.5 mM $MgCl_2$, 1 mM of each dNTP (dATP, dCTP, dGTP, dTTP), 6.5 mM rATP, 4.0 mM rCTP, 4.0 mM UTP, 6.5 mM rGTP, 3.33% v/v glycerol, 0.05 mM Zinc Acetate, 6 ppm Pro Clin 300 preservative, at pH 8.25-8.45. Other formulations of amplification reagent may function equally well. Primers may be added to the amplification reagent or added to amplification reactions separate from the amplification reagent. Enzymes in an amplification reagent can include one or more of Moloney Murine Leukemia Virus Reverse Transcriptase (MMLV-RT) and bacteriophage T7 RNA polymerase for which units are functionally defined as: 1 U of MMLV-RT incorporates 1 nmol of dTTP in 10 min at 37° C. using 200-400 micromolar oligo dT-primed poly(A) as template, and 1 U of T7 RNA polymerase incorporates 1 nmol of ATP into RNA in 1 hr at 37° C. using a DNA template containing a T7 promoter.

"Hybridization Reagent" generally refers to a solution made up of reagents having concentrations in the range of about: 75-100 mM succinic acid, 2%-3.5% (w/v) LLS, 75-100 mM lithium hydroxide, 14-16 mM aldrithiol-2, 1.0-1.2 M lithium chloride, 20-1000 mM EDTA, and 2.0-4.0% (v/v) ethanol, at pH 4-5 Other formulations for a Hybridization Reagent may function equally well.

"Selection Reagent" generally refers to a solution containing 600 mM boric acid, 182.5 mM sodium hydroxide, 1% (v/v) octoxynol (TRITON® X-100), at pH 8.5.

"Detection Reagents" include "Detect Reagent I," which generally refers to a solution containing 1 mM nitric acid and 32 mM hydrogen peroxide, and "Detect Reagent II," which generally refers to a solution of 1.5 M sodium hydroxide.

Example 1

Primer screening was performed using Transcription-Mediated Amplification (TMA) on the manual Procleix Enhanced Semi-automated System (eSAS) using *Plasmodium falciparum* in vitro transcript (IVT). An assay rack consisted of 10 rows of Ten-tube units (TTUs). Seventy five microliters (75 μL) of Amplification Reagent and 5 picomoles of each T7 promoter provider oligonucleotide and non-T7 primer oligonucleotide were added to the appropriate tubes on the rack such that each combination of amplification oligomers were tested with three replicates of *P. falciparum* IVT at 30 and 10 copies per reaction and two replicates of *B. microti* IVT at 1,000,000 copies per reaction, where applicable. *B. microti* was included in initial screening as a cross reactivity specimen due to the conserved regions between *Babesia* and *Plasmodium*. It is necessary to determine that amplification and detection systems are specific to *Plasmodium*. To achieve the target copies per reaction, 10 μL of *P. falciparum* IVT at 3 c/μL or 1 c/μL diluted in a buffer was spiked into the appropriate tubes, and 10 μL of *B. microti* IVT at 100,000 c/μL diluted in a buffer were spiked into the appropriate tubes. Various combinations of primers were tested. This set-up allows for 10 primer combinations to be tested per rack. Once the primer combinations and IVTs were spiked, 200 μL of oil was added to each tube and then the rack was covered with sealing cards and vortexed for a minimum of 20 seconds.

The rack was then incubated in a water bath at 60±1° C. for 10±1 minutes followed by incubation in a 41.5±1° C. water bath between 9 and 20 minutes. While the rack remained in the water bath, the sealing cards were removed and 25 μL of commercially available Procleix Ultrio Plus enzyme reagent (Grifols Diagnostic Solutions Inc.) was added to each reaction tube and then covered again with sealing cards. The rack was gently shaken to mix and then covered again with sealing cards and incubated for another 60±5 minutes in the 41.5±1° C. water bath.

After incubation completed, the rack was transferred to the hybridization protection assay (HPA) area where the sealing cards were removed. 100 μL of Probe reagent consisting of an Acridinium-Ester (AE) labeled probe added at a total desired concentration of at least 2.5e6 Relative Light Units (RLU) per reaction to a Hybridization reagent. Probe reagent was then added to the appropriate reaction tubes. The tubes were covered with sealing cards and the rack was vortexed for a minimum of 20 seconds after which the rack was incubated in a water bath at 61±2° C. for 15±1 minutes.

The rack was removed from the water bath, the sealing cards removed, and 250 μL of commercially available Procleix Ultrio Plus Selection reagent (Grifols Diagnostic Solutions Inc.) was added to each tube. The tubes were covered with sealing cards and vortexed for a minimum of 20 seconds and then returned to the 61±2° C. water bath and incubated for 10±1 minutes. After incubation, the rack was allowed to cool in a 23±4° C. water bath for a minimum of 10 minutes.

For detection the TTUs are removed from the rack and loaded on to the automated Leader instrument for subsequent light off using commercially available Procleix Auto Detect 1 and 2 reagents (Grifols Diagnostic Solutions Inc.) and the results were exported for analysis of the signal in Relative Light Units (RLU).

AE-labeled probes screened in this example are shown in Table 4 below. Probes were screened with amplification oligomer pairs in four experimental groups: Group 1, Groups 2a and 2b, and Group 3.

TABLE 4

| Probe # | SEQ ID NO: | 2MeAE linker site |
|---------|-----------|-------------------|
| 1 | 159 | 7, 8 |
| 3 | 159 | 9, 10 |
| 4 | 151 | 6, 7 |
| 5 | 151 | 7, 8 |
| 6 | 151 | 8, 9 |
| 7 | 150 | 8, 9 |
| 8 | 155 | 7, 8 |
| 12 | 160 | 13, 14 |
| 14 | 147 | 11, 12 |
| 15 | 157 | 10, 11 |
| 16 | 156 | 10, 11 |
| 20 | 158 | 6, 7 |

TABLE 4-continued

| Probe # | SEQ ID NO: | 2MeAE linker site |
|---------|-----------|-------------------|
| 21 | 158 | 7, 8 |
| 22 | 158 | 10, 11 |

Group 1. Probes 1, 3, 4-6, 12, and 14-16 were each tested with SEQ ID NO: 59 (T7 promoter provider oligomer) and SEQ ID NO: 30 (non-T7 oligomer). The results of this probe screen are shown in Table 5 below. Candidates showed no cross-reactivity with *B. microti* IVT at 1e6 copies per reaction. In addition, probes having the same nucleotide sequence but with different 2MeAE linker sites (see, e.g., probes 1 and 3; see also probes 4, 5, and 6) performed well irrespective of their different labelling.

TABLE 5

| | P. fal 30 c/rxn | P. fal 30 c/rxn | P. fal 30 c/rxn | P. fal 10 c/rxn | P. fal 10 c/rxn | P. fal 10 c/rxn | B. mic 1e6 c/rxn | B. mic 1e6 c/rxn | B. mic 1e6 c/c/rxn |
|---|---|---|---|---|---|---|---|---|---|
| Probe 1 | 1,222,972 | 1,157,299 | 1,201,553 | 927,342 | 1,093,944 | 98,711 | 919 | 985 | 871 |
| Probe 3 | 1,179,477 | 1,192,980 | 1,155,140 | 1,130,568 | 854,803 | 1,206,816 | 1,515 | 1,640 | 1,708 |
| Probe 5 | 816,162 | 815,694 | 774,947 | 708,438 | 745,288 | 519,080 | 1,562 | 1,253 | 1,322 |
| Probe 4 | 965,152 | 1,019,364 | 1,043,712 | 767,525 | 957,437 | 905,300 | 1,203 | 1,565 | 1,276 |
| Probe 6 | 1,179,590 | 1,182,350 | 1,136,391 | 1,034,114 | 1,098,623 | 856,584 | 2,211 | 3,484 | 2,473 |
| Probe 12 | 1,801,146 | 1,739,366 | 1,606,426 | 698,553 | 1,610,398 | 1,515,342 | 1,540 | 1,278 | 2,523 |
| Probe 14 | 1,017,636 | 997,356 | 1,015,960 | 951,505 | 830,243 | 909,076 | 870 | 865 | 1,470 |
| Probe 15 | 1,116,536 | 1,203,192 | 1,038,531 | 1,093,438 | 958,900 | 891,744 | 1,174 | 1,019 | 1,803 |
| Probe 16 | 182,425 | 195,626 | 73,184 | 141,723 | 47,725 | 52,841 | 4,155 | 2,440 | 2,629 |

| NEG | Probe 1 | | | Probe 3 | | | Probe 4 | | |
|---|---|---|---|---|---|---|---|---|---|
| | 1,108 | 1,046 | 1,310 | 1,935 | 1,749 | 1,784 | 1,319 | 1,489 | 1,388 |
| | Probe 4 | | | Probe 6 | | | Probe 12 | | |
| | 2,614 | 1,194 | 2,321 | 2,673 | 2,935 | 4,364 | 1,473 | 1,474 | 2,528 |
| | Probe 14 | | | Probe 15 | | | Probe 16 | | |
| | 1,311 | 1,597 | 978 | 1,359 | 1,171 | 1,475 | 3,940 | 1,430 | 1,869 |

Groups 2a and 2b. In Group 2a, the following primer/probe combinations were tested: each of probes 8 and 20-22 paired with SEQ ID NO: 59 and SEQ ID NO: 33 (T7/NT7), each of probes 7 and 20-22 paired with SEQ ID NO: 59 and SEQ ID NO: 52 (T7/NT7), and each of probes 7 and 8 paired with SEQ ID NO: 59 and SEQ ID NO: 49 (T7/NT7). In Group 2b, the following primer/probe combinations were tested: each of probes 20-22 paired with SEQ ID NO: 66 and SEQ ID NO: 33 (T7/NT7), each of probes 7 and 20-22 paired with SEQ ID NO: 66 and SEQ ID NO: 52 (T7/NT7), and probe 7 paired with SEQ ID NO: 66 and SEQ ID NO: 49 (T7/NT7).

The results of this probe screen are shown in Tables 6 and 7 below. Systems with the non-T7 oligomer of SEQ ID NO: 52 did not amplify *Plasmodium*. While systems with the T7/NT7 oligomer pair of SEQ ID NO: 59/SEQ ID NO: 33 paired with any of Probes 20-22 did not detect *Plasmodium*, these probes detect *Plasmodium* when used with the T7/NT7 oligomer pair of SEQ ID NO: 66/SEQ ID NO: 33.

TABLE 6

| T7/NT7 + Probe | P. fal 30 c/rxn | P. fal 30 c/rxn | P. fal 30 c/rxn | P. fal 10 c/rxn | P. fal 10 c/rxn | P. fal 10 c/rxn | B. mic 1e6 c/rxn | B. mic 1e6 c/rxn | NEG | NEG |
|---|---|---|---|---|---|---|---|---|---|---|
| 59/49 + Probe 7 | 1,414,377 | 1,429,342 | 1,423,366 | 1,293,402 | 1,271,942 | 1,347,111 | 1,967 | 1,113 | 1,651 | 1,603 |
| 59/52 + Probe 7 | 15,998 | 92,089 | 4,310 | 676 | 1,465 | 3,151 | 1,473 | 3,105 | 793 | 1,315 |
| 59/49 + Probe 8 | 1,556,915 | 1,585,955 | 1,594,418 | 1,523,106 | 1,419,616 | 1,564,211 | 7,048 | 2,935 | 3,710 | 5,601 |
| 59/33 + Probe 8 | 1,026,164 | 1,188,939 | 1,511,173 | 1,022,388 | 1,030,495 | 421,293 | 2,804 | 2,963 | 4,303 | 6,879 |
| 59/33 + Probe 20 | 438,708 | 543,560 | 635,481 | 385,704 | 410,210 | 728,374 | 1,263 | 1,475 | 1,151 | 1,295 |
| 59/52 + Probe 20 | 1,058 | 1,196 | 875 | 9,308 | 69,190 | 686 | 926 | 930 | 1,169 | 1,771 |
| 59/33 + Probe 21 | 1,131,775 | 1,206,597 | 957,441 | 1,558 | 260,318 | 653,321 | 1,217 | 3,177 | 1,160 | 2,281 |
| 59/52 + Probe 21 | 2,260 | 8,505 | 1,529 | 901 | 1,109 | 2,917 | 1,314 | 1,386 | 1,911 | 1,978 |
| 59/33 + Probe 22 | 475,040 | 486,044 | 474,661 | 342,995 | 713 | 427,613 | 1,257 | 729 | 585 | 1,143 |
| 59/52 + Probe 22 | 53,691 | 57,052 | 1,205 | 1,225 | 2,526 | 2,948 | 4,203 | 677 | 5,728 | 1,344 |

TABLE 7

| T7/NT7 + Probe | P. fal 30 c/rxn | P. fal 30 c/rxn | P. fal 30 c/rxn | P. fal 10 c/rxn | P. fal 10 c/rxn | P. fal 10 c/rxn | B. mic 1e6 c/rxn | B. mic 1e6 c/rxn | NEG | NEG |
|---|---|---|---|---|---|---|---|---|---|---|
| 66/49 + Probe 7 | 1,697,508 | 1,654,623 | 1,702,775 | 1,632,642 | 1,670,622 | 1,710,421 | 4,352 | 6,899 | 1,718 | 780 |
| 66/52 + Probe 7 | 698,772 | 9,692 | 1,394,770 | 1,732 | 926 | 198,284 | 3,588 | 4,249 | 1,173 | 890 |
| 66/33 + Probe 20 | 2,085,094 | 1,917,183 | 1,977,048 | 2,166,352 | 1,898,001 | 1,529,882 | 1,294 | 1,645 | 2,378 | 1,368 |
| 66/52 + Probe 20 | 5,387 | 6,054 | 1,395,984 | 78,381 | 13,600 | 1,825 | 2,979 | 5,688 | 5,636 | 2,165 |
| 66/33 + Probe 21 | 2,787,188 | 2,641,943 | 2,691,394 | 2,189,645 | 1,834,205 | 2,528,971 | 5,627 | 3,547 | 3,817 | 4,417 |
| 66/52 + Probe 21 | 103,016 | 1,944,005 | 8,745 | 2,694,902 | 1,167,241 | 5,856 | 3,229 | 4,437 | 6,515 | 2,704 |
| 66/33 + Probe 22 | 1,976,930 | 2,048,269 | 2,206,921 | 2,248,244 | 1,576,131 | 1,897,000 | 1,619 | 5,010 | 2,252 | 2,978 |
| 66/52 + Probe 22 | 314,430 | 1,222,503 | 36,814 | 1,596 | 60,021 | 110,944 | 1,831 | 2,930 | 2,213 | 1,337 |

Group 3. Re-designs of the non-T7 primer of SEQ ID NO: 33 were tested. Each of probes 7 and 8 were paired with each of SEQ ID NO: 66/SEQ ID NO: 25 and SEQ ID NO: 66/SEQ ID NO: 35 (T7/NT7). In addition, probe 20 was paired with SEQ ID NO: 66/SEQ ID NO: 33 (T7/NT7).

The results of this probe screen are shown in Table 8 below. The T7/NT7 oligomer pair of SEQ ID NO: 66/SEQ ID NO: 33 performed well with probe 20. Redesigns for the non-T7 oligomer of SEQ ID NO: 33 (SEQ ID NO: 25 and SEQ ID NO: 35) induced false positives with probes 7 and 8.

TABLE 8

| T7/NT7 + Probe | P. fal 30 c/rxn | P. fal 30 c/rxn | P. fal 30 c/rxn | P. fal 10 c/rxn | P. fal 10 c/rxn | P. fal 10 c/rxn | NEG | NEG | NEG | NEG |
|---|---|---|---|---|---|---|---|---|---|---|
| 66/33 + Probe 20 | 2,259,738 | 2,251,254 | 2,259,806 | 2,193,185 | 2,229,852 | 2,305,634 | 10,987 | 2,278 | 2,517 | 833 |
| 66/25 + Probe 7 | 1,639,345 | 1,634,590 | 1,094,963 | 1,577,109 | 1,447,969 | 1,443,799 | 659,001 | 907,064 | 955,394 | 106,595 |
| 69/25 + Probe 7 | 1,604,438 | 1,518,505 | 1,606,930 | 1,473,808 | 1,431,398 | 1,542,777 | 873,665 | 963,803 | 849,156 | 705,831 |
| 66/35 + Probe 7 | 1,590,743 | 1,608,076 | 1,615,693 | 1,595,727 | 1,351,299 | 1,582,092 | 759,553 | 622,876 | 495,724 | 743,057 |
| 69/35 + Probe 7 | 1,669,062 | 1,684,886 | 1,610,911 | 1,604,953 | 1,279,697 | 1,584,979 | 816,245 | 874,237 | 467,269 | 1,302,044 |
| 66/25 + Probe 8 | 1,690,077 | 1,673,850 | 1,597,686 | 1,601,896 | 1,359,389 | 1,572,372 | 1,172,325 | 693,937 | 286,919 | 536,015 |
| 69/25 + Probe 8 | 1,607,570 | 1,637,678 | 1,622,369 | 1,613,782 | 1,538,278 | 1,613,946 | 93,383 | 1,029,827 | 1,213,750 | 1,192,320 |
| 66/35 + Probe 8 | 1,622,258 | 1,609,624 | 1,572,273 | 1,600,610 | 1,570,232 | 1,611,927 | 1,235,255 | 947,640 | 841,628 | 1,143,229 |
| 69/35 + Probe 8 | 1,623,329 | 1,679,140 | 1,634,462 | 1,628,953 | 1,509,017 | 1,583,660 | 604,251 | 705,198 | 1,259,683 | 966,102 |

Example 2

This example describes materials and methods for screening of candidate amplification systems using TMA on the full automated Procleix Panther system (Grifols Diagnostic Solutions Inc.).

Specimens included P. falciparum, P. knowlesi, P. malariae, P. ovale, and/or P. vivax IVT diluted in buffer. Specimens may also include B. microti IVT as a cross-reactivity specimen. It is necessary to determine that amplification and detection systems are specific to Plasmodium. An assay calibrator comprising a P. falciparum IVT panel at 500 c/mL was included to determine the analyte cutoff for the run. The assay software uses the analyte cutoff to determine if samples are reactive or non-reactive. Samples with a signal to cutoff ratio of ≥1 are considered reactive, while those <1 are non-reactive. Assay Reagents used included the following: a Target Capture Reagent (TCR) comprising of at least one target capture oligomer (TCO); an Amplification reagent comprising at least one T7 promoter provider and at least one non-T7 primer; a Probe reagent consisting of at least one AE labeled probe; Ultrio Plus Enzyme reagent; and Selection reagent.

Example 3: Plasmodium Target Capture Probe Screening

Candidate target capture probes (TCOs) were screened with samples containing P. falciparum IVT at 500 c/mL prepared in 3 mL Parasite Transport Medium (PTM; 100 mM TRIS, 30 mM magnesium chloride, and 6% (v/v) LLS, at pH 7.5) with 1 mL whole blood. TMA reactions were performed on the fully automated Procleix Panther system substantially as described in Example 2. TCOs of SEQ ID NOs. 1-5, 7, 9, and 10 were tested in reactions using T7 oligomers of SEQ ID NO: 66 and SEQ ID NO: 69 (5 pmol/rxn each), non-T7 oligomers of SEQ ID NO: 21 and SEQ ID NO: 30 (5 pmol/rxn each), and detection probes of SEQ ID NO: 148 and SEQ ID NO: 152 (1.9e6 RLU/rxn each).

Results are shown in Tables 9 and 10 below. Assay performance was best with TCOs SEQ ID NO: 9 and SEQ ID NO: 10. SEQ ID NO: 3 was not optimal in this assay.

TABLE 9

| TCO | Mean Total RLU* |
|---|---|
| SEQ ID NO: 3 | 663,034 |
| SEQ ID NO: 1 | 873,914 |
| SEQ ID NO: 9 | 1,474,284 |
| SEQ ID NO: 2 | 985,039 |
| SEQ ID NO: 10 | 1,455,387 |
| SEQ ID NO: 7 | 793,219 |
| SEQ ID NO: 5 | 951,504 |
| SEQ ID NO: 4 | 952,023 |

*N = 10 for all TCOs except SEQ ID NO: 3 (N = 20)

TABLE 10

| TCO | % CV Total RLU* |
|---|---|
| SEQ ID NO: 3 | 19.2 |
| SEQ ID NO: 1 | 19.7 |
| SEQ ID NO: 9 | 2.6 |
| SEQ ID NO: 2 | 11.2 |
| SEQ ID NO: 10 | 3.6 |
| SEQ ID NO: 7 | 28.1 |
| SEQ ID NO: 5 | 14.4 |
| SEQ ID NO: 4 | 14.4 |

*N = 10 for all TCOs except SEQ ID NO: 3 (N = 20)

Example 4: Analytical Sensitivity—LoD of RNA Copies/mL

Limit of detection (LoD) for a candidate amplification system was assessed by probit analysis using in vitro synthesized transcripts for *P. falciparum*, *P. knowlesi*, *P. malariae*, *P. ovale*, and *P. vivax*. TMA reactions were performed on the fully automated Procleix Panther system substantially as described in Example 2. The IVT for each species was serially diluted in buffer to 100, 30, 10, 3, 1 and 0 copies/mL and tested in 32 replicates for each level per species. Specimens were tested using TMA on the fully automated Procleix Panther system (Grifols Diagnostic Solutions Inc.). An assay calibrator comprising a *P. falciparum* IVT panel at 500 c/mL was included to determine the analyte cutoff for the run. The assay software uses the analyte cutoff to determine if samples are reactive or nonreactive. Samples with a signal to cutoff ratio of $\geq 1$ are considered reactive, while those <1 are non-reactive. For this assay, the following oligomers were used: T7 oligomers of SEQ ID NO: 66 and SEQ ID NO: 69 (5 pmol/rxn each), non-T7 oligomers of SEQ ID NO: 21 and SEQ ID NO: 30 (5 pmol/rxn each), detection probes of SEQ ID NO: 148 and SEQ ID NO: 152 (1.9e6 RLU/rxn each), and TCOs of SEQ ID NO: 9 and SEQ ID NO: 10.

Results are shown in Table 11 below. Similar LoD values were observed for the five species tested. 95% LoD ranged from 9.4 to 14.8 copies/mL.

TABLE 11

| In vitro transcript (N = 32) | 50% LoD in Copies/mL (Fiducial Limits) | 95% LoD Copies/mL (Fiducial Limits) |
|---|---|---|
| *P. falciparum* | 2.1 (1.3-2.9) | 9.4 (6.5-17.3) |
| *P. knowlesi* | 3.3 (2.2-4.5) | 14.8 (10.2-27.3) |
| *P. malariae* | 3.3 (2.2-4.4) | 13.1 (9.1-24.4) |
| *P. ovale* | 2.5 (1.5-3.5) | 13.6 (9.0-27.8) |
| *P. vivax* | 4.5 (3.4-5.7) | 11.6 (8.9-17.7) |

Example 5: Analytical Sensitivity—LoD of RNA Parasites/mL

Limit of detection (LoD) for a candidate amplification system was assessed by probit analysis using cultured parasite-infected cells. Specifically, conditions were tested using a lysed negative whole blood specimen and diluted cultured *P. falciparum*-infected erythrocytes. The cultured sample was received with a known percent parasitemia and RBC count determined by Fluorescence-Activated Cell Sorting (FACS) to estimate the concentration (parasite per mL value). Based upon the estimated parasite per mL value, the sample was diluted in normal negative human whole blood to an estimated 6, 4, 2, 1, and 0.5 parasites per mL. The diluted *Plasmodium*-infected whole blood was lysed at a ratio of 0.9 mL of whole blood in 2.7 mL of Parasite Transport Medium (PTM; 100 mM TRIS, 30 mM magnesium chloride, and 6% (v/v) LLS, at pH 7.5). Specimens were tested using TMA on the fully automated Procleix Panther system (Grifols Diagnostic Solutions Inc.). An assay calibrator comprising a *P. falciparum* IVT panel at 500 c/mL was included to determine the analyte cutoff for the run. The assay software uses the analyte cutoff to determine if samples are reactive or non-reactive. Samples with a signal to cutoff ratio of $\geq 1$ are considered reactive, while those <1 are non-reactive. Assay reagents used included the following: a Target Capture Reagent (TCR) comprising TCOs of SEQ ID NO: 9 and SEQ ID NO: 10; an Amplification reagent comprising T7 oligomers of SEQ ID NO: 66 and SEQ ID NO: 69 (5 pmol/rxn each), non-T7 oligomers of SEQ ID NO: 21 and SEQ ID NO: 30 (5 pmol/rxn each); a Probe reagent comprising AE-labeled detection probes of SEQ ID NO: 148 and SEQ ID NO: 152 (1.9e6 RLU/rxn each); Ultrio Plus Enzyme reagent; and Selection reagent.

Results are shown in Table 12 below. 95% LoD was 2.14 parasites/mL. 480 replicates each of internal control buffer, PTM, and negative lysate were evaluated with no false positives (0/1,440).

TABLE 12

| | 50% LoD in Parasites/mL (Fiducial Limits) | 95% LoD in Parasites/mL (Fiducial Limits) |
|---|---|---|
| *P. falciparum* | 0.35 (0.14-0.56) | 2.14 (1.38-5.17) |

Example 6: Interference and Cross-Reactivity with *Babesia*

Interference and cross-reactivity with *Babesia microti* (a homologous protozoan) was assessed using in vitro synthesized transcripts. Testing was performed in TMA reactions performed on the fully automated Procleix Panther system substantially as described in Example 2, with *P. falciparum* IVT dilutions between 100-1 c/mL with and without the addition of *B. microti* IVT at 1e6 c/mL. The following oligomers were used: T7 oligomers of SEQ ID NO: 71 and SEQ ID NO: 72 (5 pmol/rxn each), non-T7 oligomers of SEQ ID NO: 34 and SEQ ID NO: 53 (5 pmol/rxn each), AE-labeled detection probes of SEQ ID NO: 148 and SEQ ID NO: 157 (1.9e6 RLU/rxn each), and TCOs of SEQ ID NO: 9 and SEQ ID NO: 10.

Results are shown in Tables 13 and 14 below. Comparable reactivity and analyte RLU was observe for *P. falciparum* IVT with and without the presence of *B. micron* IVT.

TABLE 13

| | | P. falciparum (copies) | | | | | |
|---|---|---|---|---|---|---|---|
| | | 100 | 30 | 10 | 3 | 1 | 0 |
| % Reactive (N = 24) | Control | 100 | 100 | 100 | 58 | 17 | 0 |
| | Presence of B. microti | 100 | 100 | 96 | 58 | 17 | 0 |

TABLE 14

| | | P. falciparum (copies) | | | | | |
|---|---|---|---|---|---|---|---|
| | | 100 | 30 | 10 | 3 | 1 | 0 |
| Mean RLU (N = 24) | Control | 2,043,991 | 2,031,427 | 1,993,527 | 1,992,755 | 2,001,796 | 2,518 |
| | Presence of B. microti | 2,055,344 | 2,029,613 | 1,925,711 | 1,777,978 | 1,815,085 | 855 |

Example 7: Evaluation of Redundant Probes

Redundant probe combinations were assessed using in vitro synthesized transcripts. Testing was performed in TMA reactions performed on the fully automated Procleix Panther system substantially as described in Example 2. The following oligomers were used: (i) T7 oligomers of SEQ ID NO: 71 and SEQ ID NO: 72 (5 pmol/rxn each), (ii) non-T7 oligomers of SEQ ID NO: 34 and SEQ ID NO: 53 (5 pmol/rxn each), (iii) AE-labeled detection probes of SEQ ID NO: 148 (4,5 2MeAE linker) and SEQ ID NO: 157 (1.27e6 RLU/rxn each) with either SEQ ID NO: 148 (5,6 2MeAE linker) or SEQ ID NO: 148 (6,7 2MeAE linker), and (iv) TCOs of SEQ ID NO: 9 and SEQ ID NO: 10.

Results are shown in Table 15 below. "C1" refers to the probe combination containing SEQ ID NO: 148 (5,6 2MeAE linker); "C2" refers to the probe combination containing SEQ ID NO: 148 (6,7 2MeAE linker). Comparable reactivity was observed for all *Plasmodium* species at 30 and 10 c/mL with the redundant probe combinations. Consistent with results in Example 1, probes having the same nucleotide sequence (SEQ ID NO: 148) but with different 2MeAE linker sites performed well irrespective of their different labelling.

TABLE 15

| | | P. falciparum (copies) | | P. knowlesi (copies) | | P. malariae (copies) | | P. ovale (copies) | | P. vivax (copies) | |
|---|---|---|---|---|---|---|---|---|---|---|---|
| | | 30 | 10 | 30 | 10 | 30 | 10 | 30 | 10 | 30 | 10 |
| % Reactive | C1 | 100 | 88 | 100 | 100 | 100 | 100 | 100 | 75 | 100 | 100 |
| (N = 8) | C2 | 100 | 75 | 100 | 88 | 100 | 100 | 100 | 88 | 100 | 100 |

Example 8: Analytical Sensitivity—LoD of RNA Parasites/mL

Limit of detection (LoD) for a candidate amplification system was assessed by probit analysis using cultured *P. falciparum*-infected erythrocytes. Testing was performed in TMA reactions performed on the fully automated Procleix Panther system substantially as described in Example 5. The following oligomers were used: (i) T7 oligomers of SEQ ID NO: 71 and SEQ ID NO: 72 (5 pmol/rxn each), (ii) non-T7 oligomers of SEQ ID NO: 34 and SEQ ID NO: 53 (5 pmol/rxn each), (iii) AE-labeled detection probes of SEQ ID NO: 148 (4,5 2MeAE linker), SEQ ID NO: 157, and SEQ ID NO: 148 (5,6 2MeAE linker) (1.17e6, 7.92e5, and 2.03e6 RLU/rxn, respectively), and (iv) TCOs of SEQ ID NO: 9 and SEQ ID NO: 10.

Results are shown in Table 16 below. 95% LoD was 2.31 parasites/mL. There were no false positives in the negative specimens tested. These results are comparable to the system evaluated in Example 5 where the 95% LoD was 2.14 parasites/mL.

TABLE 16

| | 50% LoD in Parasites/mL (Fiducial Limits) | 95% LoD in Parasites/mL (Fiducial Limits) |
|---|---|---|
| P. falciparum | 0.70 (0.33-0.97) | 2.31 (1.61-5.82) |

Example 9

Primer screening was performed using procedures for a manual Biphasic Real-Time TMA Assay. For the target capture step, 400 µL of Target Capture Reagent (TCR) comprising at least 1 Target Capture Oligo (TCO) and 1 T7 promoter provider was added to a 2 mL Deep Well 96-well plate (Thermo Scientific Cat. No. 95040450), followed by 500 µL of specimen. Specimens consisted of *Plasmodium* species in vitro transcript (IVT) diluted in buffer for *Plasmodium* detection and *Babesia* species IVT diluted in buffer for *Babesia* detection. Specimens may also include *B. microti* IVT or *P. falciparum* IVT as a cross-reactivity specimen for opposing detection systems due to the conserved regions between *Babesia* and *Plasmodium*. It is necessary to determine that amplification and detection systems are specific to the analyte system. The plate was covered with a sealing card and loaded on to a Torrey Pines plate incubator and covered with the lid. Incubation steps for the Torrey Pines incubator included 7 minutes at 80° C. followed by 17 minutes at 62° C. and between 15 to 25 minutes at 25° C., respectively.

After target capture incubation steps, the plate was loaded with a deep well comb tip (Thermo Scientific Cat. No. 97002534) and placed on to a Kingfisher 96 instrument (Thermo Scientific Type 710 REF 5400500) fitted with deep well magnets. The Kingfisher instrument was additionally loaded with a wash plate consisting of a 2 mL 96-well plate (Nunc Deep Well plate Cat. No. 278752) prepared with 500 µL of commercially available Procleix Wash Buffer reagent (Grifols Diagnostic Solutions Inc.) and a second wash plate consisting of a 200 µL 96-well plate (Thermo Scientific Cat. No. 97002540) containing 200 µL of the wash buffer. For the deep well wash steps, the plate containing the hybridized TCR-sample mixture was mixed for 5 minutes before collecting magnetic beads for 20 counts and eluting for 20 seconds to the plate containing 500 μL of wash buffer. The 500 μL wash plate was mixed for 1 minute before collecting magnetic beads for 10 counts and eluting for 20 seconds to the wash plate containing 200 μL of wash buffer.

The second wash plate containing the mixture of hybridized magnetic beads and wash buffer was removed from the Kingfisher instrument, loaded with a small PCR tip comb (Thermo Scientific 97002514) and transferred to a second Kingfisher 96 instrument (Thermo Scientific Type 710 REF 5400500) fitted with PCR magnets. The Kingfisher instrument was additionally loaded with a 96-well PCR plate (Axygen Cat. No. PCR-96-HS-C) containing 30 μL of Amplification Reagent (without Phenol Red) containing at least 1 non-T7 primer (amplification plate). To transfer the hybridized magnetic beads to the amplification plate the wash plate was mixed for 5 minutes before collecting magnetic beads for 30 counts and eluting for 30 seconds to the amplification plate. The wash plate was mixed again for 1 minute before collecting magnetic beads for 30 counts and eluting for 30 seconds to the amplification plate to complete the transfer.

The amplification plate was covered with a sealing card and loaded on to a Stratagene instrument (Mx3005P Multiplex Quantitative PCR System) to incubate for 5 minutes at 43° C. The plate was transferred to a heat block set to 42° C. and uncovered to add 10 μL of commercially available Ultrio Plus Enzyme reagent (Grifols Diagnostic Solutions Inc.) and re-covered with a sealing card. The plate was mixed on the heat block for 1 minute at 1400 RMP and reloaded on the Stratagene instrument to incubate for 5 minutes at 43° C. The plate was transferred again to the heat block and uncovered to add 15 μL of Promoter reagent (Amplification Reagent without Phenol Red) containing a mixture of at least 1 T7 promoter provider and at least 1 Fluorescent labeled molecular Torch or Beacon (5'-Hexochloro-Fluorescein (HEX) for *Plasmodium* or 5'-Fluorescein (FAM) for *Babesia*) and sealed with a clear adhesive plate cover. The plate was mixed on the heat block for 1 minute at 1400 RMP and reloaded on the Stratagene for the read protocol. The read protocol consisted of incubation at 43° C. and read every 30 seconds for cycles of 120 or 150.

The raw data exported from the Stratagene instrument was analyzed using an in-house software tool. Fluorescent curves were analyzed using a threshold of 1,000 Relative Fluorescent Units (RFU). The time for specimens to meet or exceed the threshold (TTime) was determined by the software. Specimens with a TTime were considered Reactive for *Plasmodium* in the HEX channel or *Babesia* in the FAM channel. Lower TTimes indicated better performance of the tested systems. Specimens with no TTime, or under the threshold, were considered non-reactive.

In this example, combinations of molecular torch or beacon probes and amplification oligomer pairs were tested in three groups (Groups 1, 2, and 3). Tested oligomer combinations are shown in Table 17 below.

TABLE 17

| Combinations of Amplification Oligomers and Torch Probes. | | | |
| --- | --- | --- | --- |
| T7 Primer | Non-T7 Primer | Probe (Torch/Beacon) | Group |
| SEQ ID NO: 181 | SEQ ID NO: 183 | SEQ ID NO: 104 (torch) | Group 1 |
| SEQ ID NO: 181 | SEQ ID NO: 183 | SEQ ID NO: 105 (torch) | |
| SEQ ID NO: 181 | SEQ ID NO: 183 | SEQ ID NO: 106 (torch) | |
| SEQ ID NO: 181 | SEQ ID NO: 183 | SEQ ID NO: 121 (torch) | |
| SEQ ID NO: 181 | SEQ ID NO: 183 | SEQ ID NO: 107 (beacon) | |
| SEQ ID NO: 181 | SEQ ID NO: 183 | SEQ ID NO: 108 (beacon) | |
| SEQ ID NO: 181 | SEQ ID NO: 184 | SEQ ID NO: 104 (torch) | Group 2 |
| SEQ ID NO: 59 | SEQ ID NO: 51 | SEQ ID NO: 123 (torch) | Group 3 |
| SEQ ID NO: 59 | SEQ ID NO: 31 | SEQ ID NO: 123 (torch) | |
| SEQ ID NO: 59 | SEQ ID NO: 50 | SEQ ID NO: 123 (torch) | |

Group 1 Results. Probes of SEQ ID NOs: 104-107 and 121 successfully detected *Plasmodium* with fluorescent curves generating average TTimes of less than or equal to 30.69 minutes at 10 c/mL. No fluorescent curves with TTimes were generated for the probe of SEQ ID NO: 108 concluding it was unable to detect *Plasmodium*.

Group 2 Results. Amplification oligomers of SEQ ID NOs: 181 and 184 in combination with the torch probe of SEQ ID NO: 104 successfully detected *Plasmodium*, demonstrated by fluorescent curves generating TTimes of less than or equal to 20.89 minutes at 10 c/mL, and showed no cross-reactivity with *Babesia* IVT, demonstrated by the absence of a fluorescent curve with a TTime.

Group 2 Results. Non-T7 amplification oligomers of SEQ ID NOs: 51, 31, and 50 each in combination with the T7 amplification oligomer of SEQ ID NO: 59 and the torch probe of SEQ ID NO: 123 successfully detected *Plasmodium* as demonstrated by fluorescent curves generating TTimes of less than or equal to 22.82 minutes.

Example 10

A candidate amplification system was tested using Real-time TMA on the fully automated Panther system installed with Real-time Fluorometers (Hologic Inc.). Specimens consisted of *Plasmodium* species IVT diluted in buffer for *Plasmodium* detection and *Babesia* species IVT diluted in buffer for *Babesia* detection. Specimens may also include *B. microti* IVT or *P. falciparum* IVT as a cross reactivity specimen. It is necessary to determine that amplification and detection systems are specific to the analyte system. Assay Reagents used included the following: a TCR comprising of at least one TCO and one T7 promoter provider; an Amplification Reagent comprising of at least one non-T7 primer; a Promoter reagent (Amplification Reagent without Phenol Red) consisting of at least one T7 promoter provider and at least one Fluorescent labeled molecular Torch or Beacon (5'-Hexochloro-Fluorescein (HEX) for *Plasmodium* or 5'-Fluorescein (FAM) for *Babesia*); and Ultrio Plus Enzyme reagent.

For analysis of the raw data exported from the Panther system, the Panther RT-Dev Tool (Hologic Inc.) was used. Fluorescent curves were analyzed using a threshold of 1,000 Relative Fluorescent Units (RFU). The time for specimens to meet or exceed the threshold (TTime) was determined by the software. Specimens with a TTime were considered Reactive for *Plasmodium* in the HEX channel or *Babesia* in the FAM channel. Lower TTimes indicated better performance of the tested systems. Specimens with no TTime, or under the threshold, were considered non-reactive.

The oligomers tested in this example were a T7 oligomer of SEQ ID NO: 59, a non-T7 oligomer of SEQ ID NO: 30, and a torch probe of SEQ ID NO: 123. Results demonstrated detection of 8 out of 8 replicates tested at 30 c/mL of *Plasmodium* IVT and 3 out of 8 replicates tested at 10 c/mL. Fluorescent curves generated TTimes of less than or equal to 33.18 minutes for the detected replicates at 10 c/mL.

Example 11: Detection of *Plasmodium* in Clinical Specimens

Candidate amplification systems were tested using Real-time TMA on the fully automated Panther system installed with Real-time Fluorometers (Hologic Inc.). Specimens consisted of positive controls for *B. micron* and *P. falciparum* IVT diluted in buffer to 300 c/mL and a negative control consisting of negative buffer. Clinical specimens consisted of *P. falciparum* and *P. ovale* whole blood and plasma specimens. Whole blood specimens were prepared by manual addition of 100 μL to 3 mL of a lysis buffer (14 mM sodium bicarbonate, 250 mM ammonium chloride, 5% (v/v) LLS, and 0.1 mM EDTA, at a pH of 7.4). Plasma specimens were prepared by manual addition of 100 μL to 3 mL of processed human plasma. Specimens were tested on the Panther system. Assay Reagents used included the following: a TCR comprising of at least one TCO and one T7 promoter provider; an Amplification Reagent comprising of at least one non-T7 primer; a Promoter reagent (Amplification Reagent without Phenol Red) consisting of at least one T7 promoter provider and at least one Fluorescent labeled molecular Torch or Beacon (5'-Hexochloro-Fluorescein (HEX) for *Plasmodium* or 5'-Fluorescein (FAM) for *Babesia*); and Enzyme reagent.

For analysis of the raw data exported from the Panther system, the Panther RT-Dev Tool (Hologic Inc.) was used. Fluorescent curves were analyzed using a threshold of 1,000 Relative Fluorescent Units (RFU). The time for specimens to meet or exceed the threshold (TTime) was determined by the software. Specimens with a TTime were considered Reactive for *Plasmodium* in the HEX channel or *Babesia* in the FAM channel. Lower TTimes indicated better performance of the tested systems. Specimens with no TTime, or under the threshold, were considered Nonreactive.

The oligomers tested in this example were a T7 oligomer of SEQ ID NO: 59, a non-T7 oligomer of SEQ ID NO: 30, and a torch probe of SEQ ID NO: 123. Results are shown in Table 18 below. Real-time TMA results with the tested oligomers showed 100% concordance with PCR results. Based on the calibration curve generated using in vitro *Plasmodium falciparum* infected erythrocytes, the tested sample have between 7.14E6 and 2.14E8 parasites/mL in whole blood. No cross reactivity was observed with *Babesia*.

TABLE 18

| | | | Whole Blood | Plasma | | | |
|---|---|---|---|---|---|---|---|
| Sample | Organism | PCR Result (Wadsworth) | Real-time TMA #reactive/ #tested | Real-time TMA #reactive/ #tested | Whole Blood Est. # par/mL | Plasma Est. # par/mL | Relative amounts of parasites (WB/plasma) |
| 1 | *P. fal* | Positive | 4/4 | 4/4 | 2.14E+08 | 3.18E+02 | 672,841 |
| 2 | *P. fal* | Positive | 4/4 | 4/4 | 1.49E+08 | 2.63E+02 | 566,724 |
| 3 | *P. fal* | Positive | 4/4 | 4/4 | 1.11E+08 | 2.55E+03 | 43,685 |
| 4 | *P. fal* | Positive | 4/4 | 4/4 | 7.28E+07 | 4.60E+02 | 158,340 |
| 5 | *P. fal* | Positive | 4/4 | 4/4 | 5.49E+07 | 1.08E+02 | 508,948 |
| 6 | *P. fal* | Positive | 4/4 | 4/4 | 3.07E+07 | 1.96E+01 | 1,568,437 |

Caption for table: Detection of Plasmodium positive Clinical Specimens.

TABLE 18-continued

Detection of Plasmodium positive Clinical Specimens.

| Sample | Organism | PCR Result (Wadsworth) | Whole Blood Real-time TMA #reactive/ #tested | Plasma Real-time TMA #reactive/ #tested | Whole Blood Est. # par/mL | Plasma Est. # par/mL | Relative amounts of parasites (WB/plasma) |
|---|---|---|---|---|---|---|---|
| 7 | P. fal | Positive | 4/4 | 4/4 | 2.27E+07 | 2.22E+01 | 1,026,604 |
| 8 | P. fal | Positive | 4/4 | 4/4 | 1.09E+07 | 2.38E+01 | 457,997 |
| 9 | P. ova | Positive | 4/4 | 4/4 | 1.05E+07 | 3.21E+04 | 329 |
| 10 | P. fal | Positive | 4/4 | 4/4 | 7.14E+06 | 1.74E+01 | 411,025 |

Example 12

Candidate amplification systems were tested using Real-time TMA on the fully automated Panther system installed with Real-time Fluorometers (Hologic Inc.). Specimens consisted of 5 strains of *Plasmodium* infected erythrocytes: US 05 F Benin I, US 05 F Santa Lucia, US 08 F Nigeria XII, US05 F FC27/A3, and US 05 F PH1. Infected erythrocytes were provided with an estimated parasite/mL value. Each strain was serially diluted in normal negative human whole blood to estimated values of 10 parasites/mL. The diluted *Plasmodium*-infected whole blood was manually lysed at a ratio of 1 mL of whole blood in 3 mL of a lysis buffer (14 mM sodium bicarbonate, 250 mM ammonium chloride, 5% (v/v) LLS, and 0.1 mM EDTA, at a pH of 7.4). Specimens were tested on the Panther system. Assay Reagents used included the following: a TCR comprising of at least one TCO and one T7 promoter provider; an Amplification Reagent comprising of at least one non-T7 primer; a Promoter reagent (Amplification Reagent without Phenol Red) consisting of at least one T7 promoter provider and at least one Fluorescent labeled molecular Torch or Beacon (5'-Hexochloro-Fluorescein (HEX) for *Plasmodium* or 5'-Fluorescein (FAM) for *Babesia*); and Enzyme reagent.

For analysis of the raw data exported from the Panther system, the Panther RT-Dev Tool (Hologic Inc.) was used. Fluorescent curves were analyzed using a threshold of 1,000 Relative Fluorescent Units (RFU). The time for specimens to meet or exceed the threshold (TTime) was determined by the software. Specimens with a TTime were considered Reactive for *Plasmodium* in the HEX channel or *Babesia* in the FAM channel. Lower TTimes indicated better performance of the tested systems. Specimens with no TTime, or under the threshold, were considered Nonreactive.

The oligomers tested in this example were a T7 oligomer of SEQ ID NO: 59, a non-T7 oligomer of SEQ ID NO: 30, and a torch probe of SEQ ID NO: 123. Results demonstrated that all 5 strains of *Plasmodium* infected erythrocytes were detected in 6 out of 6 replicates tested at 10 parasites/mL with fluorescent curves generating TTimes ranging from 14.29 to 17.17 minutes.

TABLE 19

Exemplary Sequences.

| SEQ ID NO: | Sequence (5' to 3') | Comments |
|---|---|---|
| 1 | GGAUUGGGUAAUUUGCGCGCCCTTTAAAAAAAAAAAAAAA AAAAAAAAAAAAAAA | Target capture oligomer |
| 2 | CAAGAAAGAGCUAUCAAUCUGUCAAUCCTTTAAAAAAAAA AAAAAAAAAAAAAAAAAAAAA | Target capture oligomer |
| 3 | CCCGUGUUGAGUCAAAUUAAGCCGCATTTAAAAAAAAAAA AAAAAAAAAAAAAAAAAA | Target capture oligomer |
| 4 | GGGUAAUUUGCGCGCCUGCUGCTTTAAAAAAAAAAAAAAA AAAAAAAAAAAAAA | Target capture oligomer |
| 5 | UUUCUCAGGCUCCCUCUCCGGAAUCGTTTAAAAAAAAAAA AAAAAAAAAAAAAAAAAA | Target capture oligomer |
| 6 | ACAUCUGAAUACGAAUGUCCCCAATTTAAAAAAAAAAAAAA AAAAAAAAAAAAAAA | Target capture oligomer |
| 7 | CUAGUCGGCAUAGUUUAUGGUUAUTTTAAAAAAAAAAAAAA AAAAAAAAAAAAAAA | Target capture oligomer |
| 8 | AAAAACGGCCAUGCAUCACCAUCCTTTAAAAAAAAAAAAAA AAAAAAAAAAAAAAAA | Target capture oligomer |
| 9 | UAGGCCAAUACCCUACCGUCCTTTAAAAAAAAAAAAAAAAA AAAAAAAAAAAA | Target capture oligomer |
| 10 | AAAGACUUUGAUUUCUCUCAAGGTTTAAAAAAAAAAAAAAA AAAAAAAAAAAAAAA | Target capture oligomer |

TABLE 19-continued

Exemplary Sequences.

| SEQ ID NO: | Sequence (5' to 3') | Comments |
|---|---|---|
| 11 | GGAUUGGGUAAUUUGCGCGCCC | THS of SEQ ID NO: 1 |
| 12 | CAAGAAAGAGCUAUCAAUCUGUCAAUCC | THS of SEQ ID NO: 2 |
| 13 | CCCGUGUUGAGUCAAAUUAAGCCGCA | THS of SEQ ID NO: 3 |
| 14 | GGGUAAUUUGCGCGCCUGCUGC | THS of SEQ ID NO: 4 |
| 15 | UUUCUCAGGCUCCCUCUCCGGAAUCG | THS of SEQ ID NO: 5 |
| 16 | ACAUCUGAAUACGAAUGUCCCCAA | THS of SEQ ID NO: 6 |
| 17 | CUAGUCGGCAUAGUUUAUGGUUA | THS of SEQ ID NO: 7 |
| 18 | AAAAACGGCCAUGCAUCACCAUCC | THS of SEQ ID NO: 8 |
| 19 | UAGGCCAAUACCCUACCGUCC | THS of SEQ ID NO: 9 |
| 20 | AAAGACUUUGAUUUCUCUCAAGG | THS of SEQ ID NO: 10 |
| 21 | AATACTACAGCATGG | Non-T7 amp oligo |
| 22 | GGAAGGCAGCAGGCGCGTA | Non-T7 amp oligo |
| 23 | AATACTACAGCATGGA | Non-T7 amp oligo |
| 24 | AATACTACAGCATGGAA | Non-T7 amp oligo |
| 25 | ATACTACAGCATGGAATA | Non-T7 amp oligo |
| 26 | ATTCAGATGTCAGAGGTGA | Non-T7 amp oligo |
| 27 | GTATTCAGATGTCAGAGGTGA | Non-T7 amp oligo |
| 28 | GTTACGATTAATAGGAGT | Non-T7 amp oligo |
| 29 | GTTACGATTAATAGGAGTA | Non-T7 amp oligo |
| 30 | GTTACGATTAATAGGAGTAG | Non-T7 amp oligo |
| 31 | GTTACGATTAATAGGAGTAGC | Non-T7 amp oligo |
| 32 | AATACTACAGCATGGAAT | Non-T7 amp oligo |
| 33 | AATACTACAGCATGGAATA | Non-T7 amp oligo |
| 34 | TACGATTAATAGGAGT | Non-T7 amp oligo |
| 35 | TACTACAGCATGGAATA | Non-T7 amp oligo |
| 36 | TATTCAGATGTCAGAGGTGA | Non-T7 amp oligo |
| 37 | TCAGTNCCTTATGAGAAATC | Non-T7 amp oligo |
| 38 | TGGCTTAGTTACGATT | Non-T7 amp oligo |
| 39 | TGGCTTAGTTACGATTAATAG | Non-T7 amp oligo |
| 40 | TTAATAGGAGTAGCTTGGGG | Non-T7 amp oligo |
| 41 | TTACGATTAATAGGAGT | Non-T7 amp oligo |
| 42 | TTCAGATGTCAGAGGTGA | Non-T7 amp oligo |
| 43 | TTGGCTTAGTTACGAT | Non-T7 amp oligo |
| 44 | TTGGCTTAGTTACGATTA | Non-T7 amp oligo |
| 45 | TTGGGGACATTCGTATTCAGA | Non-T7 amp oligo |
| 46 | TTTAGATTGCTTCCTTCAGT | Non-T7 amp oligo |
| 47 | TTTGAATACTANAGCA | Non-T7 amp oligo |

TABLE 19-continued

| | Exemplary Sequences. | |
|---|---|---|
| SEQ ID NO: | Sequence (5' to 3') | Comments |
| 48 | ACATTCGTATTCAGATGTCAG | Non-T7 amp oligo |
| 49 | CTTAGTTACGATTAATAGGA | Non-T7 amp oligo |
| 50 | CGATTAATAGGAGTAGCTTGG | Non-T7 amp oligo |
| 51 | CTTAGTTACGATTAATAGGAGTAG | Non-T7 amp oligo |
| 52 | CTTGAATACTNCAGCA | Non-T7 amp oligo |
| 53 | GGCTTAGTTACGATTA | Non-T7 amp oligo |
| 54 | AATACTANAGCATGG | Non-T7 amp oligo |
| 55 | AATACTANAGCATGGAATA | Non-T7 amp oligo |
| 56 | AATTCTAAAGAAGAGAG | Non-T7 amp oligo |
| 57 | AATTTAATACGACTCACTATAGGGAGATTCACTCCCTTAA CTTTCGTTCTTG | T7 amp oligo |
| 58 | AATTTAATACGACTCACTATAGGGAGACTTGATTAATGGA AGTATTTTAGA | T7 amp oligo |
| 59 | AATTTAATACGACTCACTATAGGGAGACTTAACTTTCGTT CTTGATTAATGGAAGT | T7 amp oligo |
| 60 | AATTTAATACGACTCACTATAGGGAGACCTACTCTTGTCT TAAACTA | T7 amp oligo |
| 61 | AATTTAATACGACTCACTATAGGGAGAAAACGGCCATGCA TCACCATCCAAGA | T7 amp oligo |
| 62 | AATTTAATACGACTCACTATAGGGAGACTCCCTTAACTTT CGTTCTTGATTAATGGAAGT | T7 amp oligo |
| 63 | AATTTAATACGACTCACTATAGGGAGACGACGGTATCTGA TCGTCTTCACTCCC | T7 amp oligo |
| 64 | AATTTAATACGACTCACTATAGGGAGACTTAACTTTCGTT CTTGATTAATGGAAG | T7 amp oligo |
| 65 | AATTTAATACGACTCACTATAGGGAGACTTAACTTTCGTT CTTGATTAATGGAAGTA | T7 amp oligo |
| 66 | AATTTAATACGACTCACTATAGGGAGACACTCCCTTAACT TTCGTTCTTGATTAATG | T7 amp oligo |
| 67 | AATTTAATACGACTCACTATAGGGAGACACTCCCTTAACT TTCGTTCTTGATTAATGG | T7 amp oligo |
| 68 | AATTTAATACGACTCACTATAGGGAGACTTCACTCCCTTA ACTTTCGTTCTTGATT | T7 amp oligo |
| 69 | AATTTAATACGACTCACTATAGGGAGACTTCACTCCCTTA ACTTTCGTTCTTGAT | T7 amp oligo |
| 70 | AATTTAATACGACTCACTATAGGGAGAATCGTCTTCACTC CCTTAACTTTCGTTC | T7 amp oligo |
| 71 | AATTTAATACGACTCACTATAGGGAGACTCCCTTAACTTT CGTTCTTGATTAATG | T7 amp oligo |
| 72 | AATTTAATACGACTCACTATAGGGAGATCACTCCCTTAAC TTTCGTTCTTGAT | T7 amp oligo |
| 73 | AATTTAATACGACTCACTATAGGGAGACCCTTAACTTTCG TTCTTGATTAATG | T7 amp oligo |
| 74 | AATTTAATACGACTCACTATAGGGAGACTTAACTTTCGTT CTTGATTAATG | T7 amp oligo |

TABLE 19-continued

Exemplary Sequences.

| SEQ ID NO: | Sequence (5' to 3') | Comments |
|---|---|---|
| 75 | AATTTAATACGACTCACTATAGGGAGATAACTTTCGTTCT TGATTAATG | T7 amp oligo |
| 76 | AATTTAATACGACTCACTATAGGGAGAACTCCCTTAACTT TCGTTCTTGAT | T7 amp oligo |
| 77 | AATTTAATACGACTCACTATAGGGAGATCCCTTAACTTTC GTTCTTGAT | T7 amp oligo |
| 78 | AATTTAATACGACTCACTATAGGGAGAAGGCAAATGCTTT CGCAGTTGTTNGTCT | T7 amp oligo |
| 79 | AATTTAATACGACTCACTATAGGGAGAAGGCAAATGCTTT CGCAGTTGTTTGTCT | T7 amp oligo |
| 80 | TTCACTCCCTTAACTTTCGTTCTTG | THS of SEQ ID NO: 57 |
| 81 | CTTGATTAATGGAAGTATTTTAGA | THS of SEQ ID NO: 58 |
| 82 | CTTAACTTTCGTTCTTGATTAATGGAAGT | THS of SEQ ID NO: 59 |
| 83 | CCTACTCTTGTCTTAAACTA | THS of SEQ ID NO: 60 |
| 84 | AAACGGCCATGCATCACCATCCAAGA | THS of SEQ ID NO: 61 |
| 85 | CTCCCTTAACTTTCGTTCTTGATTAATGGAAGT | THS of SEQ ID NO: 62 |
| 86 | CGACGGTATCTGATCGTCTTCACTCCC | THS of SEQ ID NO: 63 |
| 87 | CTTAACTTTCGTTCTTGATTAATGGAAG | THS of SEQ ID NO: 64 |
| 88 | CTTAACTTTCGTTCTTGATTAATGGAAGTA | THS of SEQ ID NO: 65 |
| 89 | CACTCCCTTAACTTTCGTTCTTGATTAATG | THS of SEQ ID NO: 66 |
| 90 | CACTCCCTTAACTTTCGTTCTTGATTAATGG | THS of SEQ ID NO: 67 |
| 91 | CTTCACTCCCTTAACTTTCGTTCTTGATT | THS of SEQ ID NO: 68 |
| 92 | CTTCACTCCCTTAACTTTCGTTCTTGAT | THS of SEQ ID NO: 69 |
| 93 | ATCGTCTTCACTCCCTTAACTTTCGTTC | THS of SEQ ID NO: 70 |
| 94 | CTCCCTTAACTTTCGTTCTTGATTAATG | THS of SEQ ID NO: 71 |
| 95 | TCACTCCCTTAACTTTCGTTCTTGAT | THS of SEQ ID NO: 72 |
| 96 | CCCTTAACTTTCGTTCTTGATTAATG | THS of SEQ ID NO: 73 |
| 97 | CTTAACTTTCGTTCTTGATTAATG | THS of SEQ ID NO: 74 |
| 98 | TAACTTTCGTTCTTGATTAATG | THS of SEQ ID NO: 75 |
| 99 | ACTCCCTTAACTTTCGTTCTTGAT | THS of SEQ ID NO: 76 |
| 100 | TCCCTTAACTTTCGTTCTTGAT | THS of SEQ ID NO: 77 |
| 101 | AGGCAAATGCTTTCGCAGTTGTTNGTCT | THS of SEQ ID NO: 78 |
| 102 | AGGCAAATGCTTTCGCAGTTGTTTGTCT | THS of SEQ ID NO: 79 |
| 103 | CGCGCAAGCGAGAAAGCGCG | Torch detection probe |
| 104 | GCUCGCAUUCGCGCAAGCGAGC | Torch detection probe |
| 105 | GCUUGCGAGUAUUCGCGCAAGC | Torch detection probe |
| 106 | GGCAAGCGAGAAAGUCUUGCC | Torch detection probe |
| 107 | CCGAGGUAUUCGCGCAACUCGG | Beacon detection probe |
| 108 | GGCUCACUUUCUCGCUUGGAGCC | Beacon detection probe |

TABLE 19-continued

Exemplary Sequences.

| SEQ ID NO: | Sequence (5' to 3') | Comments |
|---|---|---|
| 109 | CUGGAGACNAGCACCAGAG | Torch detection probe |
| 110 | GUCUCAUUUCUGGAGAC | Torch detection probe |
| 111 | GCCUAAAAUACUUCCUAGGC | Torch detection probe |
| 112 | CAUGGAAAUACUUCCAUG | Torch detection probe |
| 113 | CCGAGAUUUUCUGGAGACCUCGG | Beacon detection probe |
| 114 | CCGAGGCCUAAAAUACUUCCCUCGG | Beacon detection probe |
| 115 | GGGAAUUUAAAACCUUCCC | Torch detection probe |
| 116 | GGAAGGAAUUUAAAACCUUCC | Torch detection probe |
| 117 | GUGGGAAUUUAAAACCCCCAC | Torch detection probe |
| 118 | UCCAGAAAUUCUUAGAUUUUCUGGA | Torch detection probe |
| 119 | ACUCCGAACGAAAGUUAAGGGAGU | Torch detection probe |
| 120 | AGGGAGUGAAGACGAUCAUCCCU | Torch detection probe |
| 121 | UCGCGCAAGCGAGAAAGGCGCGA | Torch detection probe |
| 122 | CCGAAGUGNCUAAAAUACUUCGG | Torch detection probe |
| 123 | CACCUCAGAUGUCAGAGGUG | Torch detection probe |
| 124 | CUACCUCUAAAGAAGAGAGGUAG | Torch detection probe |
| 125 | CGCGCAAGCGAGAAAG | THS of SEQ ID NO: 103 |
| 126 | AUUCGCGCAAGCGAGC | THS of SEQ ID NO: 104 |
| 127 | GAGUAUUCGCGCAAGC | THS of SEQ ID NO: 105 |
| 128 | GGCAAGCGAGAAAGU | THS of SEQ ID NO: 106 |
| 129 | GUAUUCGCGCAA | THS of SEQ ID NO: 107 |
| 130 | ACUUUCUCGCUUG | THS of SEQ ID NO: 108 |
| 131 | CUCUGGAGACNAGCA | THS of SEQ ID NO: 109 |
| 132 | AUUUUCUGGAGAC | THS of SEQ ID NO: 110 |
| 133 | GCCUAAAAUACUUCC | THS of SEQ ID NO: 111 |
| 134 | AAAUACUUCCAUG | THS of SEQ ID NO: 112 |
| 135 | AUUUUCUGGAGAC | THS of SEQ ID NO: 113 |
| 136 | CCUAAAAUACUUC | THS of SEQ ID NO: 114 |
| 137 | GGGAAUUUAAAACC | THS of SEQ ID NO: 115 |
| 138 | GGAAUUUAAAACCUUCC | THS of SEQ ID NO: 116 |
| 139 | GUGGGAAUUUAAAACC | THS of SEQ ID NO: 117 |
| 140 | GAAAUUCUUAGAUUUUCUGGA | THS of SEQ ID NO: 118 |
| 141 | GAACGAAAGUUAAGGGAGU | THS of SEQ ID NO: 119 |
| 142 | AGGGAGUGAAGACGAUCA | THS of SEQ ID NO: 120 |
| 143 | UCGCGCAAGCGAGAAAG | THS of SEQ ID NO: 121 |
| 144 | UGNCUAAAAUACUUCGG | THS of SEQ ID NO: 122 |
| 145 | CAGAUGUCAGAGGUG | THS of SEQ ID NO: 123 |

TABLE 19-continued

Exemplary Sequences.

| SEQ ID NO: | Sequence (5' to 3') | Comments |
|---|---|---|
| 146 | UCUAAAGAAGAGAGGUAG | THS of SEQ ID NO: 124 |
| 147 | UCUUAGAUUUUCUGGAGAC | Detection probe |
| 148 | UUCAGAUGUCAGAGG | Detection probe |
| 149 | UUCAGAUGUCAGAGGT | Detection probe |
| 150 | UAUUCAGAUGUCAGAGGT | Detection probe |
| 151 | UAUUCAGAUGUCAGAGGUG | Detection probe |
| 152 | UCAGAUGUCAGAGGT | Detection probe |
| 153 | UUCAGAUGUCAGAGGT | Detection probe |
| 154 | AUUCAGAUGUCAGAGGT | Detection probe |
| 155 | AUUCAGAUGUCAGAGGUG | Detection probe |
| 156 | CUUAGAUUUUCUGGAGA | Detection probe |
| 157 | CUUAGAUUUUCUGGAGAC | Detection probe |
| 158 | CUUAGUUACGAUUAAUAGGA | Detection probe |
| 159 | GUAUUCAGAUGUCAGAGGUGA | Detection probe |
| 160 | AUUCUUAGAUUUUCUGGAGAC | Detection probe |
| 161 | CUAAGAUUUUCUGGAGAC | Detection probe |
| 162 | TTTGAATACTANAGCATGGAATA | Amp oligo hybridizing region (SEQ ID NOs: 21, 23-25, 32, 33, 35, 54, & 55 are contained within here) |
| 163 | TACTANAGCA | Amp oligo core sequence (SEQ ID NOs: 21, 23-25, 32, 33, 35, 54, & 55 share this) |
| 164 | TTTGAATACTACAGCATGGAATA | Amp oligo hybridizing region (SEQ ID NOs: 21, 23-25, 32, 33, & 35 are contained within here) |
| 165 | TACTACAGCA | Amp oligo core sequence (SEQ ID NOs: 21, 23-25, 32, 33, & 35 share this) |
| 166 | TTGGCTTAGTTACGATTAATAGGAGTAGCTTGGGG | Amp oligo hybridizing region (SEQ ID NOs: 28-31, 34, 38-41, 43, 44, 49-51, & 53 are contained within here) |
| 167 | TTAATAGGAGT | Amp oligo core sequence (SEQ ID NOs: 28-31, 34, 40, 41, & 49-51 share this) |
| 168 | GGCTTAGTTACGAT | Amp oligo core sequence (SEQ ID NOs: 38, 39, 43, 44, & 53 share this) |
| 169 | CGACGGTATCTGATCGTCTTCACTCCCTTAACTTTCGTTC TTGATTAATGGAAGTATTTTAGA | Amp oligo hybridizing region (SEQ ID NOs: 80-82, & 85-100 are contained within here) |
| 170 | ATCGTCTTCACTCCCTTAACTTTCGTTCTTGATTAATGGA AGTATTTTAGA | Amp oligo hybridizing region (SEQ ID NOs: 80-82, 85, & 87-100 are contained within here) |
| 171 | CTTGATTAATG | Amp oligo core sequence (SEQ ID NOs: 81, 82, 85, 87-90, 94, & 96-98 share this) |
| 172 | TAACTTTCGTTC | Amp oligo core sequence (SEQ ID NOs: 80, 82, 85, & 87-100 share this) |

TABLE 19-continued

Exemplary Sequences.

| SEQ ID NO: | Sequence (5' to 3') | Comments |
|---|---|---|
| 173 | CTTCACTCCC | Amp oligo core sequence (SEQ ID NOs: 86 & 91-93 share this) |
| 174 | UCAGAUGUCAGAGG | Detection probe core sequence (SEQ ID NOs: 148-155 & 159 share this) |
| 175 | CUAAGAUUUUCUGGAGA | Detection probe core sequence (SEQ ID NOs: 147, 156, 157, 160, & 161 share this) |
| 176 | CAGAUGUCAGAGG | Detection probe core sequence (SEQ ID NOs: 145, 148-155, & 159 share this) |
| 177 | YUCUGGAGAC | Detection probe core sequence (SEQ ID NOs: 131, 132, 135, 147, 156, 157, 160, & 161 share this) |
| 178 | AUUUUCUGGA | Detection probe core sequence (SEQ ID NOs: 132, 135, 140, 147, 156, 157, 160, & 161 share this) |
| 179 | AATTTAATACGACTCACTATAGGGAGA | Exemplary T7 promoter sequence for use in an isothermal amplification reaction |
| 180 | aacctggttgatcttgccagtagtcatatgcttgtctcaa agattaagccatgcaagtgaaagtatatatatattttata tgtagaaactgcgaacggctcattaaaacagttatagtct acttgacattttattataaggataactacggaaaagctg tagctaatacttgctttattatcctttgatttttatcttt ggataagtatttgttaggccttataagaaaaaagttatta acttaaggaattataacaaagaagtaacacgtaataaatt tattttatttagtgtgtatcaatcgagtttctgacctatc agcttttgatgttagggtattggcctaacatggctatgac gggtaacggggaattagagttcgattccggagagggagcc tgagaaatagctaccacatctaaggaaggcagcaggcgcg taaattacccaattctaaagaagagaggtagtgacaagaa ataacaatgcaaggccaattttttggttttgtaattggaat ggtgggaatttaaaaccttcccagagtaacaattggaggg caagtctggtgccagcagccgcggtaattccagctccaat agcgtatattaaaattgttgcagttaaaacgctcgtagtt gaatttcaaagaatcgatattttattgtaactattctagg ggaactattttagctttcgctttaatacgcttcctctatt attatgttctttaaataacaaagattcttttttaaaatccc cacttttgcttttgcttttgggggattttgttactttgag taaattagagtgttcaaagcaaacagttaaagcatttact gtgtttgaatactatagcatggaataacaaaattgaacaa gctaaaattttttgttcttttttcttattttggcttagtt acgattaataggagtagcttggggacattcgtattcagat gtcagaggtgaaattcttagattttctggagacgaacaac tgcgaaagcatttgtctaaaatacttccattaatcaagaa cgaaagttaagggagtgaagacgatcagataccgtcgtaa tcttaaccataaactatgccgactaggtgttggatgaaag tgttaaaaataaaagtcatctttcgaggtgactttttagat tgcttccttcagtaccttatgagaaatcaaagtctttggg ttctggggcgagtattcgcgcaagcgagaaagttaaaaga attgacggaagggcaccaccaggcgtggagcttgcggctt aatttgactcaacacggggaaactcactagtttaagacaa gagtaggattgacagattaatagctctttcttgatttctt ggatggtgatgcatggccgttttagttcgtgaatatgat ttgtctggttaattccgataacgaacgagatcttaacctg ctaattagcggcgagtacactatattcttatttgaaattg aacataggtaactatacatttattcagtaatcaaattagg atattttattaaaatatccttttccctgttctactaata atttgtttttactctatttctctcttcttttaagaatgt acttgcttgattgaaaagcttcttagaggaacattgtgtg tctaacacaaggaagtttaaggcaacaacaggtctgtgat gtccttagatgaactaggctgcacgcgtgctcacactgata tatataacgagttttaaaaatatgcttatatttgtatct ttgcttatattttgcatacttttcctccgccgaaaggcgt aggtaatctttatcaatatatatcgtgatggggatagatt attgcaattattaatcttgaacgaggaatgcctagtaagc atgattcatcagattgtgctgactacgtccctgcccttttg | Plasmodium falciparum 3D7 18S ribosomal RNA (PF3D7_0725600), rRNA NCBI Reference Sequence: XR_002273081.2 |

TABLE 19-continued

Exemplary Sequences.

| SEQ ID NO: | Sequence (5' to 3') | Comments |
|---|---|---|
| | tacacaccgcccgtcgctcctaccgattgaaagatatgat gaattgtttggacaagaaaaattgaattatattctttttt tttctggaaaaaccgtaaatcctatcttttaaaggaagga gaagtcgtaacaaggtttccgtaggtgaacctgcggaagg atcatta | |
| 181 | AATTTAATACGACTCACTATAGGGAGATCAAGAAAGAGCT ATNAATCTGTCAATCC | T7 amp oligo |
| 182 | TCAAGAAAGAGCTATNAATCTGTCAATCC | THS of SEQ ID NO: 181 |
| 183 | GAAATCAAAGTCTTTGGGTTCTG | Non-T7 amp oligo |
| 184 | CAAAGTCTTTGGGTTCTGG | Non-T7 amp oligo |
| 185 | TTTAGATTGCTTCCTTCAGTNCCTTATGAGAAATCAAAGT CTTTGGGTTCTGG | Amp oligo hybridizing region (SEQ ID NOs: 37, 46, 183, & 184 are contained within here) |
| 186 | GAAATCAAAGTCTTTGGGTTCTGG | Amp oligo hybridizing region (SEQ ID NOs: 183 & 184 are contained within here) |
| 187 | CAAAGTCTTTGGGTTCTG | Amp oligo core sequence (SEQ ID NOs: 183 & 184 share this) |
| 188 | AAACGGCCATGCATCACCATCCAAGAAATCAAGAAAGAGC TATNAATCTGTCAATCCTACTCTTGTCTTAAACTA | Amp oligo hybridizing region (SEQ ID NOs: 83, 84, & 182 are contained within here) |
| 189 | GAGUAUUCGSGCAAGCGAGAAAGU | Detection probe hybridizing region (SEQ ID NOs: 125-130 & 143 are contained within here) |
| 190 | AUUCGCGCAA | Detection probe core sequence (SEQ ID NOs: 126, 127, & 129 share this) |
| 191 | CAAGCGAGC | Detection probe core sequence (SEQ ID NOs: 125, 126, 128, 130, & 143 share this) |
| 192 | [GenBank Accession JQ627153.1] | *Plasmodium vivax* isolate SV1 18S ribosomal RNA gene, partial sequence |
| 193 | [GenBank Accession L07560.1] | *Plasmodium knowlesi* small subunit ribosomal RNA sequence |
| 194 | [GenBank Accession AB182491.1] | *Plasmodium ovale* gene for small subunit ribosomal RNA, complete sequence, variant type 1 |
| 195 | [GenBank Accession AF487999.1] | *Plasmodium* cf. malariae type 1 small subunit ribosomal RNA gene, complete sequence |
| 196 | GUAUUCAGAUGUCAGAGGUGAAAUUCUUAGAUUYUCUGGA GACNAGCA | Detection probe hybridizing region (SEQ ID NOs: 131, 132, 135, 140, 145, 147-157 & 159-161 are contained within here) |
| 197 | GUAUUCAGAUGUCAGAGGUGAAAUUCUUAGAUUUUCUGGA GAC | Detection probe hybridizing region (SEQ ID NOs: 132, 135, 140, 145, 147-157 & 159-161 are contained within here) |

Embodiments

Embodiment 1. A method for specifically detecting *Plasmodium* species nucleic acid in a sample, said method comprising:

(1) contacting a sample, said sample suspected of containing *Plasmodium* species nucleic acid, with at least two oligomers for amplifying a target region of a *Plasmodium* species target nucleic acid, wherein the at least two amplification oligomers comprise:

(a) an amplification oligomer comprising a target-hybridizing sequence (i) that is from about 14 to about 20 contiguous nucleotides in length, is contained in the sequence of SEQ ID NO: 162, and comprises the sequence of SEQ ID NO: 163; or (ii) that is from about 14 to about 25 contiguous nucleotides in length, is contained in the sequence of SEQ ID NO: 166, and comprises the sequence of SEQ ID NO: 167 or SEQ ID NO: 168; and (b) an amplification oligomer comprising a target-hybridizing sequence that is from about 15 to about 33 contiguous nucleotides in length, is contained in SEQ ID NO: 169 and comprises the sequence of SEQ ID NO: 171, SEQ ID NO: 172, or SEQ ID NO: 173;

(2) performing an in vitro nucleic acid amplification reaction, wherein any *Plasmodium* target nucleic acid present in said sample is used as a template for generating an amplification product; and (3) detecting the presence or absence of the amplification product, thereby indicating the presence or absence of *Plasmodium* species target nucleic acid in said sample.

Embodiment 2. The method of Embodiment 1, wherein the at least two amplification oligomers comprise the amplification oligomer of (a)(i).

Embodiment 3. The method of Embodiment 2, wherein the target-hybridizing sequence of (a)(i) is selected from the group consisting of SEQ ID NOs: 21, 23-25, 32, 33, 35, 54, and 55.

Embodiment 4. The method of Embodiment 2, wherein the target-hybridizing sequence of (a)(i) is contained in the sequence of SEQ ID NO: 164 and comprises the sequence of SEQ ID NO: 165.

Embodiment 5. The method of Embodiment 4, wherein the target-hybridizing sequence of (a)(i) is selected from the group consisting of SEQ ID NOs: 21, 23-25, 32, 33, and 35.

Embodiment 6. The method of Embodiment 1, wherein the at least two amplification oligomers comprise the amplification oligomer of (a)(ii).

Embodiment 7. The method of Embodiment 6, wherein the target-hybridizing sequence of (a)(ii) comprises the sequence of SEQ ID NO: 167.

Embodiment 8. The method of Embodiment 7, wherein the target-hybridizing sequence of (a)(ii) is selected from the group consisting of SEQ ID NOs 28-31, 34, 40, 41, and 49-51.

Embodiment 9. The method of Embodiment 6, wherein the target-hybridizing sequence of (a)(ii) comprises the sequence of SEQ ID NO: 168.

Embodiment 10. The method of Embodiment 9, wherein the target-hybridizing sequence of (a)(ii) is selected from the group consisting of SEQ ID NOs: 38, 39, 43, 44, and 53.

Embodiment 11. The method of any one of Embodiments 1 to 10, wherein the target-hybridizing sequence of (b) is selected from the group consisting of SEQ ID NOs: 80-82 and 85-100.

Embodiment 12. The method of any one of Embodiments 1 to 10, wherein the target-hybridizing sequence of (b) is contained in SEQ ID NO: 170 and comprises the sequence of SEQ ID NO: 171 or SEQ ID NO: 172.

Embodiment 13. The method of Embodiment 12, wherein the target-hybridizing sequence of (b) comprises the sequence of SEQ ID NO: 171.

Embodiment 14. The method of Embodiment 13, wherein the target-hybridizing sequence of (b) is selected from the group consisting of SEQ ID NOs: 81, 82, 85, 87-90, 94, and 96-98.

Embodiment 15. The method of Embodiment 12, wherein the target-hybridizing sequence of (b) comprises the sequence of SEQ ID NO: 172.

Embodiment 16. The method of Embodiment 15, wherein the target-hybridizing sequence of (b) is selected from the group consisting of SEQ ID NOs: 80, 82, 85, and 87-100.

Embodiment 17. The method of any one of the preceding Embodiments, wherein the amplification oligomer of (b) is a promoter primer or promoter provider further comprising a promoter sequence located 5' to the target-hybridizing sequence of (b).

Embodiment 18. The method of Embodiment 17, wherein the promoter sequence is a T7 promoter sequence.

Embodiment 19. The method of Embodiment 18, wherein the T7 promoter sequence is SEQ ID NO: 179.

Embodiment 20. The method of Embodiment 19, wherein the amplification oligomer of (b) comprises a sequence selected from the group consisting of SEQ ID NOs: 57-59 and 62-77.

Embodiment 21. The method of Embodiment 1, wherein the target-hybridizing sequences of (a) and (b), respectively, are (A) SEQ ID NO: 30 and SEQ ID NO: 82;
    (B) SEQ ID NO: 33 and SEQ ID NO: 82;
    (C) SEQ ID NO: 49 and SEQ ID NO: 82;
    (D) SEQ ID NO: 21 and SEQ ID NO: 89
    (E) SEQ ID NO: 30 and SEQ ID NO: 89;
    (F) SEQ ID NO: 33 and SEQ ID NO: 89;
    (G) SEQ ID NO: 49 and SEQ ID NO: 89;
    (H) SEQ ID NO: 21 and SEQ ID NO: 92;
    (I) SEQ ID NO: 30 and SEQ ID NO: 92;
    (J) SEQ ID NO: 21 and SEQ ID NO: 94;
    (K) SEQ ID NO: 34 and SEQ ID NO: 94;
    (L) SEQ ID NO: 53 and SEQ ID NO: 94;
    (M) SEQ ID NO: 21 and SEQ ID NO: 95;
    (N) SEQ ID NO: 34 and SEQ ID NO: 95; or
    (O) SEQ ID NO: 53 and SEQ ID NO: 95.

Embodiment 22. The method of Embodiment 21, wherein the amplification oligomer of (b) is a promoter primer or promoter provider further comprising a promoter sequence located 5' to the target-hybridizing sequence of (b).

Embodiment 23. The method of Embodiment 22, wherein the promoter sequence is a T7 promoter sequence.

Embodiment 24. The method of Embodiment 23, wherein the T7 promoter sequence is SEQ ID NO: 179.

Embodiment 25. The method of Embodiment 1, wherein the at least two amplification oligomers comprise first and second amplification oligomers as in (a).

Embodiment 26. The method of Embodiment 25, wherein the at least two amplification oligomers comprise first and second amplification oligomers as in (a)(ii).

Embodiment 27. The method of Embodiment 26, wherein the first amplification oligomer as in (a)(ii) comprises a target-hybridizing sequence comprising the sequence of SEQ ID NO: 167; and the second amplification oligomer as in (a)(ii) comprises a target-hybridizing sequence comprising the sequence of SEQ ID NO: 168.

Embodiment 28. The method of Embodiment 27, wherein the first amplification oligomer comprises the target-hybridizing sequence of SEQ ID NO: 34 and the second amplification oligomer comprises the target-hybridizing sequence of SEQ ID NO: 53.

Embodiment 29. The method of Embodiment 25, wherein the at least two amplification oligomers comprise an amplification oligomer as in (a)(i) and an amplification oligomer as in (a)(ii).

Embodiment 30. The method of Embodiment 29, wherein the amplification oligomer as in (a)(i) comprises a target-hybridizing sequence that is contained in the sequence of SEQ ID NO: 164 and comprises the sequence of SEQ ID NO: 165; and the amplification oligomer as in (a)(ii) comprises the sequence of SEQ ID NO: 167.

Embodiment 31. The method of Embodiment 30, wherein the amplification oligomer as in (a)(i) comprises the target-hybridizing sequence of SEQ ID NO: 21 and the amplification oligomer as in (a)(ii) comprises the target-hybridizing sequence of SEQ ID NO: 34.

Embodiment 32. The method of any one of Embodiments 1 and 25 to 31, wherein the at least two amplification oligomers comprise first and second amplification oligomers of (b).

Embodiment 33. The method of Embodiment 32, wherein each of the first and second amplification oligomers of (b) comprises a target-hybridizing sequence that is contained in the sequence of SEQ ID NO: 170 and comprises the sequence of SEQ ID NO: 171 or SEQ ID NO: 172.

Embodiment 34. The method of Embodiment 33, wherein the first amplification oligomer as in (b) comprises the target-hybridizing sequence of SEQ ID NO: 94 and the second amplification oligomer as in (b) comprises the target-hybridizing sequence of SEQ ID NO: 95.

Embodiment 35. The method of any one of Embodiments 32 to 34, wherein each of the amplification oligomers of (b) is a promoter primer or promoter provider further comprising a promoter sequence located 5' to the target-hybridizing sequence of (b).

Embodiment 36. The method of Embodiment 35, wherein the promoter sequence is a T7 promoter sequence.

Embodiment 37. The method of Embodiment 36, wherein the T7 promoter sequence is SEQ ID NO: 179.

Embodiment 38. The method of any one of the preceding Embodiments, further comprising purifying the target nucleic acid from other components in the sample before step (1).

Embodiment 39. The method of Embodiment 38, wherein the purifying step comprises contacting the sample with at least one capture probe oligomer comprising a target-hybridizing sequence covalently attached to a sequence or moiety that binds to an immobilized probe, wherein said target-hybridizing sequence is up to about 30 contiguous nucleotides in length and comprises a sequence selected from the group consisting of SEQ ID NOs: 11-15, 17, 19, and 20, including DNA equivalents and DNA/RNA chimerics thereof.

Embodiment 40. The method of Embodiment 39, wherein the capture probe oligomer target-hybridizing sequence is selected from the group consisting of SEQ ID NOs: 11-15, 17, 19, and 20, including DNA equivalents and DNA/RNA chimerics thereof.

Embodiment 41. The method of Embodiment 39, wherein the purifying step comprises contacting the sample with at least two capture probe oligomers.

Embodiment 42. The method of Embodiment 41, wherein the at least two capture probe oligomers comprise a first capture probe oligomer comprising the target-hybridizing sequence of SEQ ID NO: 19; and a second capture probe oligomer comprising the target-hybridizing sequence of SEQ ID NO: 20.

Embodiment 43. The method of any one of the preceding Embodiments, wherein the detecting step (3) comprises contacting the in vitro nucleic acid amplification reaction with at least one detection probe oligomer comprising a target-hybridizing sequence configured to specifically hybridize to the amplification product under conditions whereby the presence or absence of the amplification product is determined, thereby indicating the presence or absence of *Plasmodium* species in said sample.

Embodiment 44. The method of Embodiment 43, wherein the detection probe oligomer target-hybridizing sequence is from about 13 to about 40 nucleotides in length and is (i) contained in the sequence of SEQ ID NO: 196 or its complement, or a DNA equivalent or DNA/RNA chimeric thereof, and (ii) comprises a sequence selected from the group consisting of SEQ ID NO: 175, SEQ ID NO: 176, SEQ ID NO: 177, and SEQ ID NO: 178, including complements, DNA equivalents, and DNA/RNA equivalents thereof.

Embodiment 45. The method of Embodiment 44, wherein the detection probe oligomer target-hybridizing sequence is selected from the group consisting of SEQ ID NOs: 131, 132, 135, 140, 145, 147-157, and 159-161, including complements, DNA equivalents, and DNA/RNA chimerics thereof.

Embodiment 46. The method of Embodiment 44, wherein the detection probe oligomer target-hybridizing sequence is (i) contained in the sequence of SEQ ID NO: 197 or its complement, or a DNA equivalent or DNA/RNA chimeric thereof, and (ii) comprises the sequence of SEQ ID NO: 174 or SEQ ID NO: 175, including complements, DNA equivalents, and DNA/RNA chimerics thereof.

Embodiment 47. The method of Embodiment 46, wherein the detection probe oligomer target-hybridizing sequence (ii) comprises SEQ ID NO: 174 or its complement, or a DNA equivalent or DNA/RNA chimeric thereof.

Embodiment 48. The method of Embodiment 47, wherein the detection probe oligomer target-hybridizing sequence is selected from the group consisting of SEQ ID NOs: 148-155 and 159, including complements, DNA equivalents, and DNA/RNA chimerics thereof.

Embodiment 49. The method of Embodiment 46, wherein the detection probe oligomer target-hybridizing sequence (ii) comprises SEQ ID NO: 175 or its complement, or a DNA equivalent or DNA/RNA chimeric thereof.

Embodiment 50. The method of Embodiment 49, wherein the detection probe oligomer target-hybridizing sequence is selected from the group consisting of SEQ ID NOs 147, 156, 157, 160, and 161, including complements, DNA equivalents, and DNA/RNA chimerics thereof.

Embodiment 51. The method of Embodiment 44, wherein the detection probe oligomer target-hybridizing sequence (ii) comprises a sequence selected from the group consisting of SEQ ID NO: 177 and SEQ ID NO: 178, including complements, DNA equivalents, and DNA/RNA chimerics thereof.

Embodiment 52. The method of Embodiment 51, wherein the detection probe oligomer target-hybridizing sequence is selected from the group consisting of SEQ ID NOs: 131, 132, 135, 140, 147, 156, 157, 160, and 161, including complements, DNA equivalents, and DNA/RNA chimerics thereof.

Embodiment 53. The method of any one of Embodiments 43 to 52, wherein the detection probe oligomer comprises a 2' methoxy modification on at least one of a nucleotide residue member of the detection probe oligomer nucleotide sequence.

Embodiment 54. The method of Embodiment 43 to 53, wherein the amplification oligomer target-hybridizing sequence of (a), the amplification oligomer target-hybridizing sequence of (b), and the detection probe oligomer target-hybridizing sequence, respectively, are (A) SEQ ID NO: 30, SEQ ID NO: 82, and SEQ ID NO: 151 or its complement, or a DNA equivalent or DNA/RNA chimeric of SEQ ID NO: 151 or its complement;

(B) SEQ ID NO: 30, SEQ ID NO: 82, and SEQ ID NO: 157 or its complement, or a DNA equivalent or DNA/RNA chimeric of SEQ ID NO: 157 or its complement;

(C) SEQ ID NO: 33, SEQ ID NO: 82, and SEQ ID NO: 155 or its complement, or a DNA equivalent or DNA/RNA chimeric of SEQ ID NO: 155 or its complement;

(D) SEQ ID NO: 49, SEQ ID NO: 82, and SEQ ID NO: 150 or its complement, or a DNA equivalent or DNA/RNA chimeric of SEQ ID NO: 150 or its complement;

(E) SEQ ID NO: 49, SEQ ID NO: 82, and SEQ ID NO: 155 or its complement, or a DNA equivalent or DNA/RNA chimeric of SEQ ID NO: 155 or its complement;

(F) SEQ ID NO: 21, SEQ ID NO: 89, and SEQ ID NO: 148 or its complement, or a DNA equivalent or DNA/RNA chimeric of SEQ ID NO: 148 or its complement;

(G) SEQ ID NO: 21, SEQ ID NO: 89, and SEQ ID NO: 152 or its complement, or a DNA equivalent or DNA/RNA chimeric of SEQ ID NO: 152 or its complement;

(H) SEQ ID NO: 30, SEQ ID NO: 89; and SEQ ID NO: 148 or its complement, or a DNA equivalent or DNA/RNA chimeric of SEQ ID NO: 148 or its complement;

(I) SEQ ID NO: 30, SEQ ID NO: 89; and SEQ ID NO: 152 or its complement, or a DNA equivalent or DNA/RNA chimeric of SEQ ID NO: 152 or its complement;

(I) SEQ ID NO: 33, SEQ ID NO: 89; and SEQ ID NO: 158 or its complement, or a DNA equivalent or DNA/RNA chimeric of SEQ ID NO: 158 or its complement;

(K) SEQ ID NO: 49, SEQ ID NO: 89, and SEQ ID NO: 150 or its complement, or a DNA equivalent or DNA/RNA chimeric of SEQ ID NO: 150 or its complement;

(L) SEQ ID NO: 21, SEQ ID NO: 92, and SEQ ID NO: 148 or its complement, or a DNA equivalent or DNA/RNA chimeric of SEQ ID NO: 148 or its complement;

(M) SEQ ID NO: 21, SEQ ID NO: 92, and SEQ ID NO: 152 or its complement, or a DNA equivalent or DNA/RNA chimeric of SEQ ID NO: 152 or its complement;

(N) SEQ ID NO: 30, SEQ ID NO: 92; and SEQ ID NO: 148 or its complement, or a DNA equivalent or DNA/RNA chimeric of SEQ ID NO: 148 or its complement;

(O) SEQ ID NO: 30, SEQ ID NO: 92; and SEQ ID NO: 152 or its complement, or a DNA equivalent or DNA/RNA chimeric of SEQ ID NO: 152 or its complement;

(P) SEQ ID NO: 21, SEQ ID NO: 94, and SEQ ID NO: 148 or its complement, or a DNA equivalent or DNA/RNA chimeric of SEQ ID NO: 148 or its complement;

(Q) SEQ ID NO: 21, SEQ ID NO: 94, and SEQ ID NO: 152 or its complement, or a DNA equivalent or DNA/RNA chimeric of SEQ ID NO: 152 or its complement;

(R) SEQ ID NO: 34, SEQ ID NO: 94, and SEQ ID NO: 148 or its complement, or a DNA equivalent or DNA/RNA chimeric of SEQ ID NO: 148 or its complement;

(S) SEQ ID NO: 34, SEQ ID NO: 94, and SEQ ID NO: 152 or its complement, or a DNA equivalent or DNA/RNA chimeric of SEQ ID NO: 152 or its complement;

(T) SEQ ID NO: 34, SEQ ID NO: 94, and SEQ ID NO: 157 or its complement, or a DNA equivalent or DNA/RNA chimeric of SEQ ID NO: 157 or its complement;

(U) SEQ ID NO: 53, SEQ ID NO: 94, and SEQ ID NO: 148 or its complement, or a DNA equivalent or DNA/RNA chimeric of SEQ ID NO: 148 or its complement;

(V) SEQ ID NO: 53, SEQ ID NO: 94, and SEQ ID NO: 152 or its complement, or a DNA equivalent or DNA/RNA chimeric of SEQ ID NO: 152 or its complement;

(W) SEQ ID NO: 53, SEQ ID NO: 94, and SEQ ID NO: 157 or its complement, or a DNA equivalent or DNA/RNA chimeric of SEQ ID NO: 157 or its complement;

(X) SEQ ID NO: 21, SEQ ID NO: 95, and SEQ ID NO: 148 or its complement, or a DNA equivalent or DNA/RNA chimeric of SEQ ID NO: 148 or its complement;

(Y) SEQ ID NO: 21, SEQ ID NO: 95, and SEQ ID NO: 152 or its complement, or a DNA equivalent or DNA/RNA chimeric of SEQ ID NO: 152 or its complement;

(Z) SEQ ID NO: 34, SEQ ID NO: 95, and SEQ ID NO: 148 or its complement, or a DNA equivalent or DNA/RNA chimeric of SEQ ID NO: 148 or its complement;

(AA) SEQ ID NO: 34, SEQ ID NO: 95, and SEQ ID NO: 152 or its complement, or a DNA equivalent or DNA/RNA chimeric of SEQ ID NO: 152 or its complement;

(AB) SEQ ID NO: 34, SEQ ID NO: 95, and SEQ ID NO: 157 or its complement, or a DNA equivalent or DNA/RNA chimeric of SEQ ID NO: 157 or its complement;

(AC) SEQ ID NO: 53, SEQ ID NO: 95, and SEQ ID NO: 148 or its complement, or a DNA equivalent or DNA/RNA chimeric of SEQ ID NO: 148 or its complement;

(AD) SEQ ID NO: 53, SEQ ID NO: 95, and SEQ ID NO: 152 or its complement, or a DNA equivalent or DNA/RNA chimeric of SEQ ID NO: 152 or its complement; or (AE) SEQ ID NO: 53, SEQ ID NO: 95, and SEQ ID NO: 157 or its complement, or a DNA equivalent or DNA/RNA chimeric of SEQ ID NO: 157 or its complement.

Embodiment 55. The method of any one of Embodiments 43 to 54, wherein the detection probe oligomer comprises a detectable label.

Embodiment 56. The method of Embodiment 55, wherein the detectable label is a chemiluminescent label or a fluorescent label.

Embodiment 57. The method of Embodiment 56, wherein the detectable label is a chemiluminescent acridinium ester (AE) compound linked between two nucleobases of the detection probe oligomer.

Embodiment 58. The method of one any of the preceding Embodiments, wherein the detecting step (3) occurs during the amplifying step (2).

Embodiment 59. The method of Embodiment 56 or 58, wherein the detection probe comprises a fluorescent label and a quencher.

Embodiment 60. The method of Embodiment 59, wherein the detection probe is selected from the group consisting of a molecular torch, a molecular beacon, and a TaqMan detection probe.

Embodiment 61. The method of any one of Embodiments 43 to 60, wherein the detection probe further comprises a non-target-hybridizing sequence.

Embodiment 62. The method of Embodiment 61, wherein the detection probe is a molecular torch or a molecular beacon.

Embodiment 63. The method of Embodiment 43, wherein the at least one detection probe oligomer comprises at least two detection probe oligomers.

Embodiment 64. The method of Embodiment 44, wherein the at least two detection probe oligomers comprise first and second detection probe oligomers, wherein (A) the first detection probe oligomer comprises a target-hybridizing sequence that is (i) contained in the sequence of SEQ ID NO: 197 or its complement, or a DNA equivalent or DNA/RNA chimeric thereof, and (ii) comprises the sequence of SEQ ID NO: 175 or its complement, or a DNA equivalent or DNA/RNA chimeric thereof; and (B) the second detection probe oligomer comprises a target-hybridizing sequence that is (i) contained in the sequence of SEQ ID NO: 197 or its complement, or a DNA equivalent or DNA/RNA chimeric thereof, and (ii) comprises the sequence of SEQ ID NO: 176 or its complement, or a DNA equivalent or DNA/RNA chimeric thereof.

Embodiment 65. The method of Embodiment 64, wherein the first detection probe oligomer comprises the target-hybridizing sequence of SEQ ID NO: 157 or its complement, or a DNA equivalent or DNA/RNA chimeric thereof; and the second detection probe oligomer comprises a target-hybridizing sequence selected from the group consisting of SEQ ID NO: 148 and SEQ ID NO: 152, including complements, DNA equivalents, and DNA/RNA chimerics thereof.

Embodiment 66. The method of any one of the preceding Embodiments, wherein the amplification reaction at step (2) is an isothermal amplification reaction.

Embodiment 67. The method of Embodiment 66, wherein the amplification reaction is a transcription-mediated amplification (TMA) reaction.

Embodiment 68. The method of any one of the preceding Embodiments, wherein the amplification reaction is a real-time amplification reaction.

Embodiment 69. The method of any one of the preceding Embodiments, wherein the sample is a clinical sample.

Embodiment 70. The method of any one of the preceding Embodiments, wherein the sample is a blood sample.

Embodiment 71. The method of any Embodiment 70, wherein the sample is a lysed blood cell sample, optionally wherein the sample is a lysed red blood cell sample.

Embodiment 72. The method of Embodiment 70, wherein the sample is a red blood cell sample.

Embodiment 73. A combination of at least two oligomers for determining the presence or absence of *Plasmodium* species in a sample, said oligomer combination comprising at least two oligomers for amplifying a target region of *Plasmodium* species target nucleic acid, wherein the at least two amplification oligomers comprise:

(a) an amplification oligomer comprising a target-hybridizing sequence (i) that is from about 14 to about 20 contiguous nucleotides in length, is contained in the sequence of SEQ ID NO: 162, and comprises the sequence of SEQ ID NO: 163; or (ii) that is from about 14 to about 25 contiguous nucleotides in length, is contained in the sequence of SEQ ID NO: 166, and comprises the sequence of SEQ ID NO: 167 or SEQ ID NO: 168; and (b) an amplification oligomer comprising a target-hybridizing sequence that is from about 15 to about 33 contiguous nucleotides in length, is contained in SEQ ID NO: 169 and comprises the sequence of SEQ ID NO: 171, SEQ ID NO: 172, or SEQ ID NO: 173.

Embodiment 74. The oligomer combination of Embodiment 73, wherein the at least two amplification oligomers comprise the amplification oligomer of (a)(i).

Embodiment 75. The oligomer combination of Embodiment 74, wherein the target-hybridizing sequence of (a)(i) is selected from the group consisting of SEQ ID NOs: 21, 23-25, 32, 33, 35, 54, and 55.

Embodiment 76. The oligomer combination of Embodiment 74, wherein the target-hybridizing sequence of (a)(i) is contained in the sequence of SEQ ID NO: 164 and comprises the sequence of SEQ ID NO: 165.

Embodiment 77. The oligomer combination of Embodiment 76, wherein the target-hybridizing sequence of (a)(i) is selected from the group consisting of SEQ ID NOs: 21, 23-25, 32, 33, and 35.

Embodiment 78. The oligomer combination of Embodiment 73, wherein the at least two amplification oligomers comprise the amplification oligomer of (a)(ii).

Embodiment 79. The oligomer combination of Embodiment 78, wherein the target-hybridizing sequence of (a)(ii) comprises the sequence of SEQ ID NO: 167.

Embodiment 80. The oligomer combination of Embodiment 79, wherein the target-hybridizing sequence of (a)(ii) is selected from the group consisting of SEQ ID NOs: 28-31, 34, 40, 41, and 49-51.

Embodiment 81. The oligomer combination of Embodiment 78, wherein the target-hybridizing sequence of (a)(ii) comprises the sequence of SEQ ID NO: 168.

Embodiment 82. The oligomer combination of Embodiment 81, wherein the target-hybridizing sequence of (a)(ii) is selected from the group consisting of SEQ ID NOs: 38, 39, 43, 44, and 53.

Embodiment 83. The oligomer combination of any one of Embodiments 73 to 82, wherein the target-hybridizing sequence of (b) is selected from the group consisting of SEQ ID NOs: 80-82 and 85-100.

Embodiment 84. The oligomer combination of any one of Embodiments 73 to 82, wherein the target-hybridizing sequence of (b) is contained in SEQ ID NO: 170 and comprises the sequence of SEQ ID NO: 171 or SEQ ID NO: 172.

Embodiment 85. The oligomer combination of Embodiment 84, wherein the target-hybridizing sequence of (b) comprises the sequence of SEQ ID NO: 171.

Embodiment 86. The oligomer combination of Embodiment 85, wherein the target-hybridizing sequence of (b) is selected from the group consisting of SEQ ID NOs: 81, 82, 85, 87-90, 94, and 96-98.

Embodiment 87. The oligomer combination of Embodiment 84, wherein the target-hybridizing sequence of (b) comprises the sequence of SEQ ID NO: 172.

Embodiment 88. The oligomer combination of Embodiment 87, wherein the target-hybridizing sequence of (b) is selected from the group consisting of SEQ ID NOs: 80, 82, 85, and 87-100.

Embodiment 89. The oligomer combination of any one of the preceding Embodiments, wherein the amplification oligomer of (b) is a promoter primer or promoter provider further comprising a promoter sequence located 5' to the target-hybridizing sequence of (b).

Embodiment 90. The oligomer combination of Embodiment 89, wherein the promoter sequence is a T7 promoter sequence.

Embodiment 91. The oligomer combination of Embodiment 90, wherein the T7 promoter sequence is SEQ ID NO: 179.

Embodiment 92. The oligomer combination of Embodiment 91, wherein the amplification oligomer of (b) comprises a sequence selected from the group consisting of SEQ ID NOs: 57-59 and 62-77.

Embodiment 93. The oligomer combination of Embodiment 73, wherein the target-hybridizing sequences of (a) and (b), respectively, are (A) SEQ ID NO: 30 and SEQ ID NO: 82;

(B) SEQ ID NO: 33 and SEQ ID NO: 82;

(C) SEQ ID NO: 49 and SEQ ID NO: 82;

(D) SEQ ID NO: 21 and SEQ ID NO: 89

(E) SEQ ID NO: 30 and SEQ ID NO: 89;

(F) SEQ ID NO: 33 and SEQ ID NO: 89;

(G) SEQ ID NO: 49 and SEQ ID NO: 89;

(H) SEQ ID NO: 21 and SEQ ID NO: 92;

(I) SEQ ID NO: 30 and SEQ ID NO: 92;

(J) SEQ ID NO: 21 and SEQ ID NO: 94;

(K) SEQ ID NO: 34 and SEQ ID NO: 94;

(L) SEQ ID NO: 53 and SEQ ID NO: 94;

(M) SEQ ID NO: 21 and SEQ ID NO: 95;

(N) SEQ ID NO: 34 and SEQ ID NO: 95; or (O) SEQ ID NO: 53 and SEQ ID NO: 95.

Embodiment 94. The oligomer combination of Embodiment 93, wherein the amplification oligomer of (b) is a promoter primer or promoter provider further comprising a promoter sequence located 5' to the target-hybridizing sequence of (b).

Embodiment 95. The oligomer combination of Embodiment 94, wherein the promoter sequence is a T7 promoter sequence.

Embodiment 96. The oligomer combination of Embodiment 95, wherein the T7 promoter sequence is SEQ ID NO: 179.

Embodiment 97. The oligomer combination of Embodiment 73, wherein the at least two amplification oligomers comprise first and second amplification oligomers as in (a).

Embodiment 98. The oligomer combination of Embodiment 97, wherein the at least two amplification oligomers comprise first and second amplification oligomers as in (a)(ii).

Embodiment 99. The oligomer combination of Embodiment 98, wherein the first amplification oligomer as in (a)(ii) comprises a target-hybridizing sequence comprising the sequence of SEQ ID NO: 167; and the second amplification oligomer as in (a)(ii) comprises a target-hybridizing sequence comprising the sequence of SEQ ID NO: 168.

Embodiment 100. The oligomer combination of Embodiment 99, wherein the first amplification oligomer comprises the target-hybridizing sequence of SEQ ID NO: 34 and the second amplification oligomer comprises the target-hybridizing sequence of SEQ ID NO: 53.

Embodiment 101. The oligomer combination of Embodiment 97, wherein the at least two amplification oligomers comprise an amplification oligomer as in (a)(i) and an amplification oligomer as in (a)(ii).

Embodiment 102. The oligomer combination of Embodiment 101, wherein the amplification oligomer as in (a)(i) comprises a target-hybridizing sequence that is contained in the sequence of SEQ ID NO: 164 and comprises the sequence of SEQ ID NO: 165; and the amplification oligomer as in (a)(ii) comprises the sequence of SEQ ID NO: 167.

Embodiment 103. The oligomer combination of Embodiment 102, wherein the amplification oligomer as in (a)(i) comprises the target-hybridizing sequence of SEQ ID NO: 21 and the amplification oligomer as in (a)(ii) comprises the target-hybridizing sequence of SEQ ID NO: 34.

Embodiment 104. The oligomer combination of any one of Embodiments 73 and 97 to 103, wherein the at least two amplification oligomers comprise first and second amplification oligomers of (b).

Embodiment 105. The oligomer combination of Embodiment 104, wherein each of the first and second amplification oligomers of (b) comprises a target-hybridizing sequence that is contained in SEQ ID NO: 170 and comprises the sequence of SEQ ID NO: 171 or SEQ ID NO: 172.

Embodiment 106. The oligomer combination of Embodiment 105, wherein the first amplification oligomer as in (b) comprises the target-hybridizing sequence of SEQ ID NO: 94 and the second amplification oligomer as in (b) comprises the target-hybridizing sequence of SEQ ID NO: 95.

Embodiment 107. The oligomer combination of Embodiment 93, wherein each of the amplification oligomers of (b) is a promoter primer or promoter provider further comprising a promoter sequence located 5' to the target-hybridizing sequence of (b).

Embodiment 108. The oligomer combination of Embodiment 107, wherein the promoter sequence is a T7 promoter sequence.

Embodiment 109. The oligomer combination of Embodiment 108, wherein the T7 promoter sequence is SEQ ID NO: 179.

Embodiment 110. The oligomer combination of any one of the preceding Embodiments, further comprising at least one capture probe oligomer comprising a target-hybridizing sequence covalently attached to a sequence or moiety that binds to an immobilized probe, wherein said target-hybridizing sequence is up to about 30 contiguous nucleotides in length and comprises a sequence selected from the group consisting of SEQ ID NOs: 11-15, 17, 19, and 20, including DNA equivalents and DNA/RNA chimerics thereof.

Embodiment 111. The oligomer combination of Embodiment 110, wherein the capture probe oligomer target-hybridizing sequence is selected from the group consisting of SEQ ID NOs: 11-15, 17, 19, and 20, including DNA equivalents and DNA/RNA chimerics thereof.

Embodiment 112. The oligomer combination of Embodiment 110, wherein the oligomer combination comprises at least two capture probe oligomers.

Embodiment 113. The oligomer combination of Embodiment 112, wherein the at least two capture probe oligomers comprise a first capture probe oligomer comprising the target-hybridizing sequence of SEQ ID NO: 19, or a DNA equivalent or DNA/RNA chimeric thereof; and a second capture probe oligomer comprising the target-hybridizing sequence of SEQ ID NO: 20, or a DNA equivalent or DNA/RNA chimeric thereof.

Embodiment 114. The oligomer combination of any one of the preceding Embodiments, further comprising at least one detection probe oligomer comprising a target-hybridizing sequence configured to specifically hybridize to a *Plasmodium* species amplicon amplifiable by the at least two amplification oligomers.

Embodiment 115. The oligomer combination of Embodiment 114, wherein the detection probe oligomer target-hybridizing sequence is from about 13 to about 40 nucleotides in length and is (i) contained in the sequence of SEQ ID NO: 196 or its complement, or a DNA equivalent or DNA/RNA chimeric thereof, and (ii) comprises a sequence selected from the group consisting of SEQ ID NO: 175, SEQ ID NO: 176, SEQ ID NO: 177, and SEQ ID NO: 178, including complements, DNA equivalents, and DNA/RNA equivalents thereof.

Embodiment 116. The oligomer combination of Embodiment 115, wherein the detection probe oligomer target-hybridizing sequence is selected from the group consisting of SEQ ID NOs: 131, 132, 135, 140, 145, 147-157, and 159-161, including complements, DNA equivalents, and DNA/RNA equivalents thereof.

Embodiment 117. The oligomer combination of Embodiment 115, wherein the detection probe oligomer target-hybridizing sequence is (i) contained in the sequence of SEQ ID NO: 197 or its complement, or a DNA equivalent or DNA/RNA chimeric thereof, and (ii) comprises a sequence selected from the group consisting of SEQ ID NO: 174 and SEQ ID NO: 175, including complements, DNA equivalents, and DNA/RNA equivalents thereof.

Embodiment 118. The oligomer combination of Embodiment 117, wherein the detection probe oligomer target-hybridizing sequence (ii) comprises the sequence of SEQ ID NO: 174 or its complement, or a DNA equivalent or DNA/RNA chimeric thereof.

Embodiment 119. The oligomer combination of Embodiment 118, wherein the detection probe oligomer target-hybridizing sequence is selected from the group consisting of SEQ ID NOs: 148-155 and 159, including complements, DNA equivalents, and DNA/RNA equivalents thereof.

Embodiment 120. The oligomer combination of Embodiment 117, wherein the detection probe oligomer target-hybridizing sequence (ii) comprises the sequence of SEQ ID NO: 175 or its complement, or a DNA equivalent or DNA/RNA chimeric thereof.

Embodiment 121. The oligomer combination of Embodiment 120, wherein the detection probe oligomer target-hybridizing sequence is selected from the group consisting of SEQ ID NOs: 147, 156, 157, 160, and 161, including complements, DNA equivalents, and DNA/RNA equivalents thereof.

Embodiment 122. The oligomer combination of Embodiment 115, wherein the detection probe oligomer target-hybridizing sequence (ii) comprises a sequence selected from the group consisting of SEQ ID NO: 177 and SEQ ID NO: 178, including complements, DNA equivalents, and DNA/RNA equivalents thereof.

Embodiment 123. The oligomer combination of Embodiment 122, wherein the detection probe oligomer target-hybridizing sequence is selected from the group consisting of SEQ ID NOs: 131, 132, 135, 140, 147, 156, 157, 160, and 161, including complements, DNA equivalents, and DNA/RNA equivalents thereof.

Embodiment 124. The oligomer combination of any one of Embodiments 114 to 123, wherein the detection probe oligomer comprises a 2' methoxy modification on at least one of a nucleotide residue member of the detection probe oligomer nucleotide sequence.

Embodiment 125. The oligomer combination of Embodiment 114 to 124, wherein the amplification oligomer target-hybridizing sequence of (a), the amplification oligomer target-hybridizing sequence of (b), and the detection probe oligomer target-hybridizing sequence, respectively, are (A) SEQ ID NO: 30, SEQ ID NO: 82, and SEQ ID NO: 151 or its complement, or a DNA equivalent or DNA/RNA chimeric of SEQ ID NO: 151 or its complement;

(B) SEQ ID NO: 30, SEQ ID NO: 82, and SEQ ID NO: 157 or its complement, or a DNA equivalent or DNA/RNA chimeric of SEQ ID NO: 157 or its complement;

(C) SEQ ID NO: 33, SEQ ID NO: 82, and SEQ ID NO: 155 or its complement, or a DNA equivalent or DNA/RNA chimeric of SEQ ID NO: 155 or its complement;

(D) SEQ ID NO: 49, SEQ ID NO: 82, and SEQ ID NO: 150 or its complement, or a DNA equivalent or DNA/RNA chimeric of SEQ ID NO: 150 or its complement;

(E) SEQ ID NO: 49, SEQ ID NO: 82, and SEQ ID NO: 155 or its complement, or a DNA equivalent or DNA/RNA chimeric of SEQ ID NO: 155 or its complement;

(F) SEQ ID NO: 21, SEQ ID NO: 89, and SEQ ID NO: 148 or its complement, or a DNA equivalent or DNA/RNA chimeric of SEQ ID NO: 148 or its complement;

(G) SEQ ID NO: 21, SEQ ID NO: 89, and SEQ ID NO: 152 or its complement, or a DNA equivalent or DNA/RNA chimeric of SEQ ID NO: 152 or its complement;

(H) SEQ ID NO: 30, SEQ ID NO: 89; and SEQ ID NO: 148 or its complement, or a DNA equivalent or DNA/RNA chimeric of SEQ ID NO: 148 or its complement;

(I) SEQ ID NO: 30, SEQ ID NO: 89; and SEQ ID NO: 152 or its complement, or a DNA equivalent or DNA/RNA chimeric of SEQ ID NO: 152 or its complement;

(I) SEQ ID NO: 33, SEQ ID NO: 89; and SEQ ID NO: 158 or its complement, or a DNA equivalent or DNA/RNA chimeric of SEQ ID NO: 158 or its complement;

(K) SEQ ID NO: 49, SEQ ID NO: 89, and SEQ ID NO: 150 or its complement, or a DNA equivalent or DNA/RNA chimeric of SEQ ID NO: 150 or its complement;

(L) SEQ ID NO: 21, SEQ ID NO: 92, and SEQ ID NO: 148 or its complement, or a DNA equivalent or DNA/RNA chimeric of SEQ ID NO: 148 or its complement;

(M) SEQ ID NO: 21, SEQ ID NO: 92, and SEQ ID NO: 152 or its complement, or a DNA equivalent or DNA/RNA chimeric of SEQ ID NO: 152 or its complement;

(N) SEQ ID NO: 30, SEQ ID NO: 92; and SEQ ID NO: 148 or its complement, or a DNA equivalent or DNA/RNA chimeric of SEQ ID NO: 148 or its complement;

(O) SEQ ID NO: 30, SEQ ID NO: 92; and SEQ ID NO: 152 or its complement, or a DNA equivalent or DNA/RNA chimeric of SEQ ID NO: 152 or its complement;

(P) SEQ ID NO: 21, SEQ ID NO: 94, and SEQ ID NO: 148 or its complement, or a DNA equivalent or DNA/RNA chimeric of SEQ ID NO: 148 or its complement;

(Q) SEQ ID NO: 21, SEQ ID NO: 94, and SEQ ID NO: 152 or its complement, or a DNA equivalent or DNA/RNA chimeric of SEQ ID NO: 152 or its complement;

(R) SEQ ID NO: 34, SEQ ID NO: 94, and SEQ ID NO: 148 or its complement, or a DNA equivalent or DNA/RNA chimeric of SEQ ID NO: 148 or its complement;

(S) SEQ ID NO: 34, SEQ ID NO: 94, and SEQ ID NO: 152 or its complement, or a DNA equivalent or DNA/RNA chimeric of SEQ ID NO: 152 or its complement;

(T) SEQ ID NO: 34, SEQ ID NO: 94, and SEQ ID NO: 157 or its complement, or a DNA equivalent or DNA/RNA chimeric of SEQ ID NO: 157 or its complement;

(U) SEQ ID NO: 53, SEQ ID NO: 94, and SEQ ID NO: 148 or its complement, or a DNA equivalent or DNA/RNA chimeric of SEQ ID NO: 148 or its complement;

(V) SEQ ID NO: 53, SEQ ID NO: 94, and SEQ ID NO: 152 or its complement, or a DNA equivalent or DNA/RNA chimeric of SEQ ID NO: 152 or its complement;

(W) SEQ ID NO: 53, SEQ ID NO: 94, and SEQ ID NO: 157 or its complement, or a DNA equivalent or DNA/RNA chimeric of SEQ ID NO: 157 or its complement;

(X) SEQ ID NO: 21, SEQ ID NO: 95, and SEQ ID NO: 148 or its complement, or a DNA equivalent or DNA/RNA chimeric of SEQ ID NO: 148 or its complement;

(Y) SEQ ID NO: 21, SEQ ID NO: 95, and SEQ ID NO: 152 or its complement, or a DNA equivalent or DNA/RNA chimeric of SEQ ID NO: 152 or its complement;

(Z) SEQ ID NO: 34, SEQ ID NO: 95, and SEQ ID NO: 148 or its complement, or a DNA equivalent or DNA/RNA chimeric of SEQ ID NO: 148 or its complement;

(AA) SEQ ID NO: 34, SEQ ID NO: 95, and SEQ ID NO: 152 or its complement, or a DNA equivalent or DNA/RNA chimeric of SEQ ID NO: 152 or its complement;

(AB) SEQ ID NO: 34, SEQ ID NO: 95, and SEQ ID NO: 157 or its complement, or a DNA equivalent or DNA/RNA chimeric of SEQ ID NO: 157 or its complement;

(AC) SEQ ID NO: 53, SEQ ID NO: 95, and SEQ ID NO: 148 or its complement, or a DNA equivalent or DNA/RNA chimeric of SEQ ID NO: 148 or its complement;

(AD) SEQ ID NO: 53, SEQ ID NO: 95, and SEQ ID NO: 152 or its complement, or a DNA equivalent or DNA/RNA chimeric of SEQ ID NO: 152 or its complement; or (AE) SEQ ID NO: 53, SEQ ID NO: 95, and SEQ ID NO: 157 or its complement, or a DNA equivalent or DNA/RNA chimeric of SEQ ID NO: 157 or its complement.

Embodiment 126

The oligomer combination of any one of Embodiments 114 to 125, wherein the detection probe oligomer comprises a detectable label.

Embodiment 127. The oligomer combination of Embodiment 126, wherein the detectable label is a chemiluminescent label or a fluorescent label.

Embodiment 128. The oligomer combination of Embodiment 127, wherein the detectable label is a chemiluminescent acridinium ester (AE) compound linked between two nucleobases of the detection probe oligomer.

Embodiment 129. The oligomer combination of Embodiment 127, wherein the detection probe comprises a fluorescent label and a quencher.

Embodiment 130. The oligomer combination of Embodiment 129, wherein the detection probe is selected from the group consisting of a molecular torch, a molecular beacon, and a TaqMan detection probe.

Embodiment 131. The oligomer combination of any one of Embodiments 114 to 130, wherein the detection probe further comprises a non-target-hybridizing sequence.

Embodiment 132. The oligomer combination of Embodiment 131, wherein the detection probe is a molecular torch or a molecular beacon.

Embodiment 133. The oligomer combination of Embodiment 114, wherein the at least two detection probe oligomers comprise first and second detection probe oligomers.

Embodiment 134. The oligomer combination of Embodiment 115, wherein the at least two detection probe oligomers comprise first and second detection probe oligomers, wherein (A) the first detection probe oligomer comprises a target-hybridizing sequence that is (i) contained in the sequence of SEQ ID NO: 197 or its complement, or a DNA equivalent or DNA/RNA chimeric thereof, and (ii) comprises the sequence of SEQ ID NO: 175 or its complement, or a DNA equivalent or DNA/RNA chimeric thereof; and (B) the second detection probe oligomer comprises a target-hybridizing sequence that is (i) contained in the sequence of SEQ ID NO: 197 or its complement, or a DNA equivalent or DNA/RNA chimeric thereof, and (ii) comprises the sequence of SEQ ID NO: 176 or its complement, or a DNA equivalent or DNA/RNA chimeric thereof.

Embodiment 135. The oligomer combination of Embodiment 134, wherein the first detection probe oligomer comprises the target-hybridizing sequence of SEQ ID NO: 157 or its complement, or a DNA equivalent or DNA/RNA chimeric thereof; and the second detection probe oligomer comprises a target-hybridizing sequence selected from the group consisting of SEQ ID NO: 148 and SEQ ID NO: 152, including complements, DNA equivalents, and DNA/RNA equivalents thereof.

Embodiment 136. A detection probe oligomer for specifically detecting a *Plasmodium* species target nucleic acid in a sample, said detection probe oligomer comprising a target-hybridizing sequence that is from about 13 to about 40 nucleotides in length and configured to specifically hybridize to a target sequence contained within a *Plasmodium* species target region amplifiable by an oligomer combination comprising first and second *Plasmodium*-specific amplification oligomers, wherein (a) the first amplification oligomer comprises a target-hybridizing sequence (i) that is from about 14 to about 20 contiguous nucleotides in length, is contained in the sequence of SEQ ID NO: 162, and comprises the sequence of SEQ ID NO: 163, or (ii) that is from about 14 to about 25 contiguous nucleotides in length, is contained in the sequence of SEQ ID NO: 166, and comprises the sequence of SEQ ID NO: 167 or SEQ ID NO: 168; and (b) the second amplification oligomer comprises a target-hybridizing sequence that is from about 15 to about 33 contiguous nucleotides in length, is contained in SEQ ID NO: 169 and comprises the sequence of SEQ ID NO: 171, SEQ ID NO: 172, or SEQ ID NO: 173.

Embodiment 137. The detection probe oligomer of Embodiment 136, wherein the detection probe oligomer target-hybridizing sequence is (i) contained in the sequence of SEQ ID NO: 196 or its complement, or a DNA equivalent or DNA/RNA chimeric thereof, and (ii) comprises a sequence selected from the group consisting of SEQ ID NO: 175, SEQ ID NO: 176, SEQ ID NO: 177, and SEQ ID NO: 178, including complements, DNA equivalents, and DNA/RNA equivalents thereof.

Embodiment 138. The detection probe oligomer of Embodiment 137, wherein the detection probe oligomer target-hybridizing sequence is selected from the group consisting of SEQ ID NOs: 131, 132, 135, 140, 145, 147-157, and 159-161, including complements, DNA equivalents, and DNA/RNA chimerics thereof.

Embodiment 139. The detection probe oligomer of Embodiment 137, wherein the detection probe oligomer target-hybridizing sequence is (i) contained in the sequence of SEQ ID NO: 197 or its complement, or a DNA equivalent or DNA/RNA chimeric thereof, and (ii) comprises the sequence of SEQ ID NO: 174 or SEQ ID NO: 175, including complements, DNA equivalents, and DNA/RNA chimerics thereof.

Embodiment 140. The detection probe oligomer of Embodiment 139, wherein the detection probe oligomer target-hybridizing sequence (ii) comprises the sequence of SEQ ID NO: 174 or its complement, or a DNA equivalent or DNA/RNA chimeric thereof.

Embodiment 141. The detection probe oligomer of Embodiment 140, wherein the detection probe oligomer target-hybridizing sequence is selected from the group consisting of SEQ ID NOs: 148-155 and 159, including complements, DNA equivalents, and DNA/RNA chimerics thereof.

Embodiment 142. The detection probe oligomer of Embodiment 139, wherein the detection probe oligomer target-hybridizing sequence (ii) comprises the sequence of SEQ ID NO: 175 or its complement, or a DNA equivalent or DNA/RNA chimeric thereof.

Embodiment 143. The detection probe oligomer of Embodiment 142, wherein the detection probe oligomer target-hybridizing sequence is selected from the group consisting of SEQ ID NOs: 147, 156, 157, 160, and 161, including complements, DNA equivalents, and DNA/RNA chimerics thereof.

Embodiment 144. The detection probe oligomer of Embodiment 137, wherein the detection probe oligomer target-hybridizing sequence (ii) comprises a sequence selected from the group consisting of SEQ ID NO: 177 and SEQ ID NO: 178, including complements, DNA equivalents, and DNA/RNA chimerics thereof.

Embodiment 145. The detection probe oligomer of Embodiment 144, wherein the detection probe oligomer target-hybridizing sequence is selected from the group consisting of SEQ ID NOs: 131, 132, 135, 140, 147, 156, 157, 160, and 161, including complements, DNA equivalents, and DNA/RNA chimerics thereof.

Embodiment 146. The detection probe oligomer of any one of Embodiments 136 to 145, wherein the detection probe oligomer comprises a 2' methoxy modification on at least one of a nucleotide residue member of the detection probe oligomer nucleotide sequence.

Embodiment 147. The detection probe oligomer of any one of Embodiments 136 to 146, wherein the detection probe oligomer comprises a label.

Embodiment 148. The detection probe oligomer of Embodiment 147, wherein the label is a chemiluminescent label or a fluorescent label.

Embodiment 149. The detection probe oligomer of Embodiment 148, wherein the label is a chemiluminescent acridinium ester (AE) compound linked between two nucleobases of the detection probe oligomer.

Embodiment 150. The detection probe oligomer of Embodiment 148, wherein the detection probe comprises a fluorescent label and a quencher.

Embodiment 152. The detection probe oligomer of Embodiment 150, wherein the detection probe is selected from the group consisting of a molecular torch, a molecular beacon, and a TaqMan detection probe.

Embodiment 153. The detection probe oligomer of any one of Embodiments 136 to 152, wherein the detection probe further comprises a non-target-hybridizing sequence.

Embodiment 154. The detection probe oligomer of Embodiment 153, wherein the detection probe is a molecular torch or a molecular beacon.

Embodiment 155. A combination of at least two oligomers for detecting a *Plasmodium* species target nucleic acid in a sample, said oligomer combination comprising at least two detection probe oligomers of Embodiment 136.

Embodiment 156. The oligomer combination of Embodiment 155, wherein the at least two detection probe oligomers comprise first and second detection probe oligomers, wherein (A) the first detection probe oligomer comprises a target-hybridizing sequence that (i) is contained in the sequence of SEQ ID NO: 197 or its complement, or a DNA equivalent or DNA/RNA chimeric thereof, and (ii) comprises the sequence of SEQ ID NO: 175 or its complement, or a DNA equivalent or DNA/RNA chimeric thereof; and (B) the second detection probe oligomer comprises a target-hybridizing sequence that (i) is contained in the sequence of SEQ ID NO: 197 or its complement, or a DNA equivalent or DNA/RNA chimeric thereof, and (ii) comprises the sequence of SEQ ID NO: 176 or its complement, or a DNA equivalent or DNA/RNA chimeric thereof.

Embodiment 157. The oligomer combination of Embodiment 156, wherein the first detection probe oligomer comprises the target-hybridizing sequence of SEQ ID NO: 157 or its complement, or a DNA equivalent or DNA/RNA chimeric thereof; and the second detection probe oligomer comprises a target-hybridizing sequence selected from the group consisting of SEQ ID NO: 148 and SEQ ID NO: 152, including complements, DNA equivalents, and DNA/RNA chimerics thereof.

Embodiment 158. A capture probe oligomer for specifically isolating *Plasmodium* species nucleic acid from a sample, said capture probe oligomer comprising a target-hybridizing sequence covalently attached to a sequence or moiety that binds to an immobilized probe, wherein said target-hybridizing sequence is up to about 30 contiguous nucleotides in length and comprises a sequence selected from the group consisting of SEQ ID NOs: 11-15, 17, 19, and 20, including DNA equivalents and DNA/RNA chimerics thereof.

Embodiment 159. The capture probe oligomer of Embodiment 158, wherein the capture probe oligomer target-hybridizing sequence is selected from the group consisting of SEQ ID NOs: 11-15, 17, 19, and 20, including DNA equivalents and DNA/RNA chimerics thereof.

Embodiment 160. A combination of at least two oligomers for specifically isolating *Plasmodium* species nucleic acid from a sample, wherein the oligomer combination comprises at least two capture probe oligomers of Embodiment 158.

Embodiment 161. The oligomer combination of Embodiment 160, wherein the at least two capture probe oligomers comprise a first capture probe oligomer comprising the target-hybridizing sequence of SEQ ID NO: 19, or a DNA equivalent or DNA/RNA chimeric thereof; and a second capture probe oligomer comprising the target-hybridizing sequence of SEQ ID NO: 20, or a DNA equivalent or DNA/RNA chimeric thereof.

Embodiment 162. A kit comprising the combination of at least two oligomers according to any one of Embodiments 73 to 135, 155 to 157, 160, and 161.

Embodiment 163. A reaction mixture comprising the combination of at least two oligomers according to any one of Embodiments 73 to 135, 155 to 157, 160, and 161.

Embodiment 164. Use of the combination of at least two oligomers according to any one of Embodiments 73 to 135 for specifically amplifying *Plasmodium* species nucleic acid in a sample.

Embodiment 165. Use of the detection probe oligomer or oligomer combination according to any one of Embodiments 136 to 157 for specifically detecting *Plasmodium* species nucleic acid in a sample.

Embodiment 166. Use of the capture probe oligomer or oligomer combination according to any one of Embodiments 158 to 161 for specifically capturing *Plasmodium* species nucleic acid from a sample.

Embodiment 167. A method for specifically detecting *Plasmodium* species nucleic acid in a sample, said method comprising:

(1) contacting a sample, said sample suspected of containing *Plasmodium* species nucleic acid, with at least two oligomers for amplifying a target region of a *Plasmodium* species target nucleic acid, wherein the at least two amplification oligomers comprise:

(a) an amplification oligomer comprising a target-hybridizing sequence that is contained in the sequence of SEQ ID NO: 185 and comprises the sequence of SEQ ID NO: 37, SEQ ID NO: 46, or SEQ ID NO: 187; and (b) an amplification oligomer comprising a target-hybridizing sequence that is contained in SEQ ID NO: 188 and comprises the sequence of SEQ ID NO: 83, SEQ ID NO: 84, or SEQ ID NO: 182;

(2) performing an in vitro nucleic acid amplification reaction, wherein any *Plasmodium* target nucleic acid present in said sample is used as a template for generating an amplification product; and (3) detecting the presence or absence of the amplification product, thereby indicating the presence or absence of *Plasmodium* species target nucleic acid in said sample.

Embodiment 168. The method of Embodiment 167, wherein the target-hybridizing sequence of (a) is selected from the group consisting of SEQ ID NOs: 37, 46, 183, and 184.

Embodiment 169. The method of Embodiment 168, wherein the target-hybridizing sequence of (a) is contained in the sequence of SEQ ID NO: 186.

Embodiment 170. The method of Embodiment 169, wherein the target-hybridizing sequence of (a) is SEQ ID NO: 183 or SEQ ID NO: 184.

Embodiment 171. The method of any one of Embodiments 167 to 170, wherein the target-hybridizing sequence of (b) is selected from the group consisting of SEQ ID NOs: 83, 84, and 182.

Embodiment 172. The method of Embodiment 167, wherein the target-hybridizing sequences of (a) is SEQ ID NO: 183 or SEQ ID NO: 184 and the target-hybridizing sequence of (b) is SEQ ID NO: 182.

Embodiment 173. The method of any one of Embodiments 167 to 172, wherein the detecting step (3) comprises contacting the in vitro nucleic acid amplification reaction with at least one detection probe oligomer comprising a target-hybridizing sequence configured to specifically hybridize to the amplification product under conditions whereby the presence or absence of the amplification product is determined, thereby indicating the presence or absence of *Plasmodium* species in said sample.

Embodiment 174. The method of Embodiment 173, wherein the detection probe oligomer target-hybridizing sequence is at least about 13 nucleotides in length and is (i) contained in the sequence of SEQ ID NO: 189 or its complement, or a DNA equivalent or DNA/RNA chimeric thereof, and (ii) comprises a sequence selected from the group consisting of SEQ ID NO: 190 and SEQ ID NO: 191, including complements, DNA equivalents, and DNA/RNA equivalents thereof.

Embodiment 175. The method of Embodiment 174, wherein the detection probe oligomer target-hybridizing sequence is selected from the group consisting of SEQ ID NOs: 125-130 and 143, including complements, DNA equivalents, and DNA/RNA chimerics thereof.

Embodiment 176. The method of Embodiment 173, wherein the amplification oligomer target-hybridizing sequence of (a), the amplification oligomer target-hybridizing sequence of (b), and the detection probe oligomer target-hybridizing sequence, respectively, are (A) SEQ ID NO: 183, SEQ ID NO: 182, and SEQ ID NO: 126 or its complement, or a DNA equivalent or DNA/RNA chimeric of SEQ ID NO: 126 or its complement;

(B) SEQ ID NO: 183, SEQ ID NO: 182, and SEQ ID NO: 127 or its complement, or a DNA equivalent or DNA/RNA chimeric of SEQ ID NO: 127 or its complement;

(C) SEQ ID NO: 183, SEQ ID NO: 182, and SEQ ID NO: 128 or its complement, or a DNA equivalent or DNA/RNA chimeric of SEQ ID NO: 128 or its complement;

(D) SEQ ID NO: 183, SEQ ID NO: 182, and SEQ ID NO: 143 or its complement, or a DNA equivalent or DNA/RNA chimeric of SEQ ID NO: 143 or its complement;

(E) SEQ ID NO: 183, SEQ ID NO: 182, and SEQ ID NO: 129 or its complement, or a DNA equivalent or DNA/RNA chimeric of SEQ ID NO: 129 or its complement; or (F) SEQ ID NO: 184, SEQ ID NO: 182, and SEQ ID NO: 126 or its complement, or a DNA equivalent or DNA/RNA chimeric of SEQ ID NO: 126 or its complement.

Embodiment 177. A combination of at least two oligomers for determining the presence or absence of *Plasmodium* species in a sample, said oligomer combination comprising at least two oligomers for amplifying a target region of *Plasmodium* species target nucleic acid, wherein the at least two amplification oligomers comprise:

(a) an amplification oligomer comprising a target-hybridizing sequence that is contained in the sequence of SEQ ID NO: 185 and comprises the sequence of SEQ ID NO: 37, SEQ ID NO: 46, or SEQ ID NO: 187; and (b) an amplification oligomer comprising a target-hybridizing sequence that is contained in SEQ ID NO: 188 and comprises the sequence of SEQ ID NO: 83, SEQ ID NO: 84, or SEQ ID NO: 182.

Embodiment 178. The oligomer combination of Embodiment 177, wherein the target-hybridizing sequence of (a) is selected from the group consisting of SEQ ID NOs: 37, 46, 183, and 184.

Embodiment 179. The oligomer combination of Embodiment 178, wherein the target-hybridizing sequence of (a) is contained in the sequence of SEQ ID NO: 186.

Embodiment 180. The oligomer combination of Embodiment 179, wherein the target-hybridizing sequence of (a) is SEQ ID NO: 183 or SEQ ID NO: 184.

Embodiment 181. The oligomer combination of any one of Embodiments 177 to 180, wherein the target-hybridizing sequence of (b) is selected from the group consisting of SEQ ID NOs: 83, 84, and 182.

Embodiment 182. The oligomer combination of Embodiment 177, wherein the target-hybridizing sequences of (a) is SEQ ID NO: 183 or SEQ ID NO: 184 and the target-hybridizing sequence of (b) is SEQ ID NO: 182.

Embodiment 183. The oligomer combination of any one of Embodiments 177 to 182, further comprising at least one detection probe oligomer comprising a target-hybridizing sequence configured to specifically hybridize to a *Plasmodium* species amplicon amplifiable by the at least two amplification oligomers.

Embodiment 184. The oligomer combination of Embodiment 183, wherein the detection probe oligomer target-hybridizing sequence is at least about 13 nucleotides in length and is (i) contained in the sequence of SEQ ID NO: 189 or its complement, or a DNA equivalent or DNA/RNA chimeric thereof, and (ii) comprises a sequence selected from the group consisting of SEQ ID NO: 190 and SEQ ID NO: 191, including complements, DNA equivalents, and DNA/RNA equivalents thereof.

Embodiment 185. The oligomer combination of Embodiment 174, wherein the detection probe oligomer target-hybridizing sequence is selected from the group consisting of SEQ ID NOs: 125-130 and 143, including complements, DNA equivalents, and DNA/RNA chimerics thereof.

Embodiment 186. The oligomer combination of Embodiment 173, wherein the amplification oligomer target-hybridizing sequence of (a), the amplification oligomer target-hybridizing sequence of (b), and the detection probe oligomer target-hybridizing sequence, respectively, are (A) SEQ ID NO: 183, SEQ ID NO: 182, and SEQ ID NO: 126 or its complement, or a DNA equivalent or DNA/RNA chimeric of SEQ ID NO: 126 or its complement;

(B) SEQ ID NO: 183, SEQ ID NO: 182, and SEQ ID NO: 127 or its complement, or a DNA equivalent or DNA/RNA chimeric of SEQ ID NO: 127 or its complement;

(C) SEQ ID NO: 183, SEQ ID NO: 182, and SEQ ID NO: 128 or its complement, or a DNA equivalent or DNA/RNA chimeric of SEQ ID NO: 128 or its complement;

(D) SEQ ID NO: 183, SEQ ID NO: 182, and SEQ ID NO: 143 or its complement, or a DNA equivalent or DNA/RNA chimeric of SEQ ID NO: 143 or its complement;

(E) SEQ ID NO: 183, SEQ ID NO: 182, and SEQ ID NO: 129 or its complement, or a DNA equivalent or DNA/RNA chimeric of SEQ ID NO: 129 or its complement; or (F) SEQ ID NO: 184, SEQ ID NO: 182, and SEQ ID NO: 126 or its complement, or a DNA equivalent or DNA/RNA chimeric of SEQ ID NO: 126 or its complement.

Embodiment 187. A detection probe oligomer for specifically detecting a *Plasmodium* species target nucleic acid in a sample, said detection probe oligomer comprising a target-hybridizing sequence that is at least about 13 nucleotides in length and configured to specifically hybridize to a target sequence contained within a *Plasmodium* species target region amplifiable by an oligomer combination comprising first and second *Plasmodium*-specific amplification oligomers, wherein (a) the first amplification oligomer comprises a target-hybridizing sequence that is contained in the sequence of SEQ ID NO: 185 and comprises the sequence of SEQ ID NO: 37, SEQ ID NO: 46, or SEQ ID NO: 187; and (b) the second amplification oligomer comprises a target-hybridizing sequence that is contained in SEQ ID NO: 188 and comprises the sequence of SEQ ID NO: 83, SEQ ID NO: 84, or SEQ ID NO: 182.

Embodiment 188. A kit comprising the combination of at least two oligomers according to any one of Embodiments 177 to 186.

Embodiment 189. A reaction mixture comprising the combination of at least two oligomers according to any one of Embodiments 177 to 186.

Embodiment 190. Use of the combination of at least two oligomers according to any one of Embodiments 177 to 186 for specifically amplifying *Plasmodium* species nucleic acid in a sample.

Embodiment 191. Use of the detection probe oligomer or oligomer combination according to any one of Embodiments 177 to 187 for specifically detecting *Plasmodium* species nucleic acid in a sample.

From the foregoing, it will be appreciated that, although specific embodiments of the invention have been described herein for purposes of illustration, various modifications may be made without deviating from the spirit and scope of the invention. Accordingly, the invention is not limited except as by the appended claims. All publications, patents, and patent applications cited herein are hereby incorporated by reference in their entireties for all purposes.

The invention claimed is:

1. A method for specifically detecting *Plasmodium* species nucleic acid in a sample, said method comprising:
   (1) contacting a sample, said sample suspected of containing *Plasmodium* species nucleic acid, with at least two oligomers for amplifying a target region of a *Plasmodium* species target nucleic acid, wherein the at least two amplification oligomers comprise:
      (a) at least one first amplification oligomer comprising a target-hybridizing sequence
         (i) that is from about 14 to about 20 contiguous nucleotides in length, is contained in the sequence of SEQ ID NO: 162, and comprises the sequence of SEQ ID NO: 163; or
         (ii) that is from about 14 to about 25 contiguous nucleotides in length, is contained in the sequence of SEQ ID NO: 166, and comprises the sequence of SEQ ID NO: 167 or SEQ ID NO: 168; and
      (b) at least one second amplification oligomer comprising a target-hybridizing sequence that is from about 15 to about 33 contiguous nucleotides in length, is contained in SEQ ID NO: 169 and comprises the sequence of SEQ ID NO: 171, SEQ ID NO:172, or SEQ ID NO:173;
   (2) performing an in vitro nucleic acid amplification reaction, wherein any *Plasmodium* target nucleic acid present in said sample is used as a template for generating an amplification product; and
   (3) contacting the in vitro nucleic acid amplification with at least one detection probe oligomer configured to specifically hybridize to the amplification product, wherein the at least one detection probe oligomer comprises a detectable label; and
   (4) detecting the presence or absence of the amplification product, thereby indicating the presence or absence of *Plasmodium* species target nucleic acid in said sample.

2. The method of claim 1, wherein the target-hybridizing sequence of the at least one first amplification oligomer
   (A) comprises a sequence selected from the group consisting of SEQ ID NOs: 21, 23-25, 32, 33, 35, 54, and 55;
   (B) is contained in the sequence of SEQ ID NO: 164 and comprises the sequence of SEQ ID NO: 165;
   (C) comprises the sequence of SEQ ID NO:167;
   (D) comprises a sequence selected from the group consisting of SEQ ID NOs: 28-31, 34, 40, 41, and 49-51;
   (E) comprises the sequence of SEQ ID NO:168; or
   (F) comprises the sequence selected from the group consisting of SEQ ID NOs: 38, 39, 43, 44, and 53.

3. The method claim 1, wherein the target-hybridizing sequence of the at least one second amplification oligomer
   (A) comprises a sequence selected from the group consisting of SEQ ID NOs: 80-82 and 85-100; or
   (B) is contained in SEQ ID NO:170, and comprises the sequence of SEQ ID NO: 171 or SEQ ID NO: 172.

4. The method of claim 1, wherein the second amplification oligomer is
   (A) a promoter primer;
   (B) a promoter provider further comprising a promoter sequence located 5' to the target-hybridizing sequence;
   (C) a promoter provider further comprising a promoter sequence located 5' to the target-hybridizing sequence wherein the promoter sequence is a T7 promoter sequence; or
   (D) comprises a sequence selected from the group consisting of SEQ ID NOs: 57-59 and 62-77.

5. The method of claim 1, wherein the target-hybridizing sequences of the first and second amplification oligomers, respectively, are
   (A) SEQ ID NO:30 and SEQ ID NO:82;
   (B) SEQ ID NO:33 and SEQ ID NO:82;
   (C) SEQ ID NO: 49 and SEQ ID NO: 82;
   (D) SEQ ID NO:21 and SEQ ID NO:89;
   (E) SEQ ID NO:30 and SEQ ID NO:89;
   (F) SEQ ID NO:33 and SEQ ID NO:89;
   (G) SEQ ID NO:49 and SEQ ID NO:89;
   (H) SEQ ID NO:21 and SEQ ID NO:92;
   (I) SEQ ID NO:30 and SEQ ID NO:92;
   (J) SEQ ID NO:21 and SEQ ID NO:94;
   (K) SEQ ID NO: 34 and SEQ ID NO: 94;
   (L) SEQ ID NO:53 and SEQ ID NO:94;
   (M) SEQ ID NO: 21 and SEQ ID NO: 95;
   (N) SEQ ID NO:34 and SEQ ID NO:95; or
   (O) SEQ ID NO:53 and SEQ ID NO:95.

6. The method of claim 1, wherein the at least one first amplification oligomer comprises at least two first amplification oligomers, wherein the at least two amplification oligomers are selected from the group consisting of:
   (A) an amplification oligomer comprising a target-hybridizing sequence comprising the sequence of SEQ ID NO:167, or an amplification oligomer comprising a target-hybridizing sequence comprising the sequence of SEQ ID NO:34; and
   (B) an amplification oligomer comprising a target-hybridizing sequence comprising the sequence of SEQ ID NO:168, an amplification oligomer comprising a target-hybridizing sequence comprising the sequence of SEQ ID NO:53, an amplification oligomer comprising a target-hybridizing sequence that is contained in the sequence of SEQ ID NO:164 and comprises the sequence of SEQ ID NO: 165, or an amplification oligomer comprising a target-hybridizing sequence consisting of SEQ ID NO:21.

7. The method of claim 1, wherein the at least one second amplification oligomer comprises at least two second amplification oligomers wherein the at least two second amplification oligomers are selected from the group consisting of: an amplification oligomer comprising a target-hybridizing sequence comprising the sequence of SEQ ID NO:94 and an amplification oligomer comprising a target-hybridizing sequence comprising the sequence of SEQ ID NO:95.

8. The method of claim 1, further comprising purifying the target nucleic acid from other components in the sample before step (1), wherein the purifying step comprises contacting the sample with at least one capture probe oligomer comprising a target-hybridizing sequence covalently attached to a sequence or moiety that binds to an immobilized probe, wherein said target-hybridizing sequence is up to about 30 contiguous nucleotides in length and comprises a sequence selected from the group consisting of SEQ ID NOs: 11-15, 17, 19, and 20, including DNA equivalents and DNA/RNA chimerics thereof.

9. The method of claim 1, wherein the at least one detection probe oligomer comprises a target-hybridizing sequence, wherein the detection probe oligomer target-hybridizing sequence (A) is about 13 to about 40 nucleotides in length, is contained in the sequence of SEQ ID NO:196 or its complement, or a DNA equivalent or DNA/RNA chimeric thereof, and comprises a sequence selected from the group consisting of SEQ ID NO:175, SEQ ID NO:176, SEQ ID NO:177, and SEQ ID NO:178, including complements, DNA equivalents, and DNA/RNA equivalents thereof; or (B) comprises a sequence selected from the group consisting of SEQ ID NOs: 131, 132, 135, 140, 145, 147-157, and 159-161, including complements, DNA equivalents, and DNA/RNA chimerics thereof;

whereby the presence or absence of the amplification product is determined, thereby indicating the presence or absence of *Plasmodium* species in said sample.

10. The method of claim 9, wherein the detection probe oligomer target-hybridizing sequence (A) is contained in the sequence of SEQ ID NO: 197 or its complement, or a DNA equivalent or DNA/RNA chimeric thereof, and comprises the sequence of SEQ ID NO:174 or SEQ ID NO:175, including complements, DNA equivalents, and DNA/RNA chimerics thereof;

(B) comprises a sequence selected from the group consisting of SEQ ID NOs: 131, 132, 135, 140, 147-157, 160, and 161, including complements, DNA equivalents, and DNA/RNA chimerics thereof, or (C) comprises a sequence selected from the group consisting of SEQ ID NO:177 and SEQ ID NO:178, including complements, DNA equivalents, and DNA/RNA chimerics thereof.

11. The method of claim 9, wherein the at least one detection probe oligomer comprises a first detection probe oligomer and a second detection probe oligomer, wherein (A) the first detection probe oligomer comprises a target-hybridizing sequence that is contained in the sequence of SEQ ID NO: 197 or its complement, or a DNA equivalent or DNA/RNA chimeric thereof and comprises the sequence of SEQ ID NO:175 or its complement, or a DNA equivalent or DNA/RNA chimeric thereof; or comprises the target-hybridizing sequence of SEQ ID NO: 157 or its complement, or a DNA equivalent or DNA/RNA chimeric thereof; and (B) the second detection probe oligomer comprises a target-hybridizing sequence that is contained in the sequence of SEQ ID NO: 197 or its complement, or a DNA equivalent or DNA/RNA chimeric thereof and comprises the sequence of SEQ ID NO: 176 or its complement, or a DNA equivalent or DNA/RNA chimeric thereof, or comprises a target-hybridizing sequence comprising a sequence selected from the group consisting of SEQ ID NO: 148 and SEQ ID NO: 152, including complements, DNA equivalents, and DNA/RNA chimerics thereof.

12. The method of claim 1, wherein the amplification reaction at step (2) is an isothermal amplification reaction; wherein the isothermal amplification reaction can be a transcription-mediated amplification (TMA) reaction; and wherein the isothermal amplification reaction or the TMA can be is a real-time amplification reaction.

13. A combination of oligomers for determining the presence or absence of *Plasmodium* species in a sample, said oligomer combination comprising:

(1) at least two amplification oligomers for amplifying a target region of *Plasmodium* species target nucleic acid, wherein the at least two amplification oligomers comprise:

(a) at least one first amplification oligomer comprising a target-hybridizing sequence (i) that is from about 14 to about 20 contiguous nucleotides in length, is contained in the sequence of SEQ ID NO:162, and comprises the sequence of SEQ ID NO:163; or (ii) that is from about 14 to about 25 contiguous nucleotides in length, is contained in the sequence of SEQ ID NO:166, and comprises the sequence of SEQ ID NO: 167 or SEQ ID NO:168; and (b) at least one second amplification oligomer comprising a target-hybridizing sequence that is from about 15 to about 33 contiguous nucleotides in length, is contained in SEQ ID NO: 169 and comprises the sequence of SEQ ID NO: 171, SEQ ID NO: 172, or SEQ ID NO: 173; and (2) at least one detection probe oligomer configured to specifically hybridize to an amplification product of the at least two amplification oligomers, wherein the at least one detection probe oligomer comprises a fluorescent label, a chemiluminescent label, or a fluorescent label and a non-fluorescent quencher.

14. The combination of claim 13, wherein the target-hybridizing sequence of the at least one first amplification oligomer:

(A) comprises a sequence selected from the group consisting of SEQ ID NOs: 21, 23-25, 32, 33, 35, 54, and 55;

(B) is contained in the sequence of SEQ ID NO:164, and comprises the sequence of SEQ ID NO:165;

(C) comprises the sequence of SEQ ID NO:167

(D) comprises a sequence selected from the group consisting of SEQ ID NOs: 28-31, 34, 40, 41, and 49-51;

(E) comprises the sequence of SEQ ID NO:168; or (F) comprises a sequence selected from the group consisting of SEQ ID NOs: 38, 39, 43, 44, and 53.

15. The combination of claim 13, wherein the target-hybridizing sequence of the at least one second amplification oligomer (A) comprises a sequence selected from the group consisting of SEQ ID NOs: 80-82 and 85-100; or (B) is contained in SEQ ID NO: 170, comprises the sequence of SEQ ID NO:171 or SEQ ID NO:172.

16. The combination of claim 13, wherein the second amplification oligomer is (A) a promoter primer;

(B) a promoter provider further comprising a promoter sequence located 5' to the target-hybridizing sequence;

(C) a promoter provider further comprising a promoter sequence located 5' to the target-hybridizing sequence wherein the promoter sequence is a T7 promoter sequence; or (D) comprises a sequence selected from the group consisting of SEQ ID NOs: 57-59 and 62-77.

17. The combination of claim 13, wherein the target-hybridizing sequences of the first and second amplification oligomers, respectively, are (A) SEQ ID NO:30 and SEQ ID NO:82;

(B) SEQ ID NO:33 and SEQ ID NO:82;

(C) SEQ ID NO:49 and SEQ ID NO:82;

(D) SEQ ID NO:21 and SEQ ID NO:89

(E) SEQ ID NO:30 and SEQ ID NO:89;

(F) SEQ ID NO:33 and SEQ ID NO:89;

(G) SEQ ID NO:49 and SEQ ID NO:89;

(H) SEQ ID NO:21 and SEQ ID NO:92;

(I) SEQ ID NO:30 and SEQ ID NO:92;

(J) SEQ ID NO:21 and SEQ ID NO:94;

(K) SEQ ID NO:34 and SEQ ID NO:94;

(L) SEQ ID NO:53 and SEQ ID NO:94;

(M) SEQ ID NO:21 and SEQ ID NO:95;

(N) SEQ ID NO:34 and SEQ ID NO:95; or (O) SEQ ID NO:53 and SEQ ID NO:95.

18. The combination of claim 13, wherein the at least one first amplification oligomer comprises at least two first amplification oligomers, wherein the at least two amplification oligomers are selected from the group consisting of:

(A) an amplification oligomer comprising a target-hybridizing sequence comprising the sequence of SEQ ID NO:167, or an amplification oligomer comprising a target-hybridizing sequence comprising the sequence of SEQ ID NO:34; and (B) an amplification oligomer comprising a target-hybridizing sequence comprising the sequence of SEQ ID NO:168, an amplification oligomer comprising a target-hybridizing sequence comprising the sequence of SEQ ID NO:53, an amplification oligomer comprising a target-hybridizing sequence that is contained in the sequence of SEQ ID NO:164 and comprises the sequence of SEQ ID NO:165, or an amplification oligomer comprising a target-hybridizing sequence comprising the sequence of SEQ ID NO:21.

19. The combination of claim 13, wherein the at least one second amplification oligomer comprises at least two second amplification oligomers wherein the at least two second amplification oligomers are selected from the group consisting of: an amplification oligomer comprising a target-hybridizing sequence comprising the sequence of SEQ ID NO:94 and an amplification oligomer comprising a target-hybridizing sequence comprising the sequence of SEQ ID NO:95.

20. The combination of claim 13, further comprising at least one capture probe oligomer wherein the capture probe oligomer comprises a target-hybridizing sequence covalently attached to a sequence or moiety that binds to an immobilized probe, wherein said target-hybridizing sequence is up to about 30 contiguous nucleotides in length and comprises a sequence selected from the group consisting of SEQ ID NOs: 11-15, 17, 19, and 20, including DNA equivalents and DNA/RNA chimerics thereof.

21. The combination of claim 13, wherein the at least one detection probe oligomer comprises a target-hybridizing sequence, wherein the detection probe oligomer target-hybridizing sequence (A) is about 13 to about 40 nucleotides in length, is contained in the sequence of SEQ ID NO:196 or its complement, or a DNA equivalent or DNA/RNA chimeric thereof, and comprises a sequence selected from the group consisting of SEQ ID NO:175, SEQ ID NO:176, SEQ ID NO:177, and SEQ ID NO:178, including complements, DNA equivalents, and DNA/RNA equivalents thereof, or (B) comprises a sequence selected from the group consisting of SEQ ID NOs: 131, 132, 135, 140, 145, 147-157, and 159-161, including complements, DNA equivalents, and DNA/RNA chimerics thereof.

22. The combination of claim 21, wherein the detection probe oligomer target-hybridizing sequence (A) is contained in the sequence of SEQ ID NO: 197 or its complement, or a DNA equivalent or DNA/RNA chimeric thereof, and comprises a sequence selected from the group consisting of SEQ ID NO: 174 and SEQ ID NO:175, including complements, DNA equivalents, and DNA/RNA equivalents thereof;

(B) comprises a sequence selected from the group consisting of SEQ ID NOs: 131, 132, 135, 140, 147-157, 160, and 161, including complements, DNA equivalents, and DNA/RNA equivalents thereof; or (C) comprises a sequence selected from the group consisting of SEQ ID NO:177 and SEQ ID NO:178, including complements, DNA equivalents, and DNA/RNA chimerics thereof.

23. The combination of claim 21, wherein the at least one detection probe oligomer comprises a first detection probe oligomer and a second detection probe oligomer, wherein (A) the first detection probe oligomer comprises a target-hybridizing sequence that is contained in the sequence of SEQ ID NO: 197 or its complement, or a DNA equivalent or DNA/RNA chimeric thereof and comprises the sequence of SEQ ID NO: 175 or its complement, or a DNA equivalent or DNA/RNA chimeric thereof; or comprises the target-hybridizing sequence of SEQ ID NO:157 or its complement, or a DNA equivalent or DNA/RNA chimeric thereof, and (B) the second detection probe oligomer comprises a target-hybridizing sequence that is contained in the sequence of SEQ ID NO: 197 or its complement, or a DNA equivalent or DNA/RNA chimeric thereof and comprises the sequence of SEQ ID NO: 176 or its complement, or a DNA equivalent or DNA/RNA chimeric thereof, or comprises a target-hybridizing sequence comprising a sequence selected from the group consisting of SEQ ID NO: 148 and SEQ ID NO: 152, including complements, DNA equivalents, and DNA/RNA equivalents thereof.

24. The combination of claim 13, wherein the at least two oligomers are provided in a kit or a reaction mixture.

* * * * *

SEQUENCE LISTING

```
<160> NUMBER OF SEQ ID NOS: 197

<210> SEQ ID NO 1
<211> LENGTH: 55
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (23)..(55)

<400> SEQUENCE: 1
ggauugggua auuugcgcgc cctttaaaaa aaaaaaaaaa aaaaaaaaaa aaaaa          55

<210> SEQ ID NO 2
<211> LENGTH: 61
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
```

```
<222> LOCATION: (29)..(61)

<400> SEQUENCE: 2
caagaaagag cuaucaaucu gucaauccut taaaaaaaaa aaaaaaaaaa aaaaaaaaaa        60
a                                                                       61

<210> SEQ ID NO 3
<211> LENGTH: 59
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (27)..(59)

<400> SEQUENCE: 3
cccguguuga gucaaauuaa gccgcattta aaaaaaaaaa aaaaaaaaaa aaaaaaaa        59

<210> SEQ ID NO 4
<211> LENGTH: 55
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (23)..(55)

<400> SEQUENCE: 4
ggguaauuug cgcgccugcu gctttaaaaa aaaaaaaaaa aaaaaaaaaa aaaaa        55

<210> SEQ ID NO 5
<211> LENGTH: 59
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (27)..(59)

<400> SEQUENCE: 5
uuucucaggc ucccucuccg gaaucgttta aaaaaaaaaa aaaaaaaaaa aaaaaaaa        59

<210> SEQ ID NO 6
<211> LENGTH: 57
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (25)..(57)

<400> SEQUENCE: 6
acaucugaau acgaaugucc ccaatttaaa aaaaaaaaaa aaaaaaaaaa aaaaaaa        57

<210> SEQ ID NO 7
<211> LENGTH: 56
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (24)..(56)
```

-continued

```
<400> SEQUENCE: 7
cuagucggca uaguuuaugg uuatttaaaa aaaaaaaaaa aaaaaaaaaa aaaaaa         56

<210> SEQ ID NO 8
<211> LENGTH: 57
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (25)..(57)

<400> SEQUENCE: 8
aaaaacggcc augcaucacc aucctttaaa aaaaaaaaaa aaaaaaaaaa aaaaaaa        57

<210> SEQ ID NO 9
<211> LENGTH: 54
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (22)..(54)

<400> SEQUENCE: 9
uaggccaaua cccuaccguc ctttaaaaaa aaaaaaaaaa aaaaaaaaaa aaaa           54

<210> SEQ ID NO 10
<211> LENGTH: 56
<212> TYPE: DNA
<213> ORGANISM: Artificial Sequence
<220> FEATURE:
<223> OTHER INFORMATION: Synthetic Oligonucleotide

<400> SEQUENCE: 10
aaagacuuug auuucucuca aggtttaaaa aaaaaaaaaa aaaaaaaaaa aaaaaa         56

<210> SEQ ID NO 11
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 11
ggauugggua auuugcgcgc cc                                            22

<210> SEQ ID NO 12
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 12
caagaaagag cuaucaaucu gucaaucc                                      28

<210> SEQ ID NO 13
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 13
```

-continued

```
cccguguuga gucaaauuaa gccgca                                       26

<210> SEQ ID NO 14
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 14
ggguaauuug cgcgccugcu gc                                           22

<210> SEQ ID NO 15
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 15
uuucucaggc ucccucuccg gaaucg                                       26

<210> SEQ ID NO 16
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 16
acaucugaau acgaaugucc ccaa                                         24

<210> SEQ ID NO 17
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 17
cuagucggca uaguuuaugg uua                                          23

<210> SEQ ID NO 18
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 18
aaaaacggcc augcaucacc aucc                                         24

<210> SEQ ID NO 19
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 19
uaggccaaua cccuaccguc c                                            21

<210> SEQ ID NO 20
<211> LENGTH: 23
<212> TYPE: DNA
```

-continued

```
<213> ORGANISM: Artificial Sequence
<220> FEATURE:
<223> OTHER INFORMATION: Synthetic Oligonucleotide

<400> SEQUENCE: 20
aaagacuuug auuucucuca agg                                          23

<210> SEQ ID NO 21
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 21
aatactacag catgg                                                   15

<210> SEQ ID NO 22
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 22
ggaaggcagc aggcgcgta                                               19

<210> SEQ ID NO 23
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 23
aatactacag catgga                                                  16

<210> SEQ ID NO 24
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 24
aatactacag catggaa                                                 17

<210> SEQ ID NO 25
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 25
atactacagc atggaata                                                18

<210> SEQ ID NO 26
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 26
attcagatgt cagaggtga                                               19
```

```
<210> SEQ ID NO 27
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 27
gtattcagat gtcagaggtg a                                        21

<210> SEQ ID NO 28
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 28
gttacgatta ataggagt                                           18

<210> SEQ ID NO 29
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 29
gttacgatta ataggagta                                          19

<210> SEQ ID NO 30
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 30
gttacgatta ataggagtag                                         20

<210> SEQ ID NO 31
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 31
gttacgatta ataggagtag c                                       21

<210> SEQ ID NO 32
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 32
aatactacag catggaat                                           18

<210> SEQ ID NO 33
<211> LENGTH: 19
<212> TYPE: DNA
<213> ORGANISM: Artificial Sequence
<220> FEATURE:
```

-continued

<223> OTHER INFORMATION: Synthetic Oligonucleotide

<400> SEQUENCE: 33
aatactacag catggaata                                                                                  19

<210> SEQ ID NO 34
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 34
tacgattaat aggagt                                                                                     16

<210> SEQ ID NO 35
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 35
tactacagca tggaata                                                                                    17

<210> SEQ ID NO 36
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 36
tattcagatg tcagaggtga                                                                                 20

<210> SEQ ID NO 37
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (6)..(6)
<223> OTHER INFORMATION: n means a or g or c or t/u, unknown, or other.

<400> SEQUENCE: 37
tcagtncctt atgagaaatc                                                                                 20

<210> SEQ ID NO 38
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 38
tggcttagtt acgatt                                                                                     16

<210> SEQ ID NO 39
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 39

-continued

```
tggcttagtt acgattaata g                                          21

<210> SEQ ID NO 40
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 40
ttaataggag tagcttgggg                                            20

<210> SEQ ID NO 41
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 41
ttacgattaa taggagt                                               17

<210> SEQ ID NO 42
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 42
ttcagatgtc agaggtga                                              18

<210> SEQ ID NO 43
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 43
ttggcttagt tacgat                                                16

<210> SEQ ID NO 44
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 44
ttggcttagt tacgatta                                              18

<210> SEQ ID NO 45
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 45
ttggggacat tcgtattcag a                                          21

<210> SEQ ID NO 46
<211> LENGTH: 20
<212> TYPE: DNA
```

-continued

```
<213> ORGANISM: Artificial Sequence
<220> FEATURE:
<223> OTHER INFORMATION: Synthetic Oligonucleotide

<400> SEQUENCE: 46
tttagattgc ttccttcagt                                                    20

<210> SEQ ID NO 47
<211> LENGTH: 16
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (12)..(12)
<223> OTHER INFORMATION: n means a or g or c or t/u, unknown, or other.

<400> SEQUENCE: 47
tttgaatact anagca                                                        16

<210> SEQ ID NO 48
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 48
acattcgtat tcagatgtca g                                                  21

<210> SEQ ID NO 49
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 49
cttagttacg attaatagga                                                    20

<210> SEQ ID NO 50
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 50
cgattaatag gagtagcttg g                                                  21

<210> SEQ ID NO 51
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 51
cttagttacg attaatagga gtag                                               24

<210> SEQ ID NO 52
<211> LENGTH: 16
<212> TYPE: DNA
<213> ORGANISM: Artificial Sequence
<220> FEATURE:
<223> OTHER INFORMATION: Synthetic Oligonucleotide
```

-continued

```
<220> FEATURE:
<221> NAME/KEY: misc_feature
<222> LOCATION: (11)..(11)
<223> OTHER INFORMATION: n means a or g or c or t/u, unknown, or other.

<400> SEQUENCE: 52
cttgaatact ncagca                                               16

<210> SEQ ID NO 53
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 53
ggcttagtta cgatta                                               16

<210> SEQ ID NO 54
<211> LENGTH: 15
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (8)..(8)
<223> OTHER INFORMATION: n means a or g or c or t/u, unknown, or other.

<400> SEQUENCE: 54
aatactanag catgg                                                15

<210> SEQ ID NO 55
<211> LENGTH: 19
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (8)..(8)
<223> OTHER INFORMATION: n means a or g or c or t/u, unknown, or other.

<400> SEQUENCE: 55
aatactanag catggaata                                            19

<210> SEQ ID NO 56
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 56
aattctaaag aagagag                                              17

<210> SEQ ID NO 57
<211> LENGTH: 52
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)

<400> SEQUENCE: 57
aatttaatac gactcactat agggagattc actcccttaa ctttcgttct tg       52
```

```
<210> SEQ ID NO 58
<211> LENGTH: 51
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)

<400> SEQUENCE: 58
aatttaatac gactcactat agggagactt gattaatgga agtattttag a           51

<210> SEQ ID NO 59
<211> LENGTH: 56
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)

<400> SEQUENCE: 59
aatttaatac gactcactat agggagactt aactttcgtt cttgattaat ggaagt      56

<210> SEQ ID NO 60
<211> LENGTH: 47
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)

<400> SEQUENCE: 60
aatttaatac gactcactat agggagacct actcttgtct taaacta              47

<210> SEQ ID NO 61
<211> LENGTH: 53
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)

<400> SEQUENCE: 61
aatttaatac gactcactat agggagaaaa cggccatgca tcaccatcca aga          53

<210> SEQ ID NO 62
<211> LENGTH: 60
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)

<400> SEQUENCE: 62
aatttaatac gactcactat agggagactc ccttaacttt cgttcttgat taatggaagt   60

<210> SEQ ID NO 63
<211> LENGTH: 54
```

```
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)

<400> SEQUENCE: 63
aatttaatac gactcactat agggagacga cggtatctga tcgtcttcac tccc          54

<210> SEQ ID NO 64
<211> LENGTH: 55
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)

<400> SEQUENCE: 64
aatttaatac gactcactat agggagactt aactttcgtt cttgattaat ggaag          55

<210> SEQ ID NO 65
<211> LENGTH: 57
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)

<400> SEQUENCE: 65
aatttaatac gactcactat agggagactt aactttcgtt cttgattaat ggaagta          57

<210> SEQ ID NO 66
<211> LENGTH: 57
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)

<400> SEQUENCE: 66
aatttaatac gactcactat agggagacac tcccttaact ttcgttcttg attaatg          57

<210> SEQ ID NO 67
<211> LENGTH: 58
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)

<400> SEQUENCE: 67
aatttaatac gactcactat agggagacac tcccttaact ttcgttcttg attaatgg          58

<210> SEQ ID NO 68
<211> LENGTH: 56
<212> TYPE: DNA
<213> ORGANISM: Artificial Sequence
<220> FEATURE:
<223> OTHER INFORMATION: Synthetic Oligonucleotide
```

```
<220> FEATURE:
<221> NAME/KEY: promoter
<222> LOCATION: (1)..(27)

<400> SEQUENCE: 68
aatttaatac gactcactat agggagactt cactcccttta actttcgttc ttgatt          56

<210> SEQ ID NO 69
<211> LENGTH: 55
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)

<400> SEQUENCE: 69
aatttaatac gactcactat agggagactt cactcccttta actttcgttc ttgat          55

<210> SEQ ID NO 70
<211> LENGTH: 55
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)

<400> SEQUENCE: 70
aatttaatac gactcactat agggagaatc gtcttcactc ccttaacttt cgttc          55

<210> SEQ ID NO 71
<211> LENGTH: 55
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)

<400> SEQUENCE: 71
aatttaatac gactcactat agggagactc ccttaacttt cgttcttgat taatg          55

<210> SEQ ID NO 72
<211> LENGTH: 53
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)

<400> SEQUENCE: 72
aatttaatac gactcactat agggagatca ctcccttaac tttcgttctt gat          53

<210> SEQ ID NO 73
<211> LENGTH: 53
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)
```

-continued

```
<400> SEQUENCE: 73
aatttaatac gactcactat agggagaccc ttaactttcg ttcttgatta atg                53

<210> SEQ ID NO 74
<211> LENGTH: 51
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)

<400> SEQUENCE: 74
aatttaatac gactcactat agggagactt aactttcgtt cttgattaat g                  51

<210> SEQ ID NO 75
<211> LENGTH: 49
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)

<400> SEQUENCE: 75
aatttaatac gactcactat agggagataa ctttcgttct tgattaatg                     49

<210> SEQ ID NO 76
<211> LENGTH: 51
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)

<400> SEQUENCE: 76
aatttaatac gactcactat agggagaact cccttaactt tcgttcttga t                  51

<210> SEQ ID NO 77
<211> LENGTH: 49
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)

<400> SEQUENCE: 77
aatttaatac gactcactat agggagatcc cttaactttc gttcttgat                     49

<210> SEQ ID NO 78
<211> LENGTH: 55
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)
<220> FEATURE:
<221> NAME/KEY: misc_feature
<222> LOCATION: (51)..(51)
<223> OTHER INFORMATION: n means a or g or c or t/u, unknown, or other.
```

<400> SEQUENCE: 78
aatttaatac gactcactat agggagaagg caaatgcttt cgcagttgtt ngtct          55

<210> SEQ ID NO 79
<211> LENGTH: 55
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)

<400> SEQUENCE: 79
aatttaatac gactcactat agggagaagg caaatgcttt cgcagttgtt tgtct          55

<210> SEQ ID NO 80
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 80
ttcactccct taactttcgt tcttg                                          25

<210> SEQ ID NO 81
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 81
cttgattaat ggaagtattt taga                                           24

<210> SEQ ID NO 82
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 82
cttaactttc gttcttgatt aatggaagt                                      29

<210> SEQ ID NO 83
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 83
cctactcttg tcttaaacta                                                20

<210> SEQ ID NO 84
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 84
aaacggccat gcatcaccat ccaaga                                         26

<210> SEQ ID NO 85
<211> LENGTH: 33
<212> TYPE: DNA
<213> ORGANISM: Artificial Sequence
<220> FEATURE:
<223> OTHER INFORMATION: Synthetic Oligonucleotide

<400> SEQUENCE: 85
ctcccttaac tttcgttctt gattaatgga agt                                  33

<210> SEQ ID NO 86
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 86
cgacggtatc tgatcgtctt cactccc                                         27

<210> SEQ ID NO 87
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 87
cttaactttc gttcttgatt aatggaag                                        28

<210> SEQ ID NO 88
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 88
cttaactttc gttcttgatt aatggaagta                                      30

<210> SEQ ID NO 89
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 89
cactccctta actttcgttc ttgattaatg                                      30

<210> SEQ ID NO 90
<211> LENGTH: 31
<212> TYPE: DNA
<213> ORGANISM: Artificial Sequence
<220> FEATURE:
<223> OTHER INFORMATION: Synthetic Oligonucleotide

<400> SEQUENCE: 90
cactccctta actttcgttc ttgattaatg g                                    31

<210> SEQ ID NO 91
<211> LENGTH: 29
<212> TYPE: DNA
<213> ORGANISM: Artificial Sequence
<220> FEATURE:
<223> OTHER INFORMATION: Synthetic Oligonucleotide -continued

```
<400> SEQUENCE: 91
cttcactccc ttaactttcg ttcttgatt                                   29

<210> SEQ ID NO 92
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 92
cttcactccc ttaactttcg ttcttgat                                    28

<210> SEQ ID NO 93
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 93
atcgtcttca ctcccttaac tttcgttc                                    28

<210> SEQ ID NO 94
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 94
ctcccttaac tttcgttctt gattaatg                                    28

<210> SEQ ID NO 95
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 95
tcactccctt aactttcgtt cttgat                                      26

<210> SEQ ID NO 96
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 96
cccttaactt tcgttcttga ttaatg                                      26

<210> SEQ ID NO 97
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 97
cttaactttc gttcttgatt aatg                                        24

<210> SEQ ID NO 98
```

```
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 98
taactttcgt tcttgattaa tg                                                      22

<210> SEQ ID NO 99
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 99
actcccttaa ctttcgttct tgat                                                    24

<210> SEQ ID NO 100
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 100
tcccttaact ttcgttcttg at                                                      22

<210> SEQ ID NO 101
<211> LENGTH: 28
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (24)..(24)
<223> OTHER INFORMATION: n means a or g or c or t/u, unknown, or other.

<400> SEQUENCE: 101
aggcaaatgc tttcgcagtt gttngtct                                                28

<210> SEQ ID NO 102
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 102
aggcaaatgc tttcgcagtt gtttgtct                                                28

<210> SEQ ID NO 103
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 103
cgcgcaagcg agaaagcgcg                                                         20

<210> SEQ ID NO 104
<211> LENGTH: 22
<212> TYPE: DNA
<213> ORGANISM: Artificial Sequence
```

<220> FEATURE:
<223> OTHER INFORMATION: Synthetic Oligonucleotide

<400> SEQUENCE: 104
gcucgcauuc gcgcaagcga gc                                          22

<210> SEQ ID NO 105
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 105
gcuugcgagu auucgcgcaa gc                                          22

<210> SEQ ID NO 106
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 106
ggcaagcgag aaagucuugc c                                           21

<210> SEQ ID NO 107
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 107
ccgagguauu cgcgcaacuc gg                                          22

<210> SEQ ID NO 108
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 108
ggcucacuuu cucgcuugga gcc                                         23

<210> SEQ ID NO 109
<211> LENGTH: 21
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (11)..(11)
<223> OTHER INFORMATION: n means a or g or c or t/u, unknown, or other.

<400> SEQUENCE: 109
cucuggagac nagcaccaga g                                           21

<210> SEQ ID NO 110
<211> LENGTH: 18
<212> TYPE: DNA
<213> ORGANISM: Artificial Sequence
<220> FEATURE:
<223> OTHER INFORMATION: Synthetic Oligonucleotide -continued

```
<400> SEQUENCE: 110
gucucauuuu cuggagac                                               18

<210> SEQ ID NO 111
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 111
gccuaaaaua cuuccuaggc                                             20

<210> SEQ ID NO 112
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 112
cauggaaaua cuuccaug                                               18

<210> SEQ ID NO 113
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 113
ccgagauuuu cuggagaccu cgg                                         23

<210> SEQ ID NO 114
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 114
ccgaggccua aaauacuucc cucgg                                       25

<210> SEQ ID NO 115
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 115
gggaauuuaa aaccuuccc                                              19

<210> SEQ ID NO 116
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 116
ggaaggaauu uaaaaccuuc c                                           21

<210> SEQ ID NO 117
<211> LENGTH: 21
```

-continued

```
<212> TYPE: DNA
<213> ORGANISM: Artificial Sequence
<220> FEATURE:
<223> OTHER INFORMATION: Synthetic Oligonucleotide

<400> SEQUENCE: 117
gugggaauuu aaaaccccca c                                            21

<210> SEQ ID NO 118
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 118
uccagaaauu cuuagauuuu cugga                                        25

<210> SEQ ID NO 119
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 119
acuccgaacg aaaguuaagg gagu                                         24

<210> SEQ ID NO 120
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 120
agggagugaa gacgaucauc ccu                                          23

<210> SEQ ID NO 121
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 121
ucgcgcaagc gagaaaggcg cga                                          23

<210> SEQ ID NO 122
<211> LENGTH: 23
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (9)..(9)
<223> OTHER INFORMATION: n means a or g or c or t/u, unknown, or other.

<400> SEQUENCE: 122
ccgaagugnc uaaaauacuu cgg                                          23

<210> SEQ ID NO 123
<211> LENGTH: 20
<212> TYPE: DNA
<213> ORGANISM: Artificial Sequence
<220> FEATURE:
```

-continued

<223> OTHER INFORMATION: Synthetic Oligonucleotide

<400> SEQUENCE: 123
caccucagau gucagaggug                                                  20

<210> SEQ ID NO 124
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 124
cuaccucuaa agaagagagg uag                                              23

<210> SEQ ID NO 125
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 125
cgcgcaagcg agaaag                                                      16

<210> SEQ ID NO 126
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 126
auucgcgcaa gcgagc                                                      16

<210> SEQ ID NO 127
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 127
gaguauucgc gcaagc                                                      16

<210> SEQ ID NO 128
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 128
ggcaagcgag aaagu                                                       15

<210> SEQ ID NO 129
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 129
guauucgcgc aa                                                          12

-continued

```
<210> SEQ ID NO 130
<211> LENGTH: 13
<212> TYPE: DNA
<213> ORGANISM: Artificial Sequence
<220> FEATURE:
<223> OTHER INFORMATION: Synthetic Oligonucleotide

<400> SEQUENCE: 130
acuuucucgc uug                                                      13

<210> SEQ ID NO 131
<211> LENGTH: 15
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (11)..(11)
<223> OTHER INFORMATION: n means a or g or c or t/u, unknown, or other.

<400> SEQUENCE: 131
cucuggagac nagca                                                    15

<210> SEQ ID NO 132
<211> LENGTH: 13
<212> TYPE: DNA
<213> ORGANISM: Artificial Sequence
<220> FEATURE:
<223> OTHER INFORMATION: Synthetic Oligonucleotide

<400> SEQUENCE: 132
auuuucugga gac                                                      13

<210> SEQ ID NO 133
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 133
gccuaaaaua cuucc                                                    15

<210> SEQ ID NO 134
<211> LENGTH: 13
<212> TYPE: DNA
<213> ORGANISM: Artificial Sequence
<220> FEATURE:
<223> OTHER INFORMATION: Synthetic Oligonucleotide

<400> SEQUENCE: 134
aaauacuucc aug                                                      13

<210> SEQ ID NO 135
<211> LENGTH: 13
<212> TYPE: DNA
<213> ORGANISM: Artificial Sequence
<220> FEATURE:
<223> OTHER INFORMATION: Synthetic Oligonucleotide

<400> SEQUENCE: 135
auuuucugga gac                                                      13

<210> SEQ ID NO 136
<211> LENGTH: 13
<212> TYPE: DNA
```

-continued

<213> ORGANISM: Artificial Sequence
<220> FEATURE:
<223> OTHER INFORMATION: Synthetic Oligonucleotide

<400> SEQUENCE: 136
ccuaaaauac uuc                                                                          13

<210> SEQ ID NO 137
<211> LENGTH: 14
<212> TYPE: DNA
<213> ORGANISM: Artificial Sequence
<220> FEATURE:
<223> OTHER INFORMATION: Synthetic Oligonucleotide

<400> SEQUENCE: 137
gggaauuuaa aacc                                                                         14

<210> SEQ ID NO 138
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 138
ggaauuuaaa accuucc                                                                      17

<210> SEQ ID NO 139
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 139
gugggaauuu aaaacc                                                                       16

<210> SEQ ID NO 140
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 140
gaaauucuua gauuuucugg a                                                                 21

<210> SEQ ID NO 141
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 141
gaacgaaagu uaagggagu                                                                    19

<210> SEQ ID NO 142
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 142
agggagugaa gacgauca                                                                     18

-continued

```
<210> SEQ ID NO 143
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 143
ucgcgcaagc gagaaag                                                              17

<210> SEQ ID NO 144
<211> LENGTH: 17
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (3)..(3)
<223> OTHER INFORMATION: n means a or g or c or t/u, unknown, or other.

<400> SEQUENCE: 144
ugncuaaaau acuucgg                                                              17

<210> SEQ ID NO 145
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 145
cagaugucag aggug                                                                15

<210> SEQ ID NO 146
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 146
ucuaaagaag agagguag                                                             18

<210> SEQ ID NO 147
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 147
ucuuagauuu ucuggagac                                                            19

<210> SEQ ID NO 148
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 148
uucagauguc agagg                                                                15

<210> SEQ ID NO 149
```

-continued

```
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 149
uucagauguc agaggt                                                          16

<210> SEQ ID NO 150
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 150
uauucagaug ucagaggt                                                        18

<210> SEQ ID NO 151
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 151
uauucagaug ucagaggug                                                       19

<210> SEQ ID NO 152
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 152
ucagauguca gaggt                                                           15

<210> SEQ ID NO 153
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 153
uucagauguc agaggt                                                          16

<210> SEQ ID NO 154
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 154
auucagaugu cagaggt                                                         17

<210> SEQ ID NO 155
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 155
```

-continued auucagaugu cagaggug                                                    18

<210> SEQ ID NO 156
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 156
cuuagauuuu cuggaga                                                     17

<210> SEQ ID NO 157
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 157
cuuagauuuu cuggagac                                                    18

<210> SEQ ID NO 158
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 158
cuuaguuacg auuaauagga                                                  20

<210> SEQ ID NO 159
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 159
guauucagau gucagaggug a                                                21

<210> SEQ ID NO 160
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 160
auucuuagau uuucuggaga c                                                21

<210> SEQ ID NO 161
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 161
cuaagauuuu cuggagac                                                    18

<210> SEQ ID NO 162
<211> LENGTH: 23
<212> TYPE: DNA

-continued

```
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (12)..(12)
<223> OTHER INFORMATION: n means a or g or c or t/u, unknown, or other.

<400> SEQUENCE: 162
tttgaatact anagcatgga ata                                              23

<210> SEQ ID NO 163
<211> LENGTH: 10
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (6)..(6)
<223> OTHER INFORMATION: n means a or g or c or t/u, unknown, or other.

<400> SEQUENCE: 163 tactanagca                                                             10

<210> SEQ ID NO 164
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 164
tttgaatact acagcatgga ata                                              23

<210> SEQ ID NO 165
<211> LENGTH: 10
<212> TYPE: DNA
<213> ORGANISM: Artificial Sequence
<220> FEATURE:
<223> OTHER INFORMATION: Synthetic Oligonucleotide

<400> SEQUENCE: 165
tactacagca                                                             10

<210> SEQ ID NO 166
<211> LENGTH: 35
<212> TYPE: DNA
<213> ORGANISM: Artificial Sequence
<220> FEATURE:
<223> OTHER INFORMATION: Synthetic Oligonucleotide

<400> SEQUENCE: 166
ttggcttagt tacgattaat aggagtagct tgggg                                 35

<210> SEQ ID NO 167
<211> LENGTH: 11
<212> TYPE: DNA
<213> ORGANISM: Artificial Sequence
<220> FEATURE:
<223> OTHER INFORMATION: Synthetic Oligonucleotide

<400> SEQUENCE: 167
ttaataggag t                                                           11

<210> SEQ ID NO 168
<211> LENGTH: 14
```

-continued

```
<212> TYPE: DNA
<213> ORGANISM: Artificial Sequence
<220> FEATURE:
<223> OTHER INFORMATION: Synthetic Oligonucleotide

<400> SEQUENCE: 168
ggcttagtta cgat                                                         14

<210> SEQ ID NO 169
<211> LENGTH: 63
<212> TYPE: DNA
<213> ORGANISM: Artificial Sequence
<220> FEATURE:
<223> OTHER INFORMATION: Synthetic Oligonucleotide

<400> SEQUENCE: 169
cgacggtatc tgatcgtctt cactccctta actttcgttc ttgattaatg gaagtatttt    60
aga                                                                    63

<210> SEQ ID NO 170
<211> LENGTH: 51
<212> TYPE: DNA
<213> ORGANISM: Artificial Sequence
<220> FEATURE:
<223> OTHER INFORMATION: Synthetic Oligonucleotide

<400> SEQUENCE: 170
atcgtcttca ctcccttaac tttcgttctt gattaatgga agtatttag a               51

<210> SEQ ID NO 171
<211> LENGTH: 11
<212> TYPE: DNA
<213> ORGANISM: Artificial Sequence
<220> FEATURE:
<223> OTHER INFORMATION: Synthetic Oligonucleotide

<400> SEQUENCE: 171
cttgattaat g                                                           11

<210> SEQ ID NO 172
<211> LENGTH: 12
<212> TYPE: DNA
<213> ORGANISM: Artificial Sequence
<220> FEATURE:
<223> OTHER INFORMATION: Synthetic Oligonucleotide

<400> SEQUENCE: 172
taactttcgt tc                                                          12

<210> SEQ ID NO 173
<211> LENGTH: 10
<212> TYPE: DNA
<213> ORGANISM: Artificial Sequence
<220> FEATURE:
<223> OTHER INFORMATION: Synthetic Oligonucleotide

<400> SEQUENCE: 173
cttcactccc                                                             10

<210> SEQ ID NO 174
<211> LENGTH: 14
<212> TYPE: DNA
<213> ORGANISM: Artificial Sequence
<220> FEATURE:
<223> OTHER INFORMATION: Synthetic Oligonucleotide
```

<400> SEQUENCE: 174
ucagauguca gagg                                                                    14

<210> SEQ ID NO 175
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 175
cuaagauuuu cuggaga                                                                 17

<210> SEQ ID NO 176
<211> LENGTH: 13
<212> TYPE: DNA
<213> ORGANISM: Artificial Sequence
<220> FEATURE:
<223> OTHER INFORMATION: Synthetic Oligonucleotide

<400> SEQUENCE: 176
cagaugucag agg                                                                     13

<210> SEQ ID NO 177
<211> LENGTH: 10
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: y means t/u or c

<400> SEQUENCE: 177 yucuggagac                                                                         10

<210> SEQ ID NO 178
<211> LENGTH: 10
<212> TYPE: DNA
<213> ORGANISM: Artificial Sequence
<220> FEATURE:
<223> OTHER INFORMATION: Synthetic Oligonucleotide

<400> SEQUENCE: 178
auuuucugga                                                                         10

<210> SEQ ID NO 179
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 179
aatttaatac gactcactat agggaga                                                      27

<210> SEQ ID NO 180
<211> LENGTH: 2087
<212> TYPE: DNA
<213> ORGANISM: Plasmodium falciparum
<300> PUBLICATION INFORMATION:
<308> DATABASE ACCESSION NUMBER: XR_002273081.2
<309> DATABASE ENTRY DATE: 2018-03-28
<313> RELEVANT RESIDUES IN SEQ ID NO: (1)..(2087)

<400> SEQUENCE: 180

```
aacctggttg atcttgccag tagtcatatg cttgtctcaa agattaagcc atgcaagtga        60
aagtatatat atattttata tgtagaaact gcgaacggct cattaaaaca gttatagtct       120
acttgacatt tttattataa ggataactac ggaaaagctg tagctaatac ttgctttatt       180
atcctttgat ttttatcttt ggataagtat ttgttaggcc ttataagaaa aaagttatta       240
acttaaggaa ttataacaaa gaagtaacac gtaataaatt tattttatt agtgtgtatc        300 aatcgagttt ctgacctatc agcttttgat gttaggtat tggcctaaca tggctatgac        360
gggtaacggg gaattagagt tcgattccgg agagggagcc tgagaaatag ctaccacatc       420
taaggaaggc agcaggcgcg taaattaccc aattctaaag aagagaggta gtgacaagaa       480
ataacaatgc aaggccaatt tttggttttg taattggaat ggtgggaatt taaaaccttc       540
ccagagtaac aattggaggg caagtctggt gccagcagcc gcggtaattc cagctccaat       600
agcgtatatt aaaattgttg cagttaaaac gctcgtagtt gaatttcaaa gaatcgatat       660
tttattgtaa ctattctagg gaactattt tagctttcgc tttaatacgc ttcctctatt        720
attatgttct ttaaataaca aagattcttt ttaaaatccc cacttttgct tttgctttt        780 ggggattttg ttactttgag taaattagag tgttcaaagc aaacagttaa agcatttact       840
gtgtttgaat actatagcat ggaataacaa aattgaacaa gctaaaattt tttgttcttt       900
tttcttattt tggcttagtt acgattaata ggagtagctt ggggacattc gtattcagat       960
gtcagaggtg aaattcttag attttctgga gacgaacaac tgcgaaagca tttgtctaaa      1020
atacttccat taatcaagaa cgaaagttaa gggagtgaag acgatcagat accgtcgtaa      1080
tcttaaccat aaactatgcc gactaggtgt tggatgaaag tgttaaaaat aaaagtcatc      1140
tttcgaggtg acttttagat tgcttccttc agtaccttat gagaaatcaa agtctttggg      1200
ttctggggcg agtattcgcg caagcgagaa agttaaaaga attgacggaa gggcaccacc      1260
aggcgtggag cttgcggctt aatttgactc aacacgggga aactcactag tttaagacaa      1320
gagtaggatt gacagattaa tagctctttc ttgatttctt ggatggtgat gcatggccgt      1380
ttttagttcg tgaatatgat ttgtctggtt aattccgata acgaacgaga tcttaacctg      1440
ctaattagcg gcgagtacac tatattctta tttgaaattg aacataggta actatacatt      1500
tattcagtaa tcaaattagg atatttttat taaaatatcc ttttccctgt tctactaata      1560
atttgttttt tactctattt ctctcttctt ttaagaatgt acttgcttga ttgaaaagct      1620
tcttagagga acattgtgtg tctaacacaa ggaagtttaa ggcaacaaca ggtctgtgat      1680
gtccttagat gaactaggct gcacgcgtgc tacactgata tataacga gttttttaaaa      1740 atatgcttat atttgtatct ttgcttatat tttgcatact tttcctccgc cgaaaggcgt      1800
aggtaatctt tatcaatata tatcgtgatg gggatagatt attgcaatta ttaatcttga      1860
acgaggaatg cctagtaagc atgattcatc agattgtgct gactacgtcc ctgccctttg      1920
tacacaccgc ccgtcgctcc taccgattga aagatatgat gaattgtttg dacaagaaaa      1980
attgaattat attctttttt tttctggaaa aaccgtaaat cctatctttt aaaggaagga      2040
gaagtcgtaa caaggtttcc gtaggtgaac ctgcggaagg atcatta              2087
```

<210> SEQ ID NO 181
<211> LENGTH: 56
<212> TYPE: DNA
<213> ORGANISM: Artificial Sequence
<220> FEATURE:
<223> OTHER INFORMATION: Synthetic Oligonucleotide
<220> FEATURE:

```
<221> NAME/KEY: promoter
<222> LOCATION: (1)..(27)
<220> FEATURE:
<221> NAME/KEY: misc_feature
<222> LOCATION: (43)..(43)
<223> OTHER INFORMATION: n means a or g or c or t/u, unknown, or other.

<400> SEQUENCE: 181
aatttaatac gactcactat agggagatca agaaagagct atnaatctgt caatcc          56

<210> SEQ ID NO 182
<211> LENGTH: 29
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (16)..(16)
<223> OTHER INFORMATION: n means a or g or c or t/u, unknown, or other.

<400> SEQUENCE: 182
tcaagaaaga gctatnaatc tgtcaatcc                                         29

<210> SEQ ID NO 183
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 183
gaaatcaaag tctttgggtt ctg                                              23

<210> SEQ ID NO 184
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 184
caaagtcttt gggttctgg                                                   19

<210> SEQ ID NO 185
<211> LENGTH: 53
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (21)..(21)
<223> OTHER INFORMATION: n means a or g or c or t/u, unknown, or other.

<400> SEQUENCE: 185
tttagattgc ttccttcagt nccttatgag aaatcaaagt ctttgggttc tgg             53

<210> SEQ ID NO 186
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 186
gaaatcaaag tctttgggtt ctgg                                             24
```

```
<210> SEQ ID NO 187
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 187
caaagtcttt gggttctg                                                18

<210> SEQ ID NO 188
<211> LENGTH: 75
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (44)..(44)
<223> OTHER INFORMATION: n means a or g or c or t/u, unknown, or other.

<400> SEQUENCE: 188
aaacggccat gcatcaccat ccaagaaatc aagaaagagc tatnaatctg tcaatcctac     60
tcttgtctta aacta                                                     75

<210> SEQ ID NO 189
<211> LENGTH: 24
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (10)..(10)
<223> OTHER INFORMATION: s means g or c.

<400> SEQUENCE: 189
gaguauucgs gcaagcgaga aagu                                           24

<210> SEQ ID NO 190
<211> LENGTH: 10
<212> TYPE: DNA
<213> ORGANISM: Artificial Sequence
<220> FEATURE:
<223> OTHER INFORMATION: Synthetic Oligonucleotide

<400> SEQUENCE: 190
auucgcgcaa                                                           10

<210> SEQ ID NO 191

<400> SEQUENCE: 191

000

<210> SEQ ID NO 192
<211> LENGTH: 1557
<212> TYPE: DNA
<213> ORGANISM: Plasmodium vivax
<300> PUBLICATION INFORMATION:
<308> DATABASE ACCESSION NUMBER: JQ627153.1
<309> DATABASE ENTRY DATE: 2012-08-14
<313> RELEVANT RESIDUES IN SEQ ID NO: (1)..(1557)

<400> SEQUENCE: 192
caaagattac gccatgcaag tgaaagtata tgcatatttt atatgtagaa actgcgaacg     60
```

```
gctcattaaa acagttataa tctacttgac attttttcta taaggataac tacggaaaag      120
ctgtagctaa tacttgcttt agcactcttg attcatttct tgagtgtgta cttgttaagc      180
cttttaagaa aaaagttatt aacttaagga attataacaa agaagcgaca cgtaatggat      240
ccgtccattt ttagtgtgta tcaatcgagt ttctgaccta tcagcttttg atgttagggt      300
attggcctaa catggctatg acgggtaacg gggaattaga gttcgattcc ggagagggag      360
cctgagaaat agctaccaca tctaaggaag gcagcaggcg cgtaaattac ccaattctaa      420
agaagagagg tagtgacaag aaataacaat acaaggccaa tctggctttg taattggaat      480
gatgggaatt taaaaccttc ccaaaactca attggagggc aagtctggtg ccagcagccg      540
cggtaattcc agctccaata gcgtatatta aaattgttgc agttaaaacg ctcgtagttg      600
aatttcaaag aatcgatatt ttaagcaacg cttctagctt aatccacata actgatactt      660
cgtatcgact ttgtgcgcat tttgctatta tgtgttcttt aattaaaat gattcttttt       720 aaggactttc tttgcttcgg cttggaatcc cttgttactt tgagtaaatt agagtgttca      780
aagcaaacag atatagcatt gcgcgtttga atactacagc atggaataac aaaattgaac      840
aagtcagaat tttgttcttt tttcttattt tggcttagtt acgattaata ggagtagctt      900
gggggcattt gtattcagat gtcagaggtg aaattcttag attttctgga gacaaacaac      960
tgcgaaagca tttgcctaaa atacttccat taatcaagaa cgaaagttaa gggagtgaag     1020
acgatcagat accgtcgtaa tcttaaccat aaactatgcc gactaggctt ggatgaaag      1080 attttaaaat aagaattttc tcttcggagt ttattcttag attgcttcct tcagtgcctt     1140
atgagaaatc aaagtctttg ggttctgggg cgagtattcg cgcaagcgag aaagttaaaa     1200
gaattgacgg aagggcacca ccaggcgtgg agcttgcggc ttaatttgac tcaacacggg     1260
aaaactcact agtttaagac aagagtagga ttgacagatt aatagctctt tcttgatttc     1320
ttggatggtg atgcatggcc gttttagtt cgtgaatatg atttgtctgg ttaattccga     1380
taacgaacga tcttaacc tgctaattag cggcaaatac gatatattct tacgtgggac       1440
tgaattcggt tgatttgctt actttgaaga aaatattggg atacgtaaca gtttccttt       1500 cccttttcta cttagttcgc ttttcatact gtttcttttt cgcgtaagaa tgtattt       1557
```

```
<210> SEQ ID NO 193
<211> LENGTH: 2096
<212> TYPE: DNA
<213> ORGANISM: Plasmodium knowlesi
<300> PUBLICATION INFORMATION:
<308> DATABASE ACCESSION NUMBER: L07560.1
<309> DATABASE ENTRY DATE: 2008-10-02
<313> RELEVANT RESIDUES IN SEQ ID NO: (1)..(2096)

<400> SEQUENCE: 193
```

```
aacctggttg atcttgccag tagtcatatg cttgtctcaa agattaagcc atgcaagtga       60
aagtatatgc atattttata tgtagaaact gcgaacggct cattaaaaca gttataatct      120
acttgacatt ttctatataa ggataactac ggaaaagctg tagctaatac ttgctttagc      180
actcttgatt tctttcttga gtgtgtactt gttaagcctt ataagaaaag agttattaac      240
ttaaggaatt ataacaaaga gtaacacgt aatggattct tccattttta gtgtgtatca       300
atcgagtttc tgacctatca gcttttgatg ttagggtatt ggcctaacat ggctatgacg      360
ggtaacgggg aattagagtt cgattccgga gagggagcct gagaaatagc taccacatct      420
aaggaaggca gcaggcgcgt aaattaccca attctaaaga agagaggtag tgacaagaaa      480
taacaataca aggccaatct ggctttgtaa ttggaatgat gggaatttaa aaccttccca      540
```

```
aaaattcaatt ggagggcaag tctggtgcca gcagccgcgg taattccagc tccaatagcg      600
tatattaaaa ttgttgcagt taaaacgctc gtagttgaat ttcaaagaat cgatatttta      660
agcaacgctt ctagctataa atccacataa ctgatgcctc cgcgtatcga ctttgtgcgc      720 atttttagcta ttatgtgttc ttttaattaa aatgattctt tttaagattc atctattaaa     780
aattcgcttc ggcataattt ttttgatgat cttgttactt tgagtaaatt agagtgttca      840
aagcaaacag atatagcatt tgtgcgtttg aatactacag catggaataa caaaattgaa      900
caagtcagaa ttttttttgtt cttttttcctt attttggctt agttacgatt aataggagta    960 gcttggggggc atttgtattc agatgtcaga ggtgaaattc ttagattttc tggagacaaa     1020
caactgcgaa agcatttgcc taaaatactt ccattaatca agaacgaaag ttaagggagt       1080
gaagacgatc agataccgtc gtaatcttaa ccataaacta tgccgactag gctttggatg       1140
aaagatttta aaataagagt ttttcttttc tctccggaga ttagaactct tagattgctt       1200
ccttcagtgc cttatgagaa atcaaagtct ttgggttctg gggcgagtat cgcgcaagc       1260 gagaaagtta aaagaattga cggaagggca ccaccaggcg tggagcttgc ggcttaattt      1320
gactcaacac gggaaaactc actagtttaa gacaagagta ggattgacag attaatagct       1380
ctttcttgat ttcttggatg gtgatgcatg gccgttttta gttcgtgaat atgatttgtc       1440
tggttaattc cgataacgaa cgagatctta acctgctaat tagcggcaaa tacgatatat      1500
tcttatgtag aattgaatat agtggatttg ttagattttg aagaaaatat tggaattacg       1560
ttaaatgtga ttcctttccc ttttctactt aatttacatt tccatctatt tcttttttgc       1620
gtatgaatgt atttgcttga ttgtaaagct tcttagagga acgatgtgtg tctaacacaa       1680
ggaagtttaa ggcaacaaca ggtctgtgat gtccttagat gaactaggct gcacgcgtgc       1740
tacactgata tgtataacga gttactaaaa ttacgatttt agctgcttgc agtttatttt       1800 cgtactttttc ctccactgaa aagtgtaggt aatctttatc aatacatatc gtgatgggga      1860
tagattattg caattattaa tcttgaacga ggaatgccta gtaagcatga ttcatcagat       1920
tgtgctgact acgtccctgc cctttgtaca caccgcccgt cgctcctacc gattgaaaga      1980
tatgatgaat tgtttggaca agaaaaaatt ggattatatc tttttttttg gaaaaaccgt       2040
aaatcctatc tttttaaagga aggagaagtc gtaacaaggt ttccgtaggt gaattc         2096
```

<210> SEQ ID NO 194
<211> LENGTH: 2091
<212> TYPE: DNA
<213> ORGANISM: Plasmodium ovale
<300> PUBLICATION INFORMATION:
<308> DATABASE ACCESSION NUMBER: AB182491.1
<309> DATABASE ENTRY DATE: 2007-07-24
<313> RELEVANT RESIDUES IN SEQ ID NO: (1)..(2091)

<400> SEQUENCE: 194

```
aacctggttg atcttgccag tagtcatatg cttgtctcaa agattaagcc atgcaagtga       60
aagtatatgc atattttata tgtagaaact gcgaacggct cattaaaaca gttataatct       120
acttgacatt tctacttaca aggataacta cggaaaagct gtagctaata cttgctttaa       180
tacgtttgat tcattttttgt ctcttacgta tgtacttgtt aagcctttaa gagaaaagtt     240
tacaacttaa ggaattataa caaagaagta acacataata agtttacctt atttagtgtg       300
tatcaatcga gttctgacc tatcagcttt tgatgttagg gtattggcct aacatggcta       360
tgacgggtaa cggggaatta gagttcgatt ccggagaggg agcctgagaa atagctacca       420
```

```
catctaagga aggcagcagg cgcgtaaatt acccaattct aaagaagaga ggtagtgaca        480
agaaataaca atacaaggcc atttcatggt tttgtaattg gaatgatggg aatttaaaac        540
cttcccaaaa ttcaattgga gggcaagtct ggtgccagca gccgcggtaa ttccagctcc        600
aatagcgtat attaaaattg ttgcagttaa aacgctcgta gttgaatttc aaagaatcaa        660
tattttaagt aatgcttttg gtataagatg cttaggcaat acaacgtatc tgctctttgc        720
attccttatc caaaatgtgt tcttattata aaaaggattc tttttaaaat ctcctttact        780
ttttgtactg gagattttgt tactttgagt aaattagagt gttcaaagca aacagttaaa        840
gcattttact gcgtttgaat actacagcat ggaataacaa aattgaacaa gtcaaaactc        900
tgttcttttt tcttattttg gcttagttac gattaatagg agtagcttgg gggcatttgg        960
attcagatgt cagaggtgaa attcttagat tttctggaga caaacaactg cgaaagcatt       1020
tgcctaaaat acttccatta atcaagaacg aaagttaagg gagtgaagac gatcagatac       1080
cgtcgtaatc ttaaccataa actatgccga ctaggttttg gatgaaagat tttaaataa        1140 gaaaattcct tttggaaatt tcttagattg cttccttcag taccttatga gaaatcaaag       1200
tctttgggtt ctggggcgag tattcgcgca agcgagaaag ttaaaagaat tgacggaagg       1260
gcaccaccag gcgtggagct tgcggcttaa tttgactcaa cacggggaaa ctcactagtt       1320
taagacaaga gtaggattga cagattaata gctctttctt gatttcttgg atggtgatgc       1380
atggccgttt ttagttcgtg aatatgattt gtctggttaa ttccgataac gaacgagatc       1440
ttaacctgct aattagcggc gaatacgtta tattcctact tgaaattgaa tatagctgaa       1500
tttgcttatt ttgaagaata tattaggata cattatagtg tccttttccc ttttctactt       1560
aattcgctat tcatgctgtt tctttttttgt gtaggaatgt attcgtttga ttgtaaagct       1620
tcttagagga acgatgtgtg tctaacacaa ggaagtttaa ggcaacaaca ggtctgtgat       1680
gtccttagat gaactaggct gcacgcgtgc tacactgata tgtataacga gttactaaaa       1740 atatacttttt gtttgagtat ttatactctc tcaaatagta tacttttcct ccgccgaaag       1800
gtgtaggtaa tctttatcag tacatatcgt gatggggata gattattgca attattaatc       1860
ttgaacgagg aatgcctagt aagcatgatt catcagattg tgctgactac gtccctgccc       1920
tttgtacaca ccgcccgtcg ctcctaccga ttgaaagata tgatgaattg tttggacaag       1980
aaaagggaaa attatatttt ctttttttctg gaaaaaccgt aaatcctatc ttttaaagga       2040
aggagaagtc gtaacaaggt ttccgtaggt gaacctgcgg aaggatcatt a                2091
```

```
<210> SEQ ID NO 195
<211> LENGTH: 2152
<212> TYPE: DNA
<213> ORGANISM: Plasmodium malariae
<300> PUBLICATION INFORMATION:
<308> DATABASE ACCESSION NUMBER: AF487999.1
<309> DATABASE ENTRY DATE: 2002-05-06
<313> RELEVANT RESIDUES IN SEQ ID NO: (1)..(2152)
```

```
<400> SEQUENCE: 195
```

```
aacctggttg atcttgccag tagtcatatg cttgtctcaa agattaagcc atgcaagtga         60
aagtatatgc atattttata tgtagaaact gcgaacggct cattaaaaca gttatagtct        120
acttgacatt ttttttataa ggataactac ggaaaagctg tagctaatac ttgctttaat        180
actcttaatt ctttatgttt tttgagtatg tatttgttaa gccttataag agaaaagtat        240
attaacttaa ggaatataac aaagaagtaa cacataataa atttcgattt atttagtgtg        300
tatcaatcga gtttctgacc tatcagcttt tgatgttagg gtattggcct aacatggcta        360
```

-continued

```
tgacgggtaa cggggaatta gagttcgatt ccggagaggg agcctgagaa atagctacca      420
catctaagga aggcagcagg cgcgtaaatt acccaattct aaagaagaga ggtagtgaca      480
agaaataaca atgcaaggcc aaattttggt tttgcaattg gaatgatggg aatttaaaac      540
cttcccagaa ggcaattgga gggcaagtct ggtgccagca gccgcggtaa ttccagctcc      600
aatagcgtat attaaaattg ttgcagttaa aacgctcgta gttgaatttc aaggaatcaa      660
tattttaagt aatgctttgt atatttataa caaagttgta cattaagaat aaacgccaag      720
cgttatattt tttctgttac attttgtttt attaatatat atatgcgttc ttattataaa      780
aatgattctt tttaaaattc ttttgtataa ttttttatgc atgggaattt tgttactttg      840
agtaaattag agtgttcaaa gcaaacagtt aaaacagttt ctgtgtttga atactacagc      900
atggaataac aaaattgaac aagtcagaat tttgttcttt tttcttattt tggcttagtt      960
acgattaata ggagtagctt gggggcattt gtattcagat gtcagaggtg aaattcttag     1020
attttctgga gacaagcaac tgcgaaagca tttgcctaaa atacttccat taatcaagaa     1080
cgaaagttaa gggagtgaag acgatcagat accgtcgtaa tcttaaccat aaactatgcc     1140
gactaggtgt tggatgatag agtaaaaaat aaaagagaca ttcatatgag tgtttctttt     1200
agatagcttc cttcagtacc ttatgagaaa tcaaagtctt tgggttctgg ggcgagtatt     1260
cgcgcaagcg agaaagttaa aagaattgac ggaagggcac caccaggcgt ggagcttgcg     1320
gcttaatttg actcaacacg gggaaactca ctagtttaag acaagagtag gattgacaga     1380
ttaatagctc tttcttgatt tcttggatgg tgatgcatgg ccgttttttag ttcgtgaata     1440 tgatttgtct ggttaattcc gataacgaac gagatcttaa cctgctaatt agcggtaaat     1500
acactatatt cttaagtgaa attagaatat agataaattg tgctaatttt gattaaaata     1560
ttagaatgtt ttttttaata aaaacgttct tttccctttt tttcttaatt atgcatattt     1620 attcttttc ttttttcgca taagaatgta tttgcttaat tgtaaagctt cttagaggaa      1680
cgatgtgtgt ctaacacaag gaagtttaag gcaacaacag gtctgtgatg tccttagatg     1740
aactaggctg cacgcgtgct acactgatat gtataacgag tatttaaaaa tatatatctt     1800
gttatgttat atgtatttct atatgtatgc atgcaaagaa tatatagttt tcctccactg     1860
aaaagtgtag gtaatctttt tcaatacata tcgtgatggg gatagattat tgcaattatt     1920
aatcttgaac gaggaatgcc tagtaagcat gattcatcag attgtgctga ctacgtccct     1980
gccctttgta cacaccgccc gtcgctccta ccgattgaaa gatatgatga attgtttgga     2040
caaggaaaaa gggtttttttt cttttttctg gaaaaatcgt aaatcctatc tttttaaagga   2100 aggagaaagt cgtaacaagg tttccgtcgg tgaacctgcg gaaggatcat ta             2152
```

<210> SEQ ID NO 196
<211> LENGTH: 48
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (34)..(34)
<223> OTHER INFORMATION: y means t/u or c.
<220> FEATURE:
<221> NAME/KEY: misc_feature
<222> LOCATION: (44)..(44)
<223> OTHER INFORMATION: n means a or g or c or t/u, unknown, or other.

<400> SEQUENCE: 196

-continued guauucagau gucagaggug aaauucuuag auuyucugga gacnagca                    48

<210> SEQ ID NO 197
<211> LENGTH: 43
<212> TYPE: DNA
<213> ORGANISM: Artificial Sequence
<220> FEATURE:
<223> OTHER INFORMATION: Synthetic Oligonucleotide

<400> SEQUENCE: 197
guauucagau gucagaggug aaauucuuag auuuucugga gac                         43